US008647538B2

(12) United States Patent
Lu et al.

(10) Patent No.: US 8,647,538 B2
(45) Date of Patent: Feb. 11, 2014

(54) PHOTOCHROMIC COMPOUNDS HAVING AT LEAST TWO PHOTOCHROMIC MOIETIES

(75) Inventors: Yunyi Lu, Cockeysville, MD (US); Wenjing Xiao, Murrysville, PA (US); Robert W. Walters, Export, PA (US); Feng Wang, Export, PA (US); M. Frank Haley, Glenshaw, PA (US); Jason R. Lewis, Monaca, PA (US); Anu Chopra, Pittsburgh, PA (US); Beon-Kyu Kim, Gibsonia, PA (US); Huayun Yu, Monroeville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 24 days.

(21) Appl. No.: 13/302,316

(22) Filed: Nov. 22, 2011

(65) Prior Publication Data

US 2012/0136148 A1    May 31, 2012

Related U.S. Application Data

(60) Continuation-in-part of application No. 12/873,735, filed on Sep. 1, 2010, now Pat. No. 8,147,725, which is a continuation-in-part of application No. 12/136,339, filed on Jun. 10, 2008, now abandoned, which is a division of application No. 11/102,279, filed on Apr. 8, 2005, now abandoned.

(51) Int. Cl.
*G02B 5/23* (2006.01)
*C07D 265/30* (2006.01)
*C07D 295/00* (2006.01)

(52) U.S. Cl.
USPC .......... 252/586; 252/582; 428/411.1; 544/79; 544/222; 544/375; 549/382

(58) Field of Classification Search
USPC ........ 252/582, 586; 544/31, 79, 99, 222, 375, 544/401; 546/167, 196; 549/381, 382; 428/411.1
See application file for complete search history.

(56) References Cited

U.S. PATENT DOCUMENTS

| | | |
|---|---|---|
| 3,492,996 A | 2/1970 | Fountain |
| 3,933,509 A | 1/1976 | Noguchi et al. |
| 4,929,693 A | 5/1990 | Akashi et al. |
| 4,931,220 A | 6/1990 | Haynes et al. |
| 5,066,818 A | 11/1991 | Gemert et al. |
| 5,166,345 A | 11/1992 | Akashi et al. |
| 5,236,958 A | 8/1993 | Miyashita |
| 5,238,981 A | 8/1993 | Knowles |
| 5,252,742 A | 10/1993 | Miyashita |
| 5,274,132 A | 12/1993 | VanGemert |
| 5,359,085 A | 10/1994 | Iwamoto et al. |
| 5,458,814 A | 10/1995 | Kumar et al. |
| 5,578,252 A | 11/1996 | Van Gemert et al. |
| 5,645,767 A | 7/1997 | Van Gemert |
| 5,645,768 A | 7/1997 | Melzig et al. |
| 5,650,098 A | 7/1997 | Kumar et al. |
| 5,651,923 A | 7/1997 | Kumar et al. |
| 5,658,501 A | 8/1997 | Kumar et al. |
| 5,698,141 A | 12/1997 | Kumar |
| 5,707,557 A | 1/1998 | Melzig et al. |
| 5,723,072 A | 3/1998 | Kumar |
| 5,753,146 A | 5/1998 | Van Gemert et al. |
| 5,770,115 A | 6/1998 | Misura |
| 5,811,034 A | 9/1998 | Lin |
| 5,821,287 A | 10/1998 | Hu et al. |
| 5,952,515 A | 9/1999 | Melzig et al. |
| 5,955,520 A | 9/1999 | Heller et al. |
| 5,961,892 A | 10/1999 | Gemert et al. |
| 6,018,059 A | 1/2000 | Chan |
| 6,022,497 A | 2/2000 | Kumar |
| 6,025,026 A | 2/2000 | Smith et al. |
| 6,036,890 A | 3/2000 | Melzig et al. |
| 6,068,797 A | 5/2000 | Hunt |
| 6,096,246 A | 8/2000 | Chan et al. |
| 6,113,814 A | 9/2000 | Gemert et al. |
| 6,146,554 A | 11/2000 | Melzig et al. |
| 6,150,430 A | 11/2000 | Walters et al. |
| 6,153,126 A | 11/2000 | Kumar |
| 6,190,580 B1 | 2/2001 | Melzig et al. |
| 6,225,466 B1 | 5/2001 | Mann et al. |
| 6,296,785 B1 | 10/2001 | Nelson et al. |
| 6,340,765 B1 | 1/2002 | Momoda et al. |
| 6,392,043 B1 | 5/2002 | Bourchteine et al. |
| 6,398,987 B1 | 6/2002 | Breyne et al. |
| 6,399,791 B1 | 6/2002 | Breyne et al. |
| 6,469,076 B1 | 10/2002 | Momoda et al. |
| 6,506,322 B1 | 1/2003 | Breyne et al. |
| 6,555,028 B2 | 4/2003 | Walters et al. |
| 6,630,597 B1 | 10/2003 | Lin et al. |
| 6,641,874 B2 | 11/2003 | Kuntz et al. |
| 6,683,709 B2 | 1/2004 | Mann et al. |
| 6,719,925 B1 | 4/2004 | Breyne et al. |
| 6,723,859 B2 | 4/2004 | Kawabata et al. |
| 6,747,145 B2 | 6/2004 | Zhao et al. |
| 6,846,892 B2 | 1/2005 | Kindt-Larsen et al. |
| 6,852,254 B2 | 2/2005 | Spaulding et al. |
| 6,939,007 B2 | 9/2005 | Zhao et al. |

(Continued)

FOREIGN PATENT DOCUMENTS

EP   0446717 A2   9/1991
EP   1038870 A1   9/2000

(Continued)

OTHER PUBLICATIONS

Araujo, R. J. et al., "Photochromism," Techniques in Chemistry, 1971, pp. 734-853, vol. III, Chapter 3, Glenn H. Brown, Editor, Wiley-Interscience a Division of John Wiley & Sons, Inc.

*Primary Examiner* — Bijan Ahvazi
(74) *Attorney, Agent, or Firm* — Deborah M. Altman

(57) ABSTRACT

The present invention relates to photochromic compounds that include at least two photochromic moieties that are linked together by a multivalent linking group. The multivalent linking group can be selected so as to be flexible and/or substantially prevent electronic interaction between any two photochromic moieties through the multivalent linking group. The present invention also relates to photochromic compositions and articles that include at least a photochromic amount of one or more photochromic compounds of the present invention.

14 Claims, No Drawings

(56) References Cited

U.S. PATENT DOCUMENTS

| | | |
|---|---|---|
| 6,963,003 B2 | 11/2005 | Qin |
| 7,008,568 B2 | 3/2006 | Qin |
| 7,074,943 B2 | 7/2006 | Qin |
| 7,166,357 B2 | 1/2007 | Kumar et al. |
| 7,247,262 B2 | 7/2007 | Evans et al. |
| 7,256,246 B2 | 8/2007 | Kindt-Larsen et al. |
| 7,262,295 B2 | 8/2007 | Walters et al. |
| 7,320,826 B2 | 1/2008 | Kumar et al. |
| 7,368,072 B2 | 5/2008 | Gemert et al. |
| 7,527,754 B2 | 5/2009 | Chopra |
| 7,556,750 B2 | 7/2009 | Xiao et al. |
| 7,807,075 B2 | 10/2010 | Evans et al. |
| 2001/0025948 A1 | 10/2001 | Walters et al. |
| 2001/0039356 A1 | 11/2001 | Chan et al. |
| 2003/0000028 A1 | 1/2003 | Molock et al. |
| 2003/0071247 A1 | 4/2003 | Petrovskaia et al. |
| 2003/0141490 A1 | 7/2003 | Walters et al. |
| 2003/0165686 A1 | 9/2003 | Blackburn et al. |
| 2003/0180444 A1 | 9/2003 | Takekuma et al. |
| 2003/0236376 A1 | 12/2003 | Kindt-Larsen et al. |
| 2004/0185255 A1 | 9/2004 | Walters et al. |
| 2004/0185268 A1 | 9/2004 | Kumar et al. |
| 2004/0186241 A1 | 9/2004 | Gemert |
| 2004/0191520 A1 | 9/2004 | Kumar et al. |
| 2004/0197563 A1 | 10/2004 | Kye |
| 2005/0004361 A1 | 1/2005 | Kumar et al. |
| 2005/0037272 A1 | 2/2005 | Tanaka |
| 2005/0175306 A1 | 8/2005 | Chong et al. |
| 2005/0258408 A1 | 11/2005 | Molock et al. |
| 2006/0022176 A1 | 2/2006 | Wang et al. |
| 2006/0090848 A1 | 5/2006 | Koga et al. |
| 2006/0100408 A1 | 5/2006 | Powell et al. |
| 2006/0110520 A1 | 5/2006 | Midorikawa et al. |
| 2006/0226400 A1 | 10/2006 | Xiao et al. |
| 2006/0226401 A1 | 10/2006 | Xiao et al. |
| 2006/0226402 A1 | 10/2006 | Kim et al. |
| 2006/0227287 A1 | 10/2006 | Molock et al. |
| 2006/0228557 A1 | 10/2006 | Kim et al. |
| 2007/0001155 A1 | 1/2007 | Walters et al. |
| 2007/0249794 A1 | 10/2007 | Evans et al. |
| 2008/0103301 A1 | 5/2008 | Chopra et al. |
| 2009/0032782 A1 | 2/2009 | Kim et al. |
| 2011/0042629 A1 | 2/2011 | Chopra et al. |
| 2011/0108781 A1 | 5/2011 | Tomasulo |
| 2011/0143141 A1 | 6/2011 | He et al. |
| 2011/0190455 A1 | 8/2011 | Partington |
| 2011/0248415 A1 | 10/2011 | Alvarez-Carrigan et al. |
| 2011/0249235 A1 | 10/2011 | Duis et al. |
| 2012/0145973 A1 | 6/2012 | Bancroft et al. |
| 2012/0156508 A1 | 6/2012 | He et al. |

FOREIGN PATENT DOCUMENTS

| | | | | |
|---|---|---|---|---|
| EP | 1054010 A1 | 11/2000 | | |
| EP | 1184379 A1 | 6/2002 | | |
| JP | 2000327676 A | 11/2000 | | |
| JP | 2004131593 A | 4/2004 | | |
| WO | 9737254 A1 | 10/1997 | | |
| WO | 9740409 A1 | 10/1997 | | |
| WO | 9748762 A1 | 12/1997 | | |
| WO | 9748993 A1 | 12/1997 | | |
| WO | 9828289 A1 | 7/1998 | | |
| WO | 9915518 A1 | 4/1999 | | |
| WO | 9923071 A1 | 5/1999 | | |
| WO | 00/05325 A1 | 2/2000 | | |
| WO | 0015630 A1 | 3/2000 | | |
| WO | 0119813 A1 | 3/2001 | | |
| WO | 0160811 A1 | 8/2001 | | |
| WO | 0170719 A2 | 9/2001 | | |
| WO | 0194336 A1 | 12/2001 | | |
| WO | 03056390 A2 | 7/2003 | | |
| WO | 2004041961 A1 | 5/2004 | | |
| WO | 2005/005570 A1 | 1/2005 | | |
| WO | WO 2005/005570 | * 1/2005 | ............... | C09K 9/02 |
| WO | 2005/105874 A1 | 11/2005 | | |
| WO | 2006022825 A1 | 3/2006 | | |
| WO | 2006/110219 A1 | 10/2006 | | |
| WO | 2006/110305 A1 | 10/2006 | | |
| WO | 2006110520 A1 | 10/2006 | | |
| WO | WO 2006/110305 | * 10/2006 | ............ | G02B 11/04 |
| WO | 2010/020770 A1 | 2/2010 | | |
| WO | 2011/053615 A | 5/2011 | | |
| WO | 2011053615 A1 | 5/2011 | | |
| WO | 2011/130137 A2 | 10/2011 | | |
| WO | 2011/130139 A1 | 10/2011 | | |
| WO | 2012/082999 | 6/2012 | | |

\* cited by examiner

PHOTOCHROMIC COMPOUNDS HAVING AT LEAST TWO PHOTOCHROMIC MOIETIES

CROSS REFERENCE TO RELATED APPLICATIONS

This application is a continuation-in-part of U.S. patent application Ser. No. 12/873,735 filed Sep. 1, 2010, now U.S. Pat. No. 8,147,725, which is a continuation-in-part of Ser. No. 12/136,339 filed Jun. 10, 2008, now abandoned, which is a divisional of Ser. No. 11/102,279 filed Apr. 8, 2005, now abandoned, all of which documents are hereby incorporated herein by reference in their entireties.

FIELD

The present invention relates to photochromic compounds that have at least two photochromic moieties, in which the photochromic moieties are linked together by a multivalent linking group that can, with some embodiments, be flexible and/or substantially prevent electronic interaction between the photochromic moieties through the multivalent linking group.

BACKGROUND

In response to certain wavelengths of electromagnetic radiation (or "actinic radiation"), photochromic compounds, such as indeno-fused naphthopyrans, typically undergo a transformation from one form or state to another form, with each form having a characteristic or distinguishable absorption spectrum associated therewith. Typically, upon exposure to actinic radiation, many photochromic compounds are transformed from a closed-form, which corresponds to an unactivated (or bleached, e.g., substantially colorless) state of the photochromic compound, to an open-form, which corresponds to an activated (or colored) state of the photochromic compound. In the absence of exposure to actinic radiation, such photochromic compounds are reversibly transformed from the activated (or colored) state, back to the unactivated (or bleached) state. Compositions and articles, such as eyewear lenses, that contain photochromic compounds or have photochromic compounds applied thereto (e.g., in form of a photochromic coating composition) typically display colorless (e.g., clear) and colored states that correspond to the colorless and colored states of the photochromic compounds contained therein or applied thereto.

Upon exposure to actinic radiation (e.g., sunlight), the photochromic compound typically is transformed from the unactivated (or bleached) state to the activated (or colored) state over a period of time that is referred to as an activation time. Correspondingly, when exposure to actinic radiation is halted (e.g., due to shielding of sunlight), the photochromic compound typically is transformed from the activated (or colored) state to the unactivated (or bleached) state over a period of time that is referred to as a fade time. It is generally desirable that the activation time and the fade time associated with a photochromic material in each case be minimized. In addition, it is desirable that the fade rate associated with a photochromic compound be substantially linear. With photochromic eyewear, such as photochromic lenses, a linear fade rate allows the wearer's eyes to adjust more smoothly and less noticeably to the wearer as the lenses transform from a colored to a bleached state.

Since photochromic compounds can be expensive, it is typically desirable to minimize the amount of photochromic compound or compounds used without compromising the photochromic properties, such as optical density, of the photochromic article with which the photochromic compounds are associated. With some applications, the photochromic compounds are present in a layer, such as a coating, that is applied over an underlying article, such as an optical lens, and/or the photochromic compound is present within the article itself, which can be achieved by methods such as imbibition and/or cast-in-place methods.

Photochromic compounds can be subject to migration within the matrix, such as an organic matrix, in which they reside. With, for example, a photochromic layer or coating, the photochromic compounds can migrate out of the layer, which can result in an undesirable decrease in the photochromic properties of the photochromic layer. In some cases, a photochromic compound can migrate from a relatively soft coating layer in which the photochromic compound has favorable properties, such as good fade kinetics, into an abutting coating layer that is relatively hard and in which the photochromic compound has less favorable properties, such as undesirable fade kinetics. The overall effect, in such cases, can be a photochromic article having undesirable photochromic properties, such as undesirable fade kinetics.

It would be desirable to develop photochromic compounds that are subject to reduced migration or substantially no migration within a matrix, such as an organic matrix, in which they reside. It would also be desirable that such newly developed photochromic compounds provide a desirable level of photochromic properties.

SUMMARY

In accordance with the present invention, there is provided a photochromic compound represented by the following Formula (I),

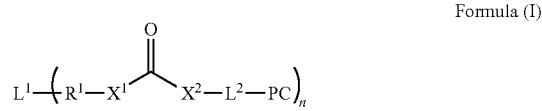

Formula (I)

With reference to Formula (I), $L^1$ is a multivalent linking group selected from multivalent amine, multivalent linear or branched $C_1$-$C_{20}$ alkyl, multivalent optionally substituted $C_3$-$C_{12}$ cycloalkyl, multivalent optionally substituted $C_3$-$C_{12}$ heterocycloalkyl, multivalent optionally substituted aryl, multivalent optionally substituted heteroaryl, —$(R^4$—O$)_q$— where $R^4$ for each q is independently selected from divalent linear or branched $C_1$-$C_{12}$ alkyl and q is from 1 to 50, and combinations of two or more thereof. Subscript n of Formula (I) is at least 2. With further reference to Formula (I), $R^1$ for each n is independently selected from a bond, divalent linear or branched $C_1$-$C_{20}$ alkyl, divalent optionally substituted $C_3$-$C_{12}$ cycloalkyl, divalent optionally substituted $C_3$-$C_{12}$ heterocycloalkyl, divalent optionally substituted aryl, divalent optionally substituted heteroaryl, and combinations of two or more thereof. With additional reference to Formula (I), $X^1$ for each n and $X^2$ for each n are each independently selected from O, NH, and a bond, provided that when $R^1$ is a bond and $X^1$ is a bond, $R^1$ and $X^1$ together define a bond.

With still further reference to Formula (I), $L^2$ for each n is independently selected from a group represented by the following Formula (II),

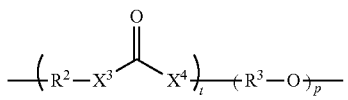

Formula (II)

The $R^2$ group of Formula (II), for each t, is independently selected from a bond, divalent linear or branched $C_1$-$C_{20}$ alkyl, divalent optionally substituted $C_3$-$C_{12}$ cycloalkyl, divalent optionally substituted aryl, divalent optionally substituted heteroaryl, and combinations of two or more thereof. The $R^3$ group of Formula (II), for each p, is independently selected from divalent linear or branched $C_1$-$C_{20}$ alkyl, divalent optionally substituted $C_3$-$C_{12}$ cycloakyl, divalent optionally substituted aryl, divalent optionally substituted heteroaryl, and combinations of two or more thereof. With further reference to Formula (II), $X^3$ for each t and $X^4$ for each t are each independently selected from O, NH, and a bond. With regard to $X^2$, $R^2$ and $X^3$ of Formula (II) there are the following provisos: provided that when $R^2$ is a bond and $X^3$ is a bond, $R^2$ and $X^3$ together define a bond; and provided that when $X^2$ is a bond, $R^2$ is a bond, $X^3$ is a bond, and t is greater than 0, $X^2$, $R^2$ and $X^3$ together define a bond. Subscript t of Formula (II), for each n, is 0 to 100. Subscript p, for each n, is 0 to 20. With regard to t and p of Formula (II), there is the following proviso, provided that the sum of t and p is greater than 0. With reference to Formula (I), PC for each n is independently a photochromic moiety or group. The invention also provides photochromic compositions and articles comprising the aforementioned compound.

DETAILED DESCRIPTION

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

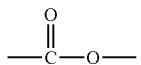

or equivalently —C(O)O—, is inclusive of the right-to-left representation thereof,

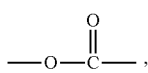

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

The photochromic compounds of the present invention as described herein, including photochromic compounds represented by Formula (I) and Formula (II), and related photochromic compounds, in each case optionally further include one or more coproducts, such as, but not limited to oligomers, resulting from the synthesis of such photochromic compounds.

As used herein, the term "multivalent" with regard to multivalent linking groups, means a group that has at least two covalent bonds that serve to link the linking group to two or more photochromic moieties. As used herein, the term "divalent" with regard to divalent linking groups, means a group that has two covalent bonds that serve to link the linking group to two substituents or portions of the photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (i.e. adapted to have an absorption spectrum for at least visible radiation that varies in response to absorption of at least actinic radiation) and which includes at least one photochromic compound.

As used herein, the term "photochromic compound" includes thermally reversible photochromic compounds and non-thermally reversible photochromic compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state.

Alternatively, a photochromic compound of the present invention can have a first color in the first state and a second color in the second state.

As used herein the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein the term "ophthalmic substrate" means lenses, partially formed lenses, and lens blanks.

As used herein the term "display" means the visible or machine-readable representation of information in words, numbers, symbols, designs or drawings. Non-limiting examples of display articles, elements and devices include screens, monitors, and security elements, such as security marks.

As used herein the term "window" means an aperture adapted to permit the transmission of radiation therethrough. Non-limiting examples of windows include automotive and aircraft transparencies, filters, shutters, and optical switches.

As used herein the term "mirror" means a surface that specularly reflects a large or substantial fraction of incident light.

As used herein the term "liquid crystal cell" refers to a structure containing a liquid crystal material that is capable of being ordered. Active liquid crystal cells are cells in which the liquid crystal material is capable of being reversibly and controllably switched or converted between ordered and disordered states, or between two ordered states by the application of an external force, such as electric or magnetic fields. Passive liquid crystal cells are cells in which the liquid crystal material maintains an ordered state. A non-limiting example of an active liquid crystal cell element or device is a liquid crystal display.

As used herein the term "coating" means a supported film derived from a flowable composition, which can or can not have a uniform thickness, and specifically excludes polymeric sheets. A layer that includes one or more photochromic compounds of the present invention can, with some embodiments, be a photochromic coating.

As used herein the term "sheet" means a pre-formed film having a generally uniform thickness and capable of self-support.

As used herein the term "connected to" means in direct contact with an object or indirect contact with an object through one or more other structures or materials, at least one of which is in direct contact with the object. For purposes of non-limiting illustration, a coating containing one or more photochromic compounds of the present invention, for example, can be in direct contact (e.g., abutting contact) with at least a portion of a substrate, such as an optical article, or it can be in indirect contact with at least a portion of the substrate through one or more other interposed structures or materials, such as a monomolecular layer of a coupling or adhesive agent. For example, although not limiting herein, a coating containing one or more photochromic compounds of the present invention, can be in contact with one or more other interposed coatings, polymer sheets or combinations thereof, at least one of which is in direct contact with at least a portion of the substrate.

As used herein, the term "photosensitive material" means materials that physically or chemically respond to electromagnetic radiation, including, but not limited to, phosphorescent materials and fluorescent materials.

As used herein, the term "non-photosensitive materials" means materials that do not physically or chemically respond to electromagnetic radiation, including, but not limited to, static dyes.

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means methacrylates and/or acrylates. As used herein, the term "(meth)acrylic acid" means methacrylic acid and/or acrylic acid.

Other than in the operating examples, or where otherwise indicated, all numbers expressing quantities of ingredients, reaction conditions, and so forth used in the specification and claims are to be under-stood as modified in all instances by the term "about."

As used herein, spatial or directional terms, such as "left", "right", "inner", "outer", "above", "below", and the like, relate to the invention as it is depicted in the drawing figures. However, it is to be understood that the invention can assume various alternative orientations and, accordingly, such terms are not to be considered as limiting.

As used herein, the terms "formed over," "deposited over," "provided over," "applied over," "residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein, recitations of "optionally substituted" group, means a group, including but not limited to, alkyl group, cycloalkyl group, heterocycloalkyl group, aryl group, and/or heteroaryl group, in which at least one hydrogen thereof has been optionally replaced or substituted with a group that is other than hydrogen, such as, but not limited to, halo groups (e.g., F, Cl, I, and Br), hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl, including poly-fused-ring cycloalkyl and polycyclocalkyl; heterocycloalkyl; aryl, including hydroxyl substituted aryl, such as phenol, and including poly-fused-ring aryl; heteroaryl, including poly-fused-ring heteroaryl; and aralkyl groups), and amine groups, such as —N($R^{11}$)($R^{12}$) where $R^{11}$ and $R^{12}$ are each independently selected from hydrogen, linear or branched $C_1$-$C_{20}$ alkyl, $C_3$-$C_{12}$ cycloakyl, $C_3$-$C_{12}$ heterocycloalkyl, aryl, and heteroaryl.

As used herein, the term "alkyl" means linear or branched $C_1$-$C_{20}$ alkyl, such as, but not limited to linear or branched $C_1$-$C_{10}$ alkyl or linear or branched $C_2$-$C_{10}$ alkyl. Examples of alkyl groups from which the various alkyl groups of the present invention can be selected from, include, but are not limited to, methyl, ethyl, propyl, isopropyl, butyl, isobutyl, sec-butyl, tert-butyl, pentyl, neopentyl, hexyl, heptyl, octyl, nonyl and decyl. Alkyl groups of the various compounds of the present invention can, with some embodiments, include one or more unsaturated linkages selected from —CH=CH— groups and/or one or more —C≡C— groups, provided the alkyl group is free of two or more conjugated unsaturated linkages. With some embodiments, the alkyl groups are free of unsaturated linkages, such as —CH=CH— groups and —C≡C— groups.

As used herein, the term "cycloalkyl" means groups that are appropriately cyclic, such as $C_3$-$C_{12}$ cycloalkyl (including, but not limited to, cyclic $C_5$-$C_7$ alkyl) groups. Examples of cycloalkyl groups include, but are not limited to, cyclopropyl, cyclobutyl, cyclopentyl, cyclohexyl, and cyclooctyl. The term "cycloalkyl" as used herein also includes: polycycloalkyl groups (or polycyclic alkyl groups), such as but not limited to, bicyclo[2.2.1]heptyl (or norbornyl) and bicyclo[2.2.2]octyl; and fused ring polycyclic alkyl groups, such as, but not limited to, octahydro-1H-indenyl, and decahydronaphthalenyl.

As used herein, the term "heterocycloalkyl" means groups that are appropriately cyclic, such as $C_3$-$C_{12}$ heterocycloalkyl groups or $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, tetrahydrofuranyl, tetrahydropyranyl and piperidinyl. The term "heterocycloalkyl" as used herein also includes: polycyclic heterocycloalkyl groups, such as but not limited to, 7-oxabicyclo[2.2.1]heptanyl; and fused ring polycyclic heterocycloalkyl groups, such as but not limited to, octahydrocyclopenta[b]pyranyl, and octahydro-1H-isochromenyl.

As used herein, the term "aryl" includes, but is not limited to, $C_6$-$C_{18}$ aryl, such as but not limited to, $C_6$-$C_{10}$ aryl (including polycyclic fused ring aryl groups). Examples of aryl groups include, but are not limited to, phenyl, naphthyl, and anthracenyl.

As used herein, the term "heteroaryl," includes but is not limited to $C_5$-$C_{18}$ heteroaryl, such as but not limited to $C_5$-$C_{10}$ heteroaryl (including polycyclic fused ring heteroaryl groups) and means an aryl group having at least one hetero atom in the aromatic ring. Examples of heteroaryl groups include, but are not limited to, furanyl, pyranyl and pyridinyl.

As used herein, the term "aralkyl" means an aryl group substituted with an alkyl group that is bonded (or linked) to another group, which term" includes, but is not limited to $C_6$-$C_{24}$ aralkyl, such as but not limited to $C_6$-$C_{10}$ aralkyl. Examples of aralkyl groups include, but are not limited to, benzyl, and phenethyl.

As used herein the term "n-segment" means a segment of a photochromic compound according to the present invention that is bonded to the multivalent linking group $L^1$. For purposes of non-limiting illustration, and with reference to Formula (I), when n is 3, the photochromic compound can be described as having three n-segments that are each bonded to trivalent linking group $L^1$; the three n-segments can be further described as a first n-segment, a second n-segment, and a third n-segment, in which any one such n-segment is the same or different than any other such n-segment.

The photochromic compounds of the present invention, and compositions containing such photochromic compounds, will be described in further detail as follows.

With reference to Formula (I), subscript n is at least 2. With some embodiments, subscript n can be from 2 to 10, or from 2 to 5, or from 2 to 4, or from 2 to 3. Subscript q of —($R^4$—O)$_q$— of $L^1$ of Formula (I) can be, with some embodiments, from 1 to 50, or from 1 to 30, or from 1 to 20, or from 1 to 10, or from 1 to 5, or from 1 to 3. With reference to Formula (II), subscript t can, with some embodiments, be from 0 to 100, or from 0 to 50, or from 0 to 30, or from 0 to 20, or from 0 to 15, or from 0 to 10, or from 0 to 5, or from 0 to 3. With further reference to Formula (II), and with some embodiments, subscript p can be from 0 to 20, or from 0 to 15, or from 0 to 10, or from 0 to 5, or from 0 to 3.

With reference to Formulas (I) and (II), the alkyl groups, cycloalkyl groups, heterocycloalkyl groups, aryl groups, and heteroaryl groups from which the various multivalent and divalent linking groups, such as multivalent linking group $L^1$, divalent $R^1$, divalent $R^2$, divalent $R^3$, and divalent $R^4$ can each be independently selected include, but are not limited to, those classes and examples of alkyl groups, cycloalkyl groups, heterocycloalkyl groups, aryl groups, and heteroaryl groups as described previously herein.

The photochromic moieties (PC) of the photochromic compounds, with some embodiments, are linked together by linkages or linking groups that limit, or inhibit, or prevent electronic interaction between any two photochromic moieties through the linking group. An example of electronic interaction includes, but is not limited to, extension of the pi-conjugated system of one photochromic moiety through the linking group with the pi-conjugated system of another photochromic moiety bonded to the same linking group. In accordance with some embodiments, $L^1$, $R^1$, $X^1$, $X^2$ and $L^2$ are each selected so as to substantially prevent electronic interaction between any two photochromic moieties of the photochromic compound through $L^1$, $R^1$, $X^1$, $X^2$ and $L^2$. In accordance with some further embodiments, $L^1$, $R^1$, $X^1$, $X^2$ and $L^2$ are each selected so as to substantially prevent extension of the pi-conjugated system of any photochromic moiety through $L^1$, $R^1$, $X^1$, $X^2$ and $L^2$ with the pi-conjugated system of any other photochromic moiety of the photochromic compound. In accordance with some further additional embodiments, $L^1$, $R^1$, $X^1$, $X^2$ and $L^2$ are each selected so as to be substantially free of conjugated pi-bonds that provide extension of the pi-conjugated system of any photochromic moiety through $L^1$, $R^1$, $X^1$, $X^2$ and $L^2$ with the pi-conjugated system of any other photochromic moiety of the photochromic compound.

In addition or alternatively to preventing electronic interaction between any two photochromic moieties therethrough, $L^1$, $R^1$, $X^1$, $X^2$ and $L^2$ are each selected, with some embodiments, so as to provide a flexible linkage between each photochromic moiety (PC) of the photochromic compounds of the present invention. With some embodiments, $L^1$, $R^1$, $R^2$ and $R^3$ are each independently selected from multivalent/divalent linear or branched optionally substituted $C_1$-$C_{20}$ alkyl, multivalent/divalent optionally substituted $C_3$-$C_{12}$ cycloalkyl, multivalent/divalent optionally substituted $C_3$-$C_{12}$ heterocycloalkyl, and combinations of two or more thereof, and alternatively or additionally, $R^1$ and $R^2$ can each be independently selected from a bond, subject to the provisos as recited previously herein.

With some embodiments, so as to (i) prevent, or substantially prevent, electronic interaction between the photochromic moieties (such as, between any two photochromic moieties) therethrough, and/or (ii) provide a flexible linkage between each photochromic moiety (PC) of the photochromic compounds of the present invention, $L^1$, $R^1$, $R^2$ and $R^3$ are each independently selected from multivalent/divalent linear or branched optionally substituted $C_1$-$C_{20}$ alkyl, and/or multivalent/divalent optionally substituted $C_3$-$C_{12}$ cycloalkyl, and combinations of two or more thereof, and alternatively or additionally, $R^1$ and $R^2$ can each be independently selected from a bond, subject to the provisos as recited previously herein.

With reference to Formula (I), and with some embodiments of the present invention: n is 2; $L^1$ is a divalent linking group selected from divalent linear or branched optionally substituted $C_1$-$C_{20}$ alkyl, divalent optionally substituted $C_3$-$C_{12}$ cycloalkyl, divalent optionally substituted aryl, divalent optionally substituted heteroaryl, and combinations of two or more thereof; $R^1$ is a bond; $X^1$ is NH; and $X^2$ is O.

When $X^1$ is NH and $X^2$ is O, the photochromic compounds of the present invention can, with some embodiments, be prepared from isocyanate functional materials having at least two isocyanate, groups. Examples of isocyanate functional materials from which the photochromic compounds of the present invention can be prepared include, but are not limited to: alkylene diisocyanates, such as hexamethylene diisocyanate; aromatic isocyanates, such as toluene diisocyanate, methylene diphenyl 4,4'-diisocyanate, meta-tetramethylxylene diisocyanate (also referred to as m-TMXDI), triphenylmethane-4,4',4"-triisocyanate, naphthalene diisocyanate, such as naphthalene 1,5-diisocyanate, and phenylene diisocyanate, such as p-phenylene diisocyanate; cycloalkyl isocyanates, such as isocyanato-1-(isocyanatomethyl)-1,3,3-trimethyl-cyclohexane, for example 5-isocyanato-1-(isocyanatomethyl)-1,3,3-trimethyl-cyclohexane (also referred to as isophorone diisocyanate or IPDI), and methylene dicyclohexyl diisocyanate, such as methylene dicyclohexyl 4,4'-diisocyanate; and dimmers and trimers of any combination of such isocyanate functional materials (such as diisocyanate containing isocyanurate, uretidino, biruet and/or allophanate linkages.

Photochromic compounds according to some embodiments of the present invention, can be described with reference to: Formula (I) in which n is 2, $L^1$ is a divalent linking group selected from divalent linear or branched optionally substituted $C_1$-$C_{20}$ divalent, optionally substituted $C_3$-$C_{12}$ cycloalkyl, divalent optionally substituted aryl, divalent optionally substituted heteroaryl, and combinations of two or more thereof, $R^1$ is a bond, $X^1$ is NH, and $X^2$ is O; and Formula (II) in which t is 0, p is from 1 to 5, and $R^3$ for each p is independently divalent linear or branched $C_2$-$C_{10}$ alkyl, such as ethan-1,2-diyl or pram-1,2-diyl. Photochromic compounds according to such non-limiting embodiments of the present invention can, with some embodiments, be prepared by reaction of 2 moles of a hydroxyl functional photochromic reactant (or intermediate) with one mole of a difunctional isocyanate.

With some embodiments, the photochromic compounds of the present invention can be described with reference to: Formula (I) in which n is 2, $L^1$ is a divalent linking group selected from divalent linear or branched optionally substituted $C_1$-$C_{20}$ alkyl, divalent optionally substituted $C_3$-$C_{12}$ cycloalkyl, divalent optionally substituted aryl, divalent optionally substituted heteroaryl, and combinations of two or more thereof, $R^1$ is a bond, $X^1$ is NH, and $X^2$ is O, and Formula (II) in which t is from 1 to 10, $R^2$ for each t is independently selected from divalent linear or branched $C_1$-$C_{10}$ alkyl, $X^3$ is a bond, $X^4$ is O, p is from 1 to 5, and $R^3$ for each p is independently divalent linear or branched $C_2$-$C_{10}$ alkyl. Photochromic compounds according to such non-limiting embodiments of the present invention can, with some embodiments, be prepared by reaction of one mole of a hydroxyl functional photochromic reactant with one or more moles of a cyclic carboxylic acid ester, such as a lactone, including but not limited to e-caprolactone, which results in the formation of a hydroxyl functional lactone extended photochromic intermediate. Two moles of the hydroxyl functional lactone extended photochromic intermediate can then be reacted, with some embodiments, with a difunctional isocyanate.

In accordance with some embodiments, the photochromic compounds of the present invention can be described with reference to Formula (I) in which n is 2, $R^1$ is a bond, $X^1$ is NH, $X^2$ is O, and $L^1$ is more particularly selected from: divalent linear or branched optionally substituted $C_1$-$C_{20}$ alkyl, such as divalent linear or branched $C_1$-$C_6$ alkyl, such as hexamethan-1,6-diyl; a structure represented by the following Formula (III),

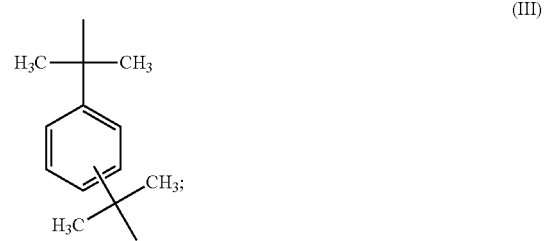

a structure represented by the following Formula (IV),

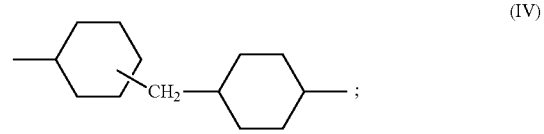

and
a structure represented by the following Formula (V),

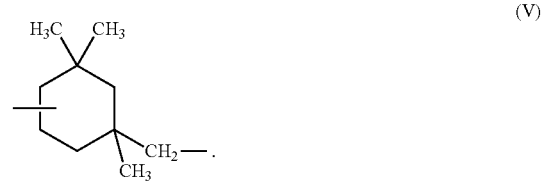

For purposes of non-limiting illustration, see Formulas (VII-a) through (VII-e) further herein.

As discussed previously herein with reference to Formula (I), when $X^1$ is NH and $X^2$ is O, the photochromic compounds of the present invention can, with some embodiments, be prepared from isocyanate functional materials having at least two isocyanate groups. With some embodiments, when the multivalent linking group $L^1$ is selected from divalent linear or branched $C_1$-$C_{20}$ alkyl, multivalent linking group $L^1$ can be a residue of a diisocyanate, such as, but not limited to, hexamethylene diisocyanate, for example, 1,6-hexamethylene diisocyanate. With some additional embodiments, the divalent linking group $L^1$ represented by Formula (III) is a residue of a diisocyanate, such as tetramethylxylene diisocyanate, for example, meta-tetramethylxylene diisocyanate. With some further embodiments, the divalent linking group $L^1$ represented by Formula (IV) is a residue of a diisocyanate, such as methylene dicyclohexyl diisocyanate, for example, methylene dicyclohexyl 4,4'-diisocyanate. In accordance with some additional embodiments, the divalent linking group $L^1$ represented by Formula (V) is a residue of a diisocyanate, such as isocyanato-1-(isocyanatomethyl)-1,3,3-trimethyl-cyclohexane, for example, 5-isocyanato-1-(isocyanatomethyl)-1,3,3-trimethyl-cyclohexane (also called isophorone diisocyanate).

Photochromic compounds according to further embodiments of the present invention can be described with reference to Formula (I), in which n is 3, $X^1$ is NH, $X^2$ is O, and $L^1$ is represented by the following Formula (VI),

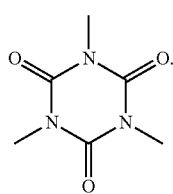

(VI)

When, in accordance with some embodiments of the present invention with reference to Formula (I), n is 3, $X^1$ is NH, $X^2$ is O, $R^1$ is not a bond, and $L^1$ is represented by Formula (VI), the trivalent linking group $L^1$ can be a residue of a trimer of three moles of one or more diisocyanates, such as a trimer of hexamethylene-1,6-diisocyanate.

With some embodiments, the photochromic compounds of the present invention can be described with reference to Formula (I), in which n is 3, $X^1$ is NH, $X^2$ is O, and $L^1$ is represented by Formula (VI), and additionally in which $R^1$ for each n is independently selected from linear or branched $C_1$-$C_{20}$ alkyl. Photochromic compounds according to such non-limiting embodiments of the present invention can be prepared, with some embodiments, from a trifunctional isocyanate that is a trimer of three moles of one or more diisocyanates, such as a trimer of hexamethylene-1,6-diisocyanate.

Photochromic compounds according to some embodiments of the present invention, can be described with reference to: Formula (I), in which n is 3, $X^1$ is NH, $X^2$ is O, and $L^1$ is represented by Formula (VI), and $R^1$ for each n is independently selected from linear or branched $C_1$-$C_{20}$ alkyl; and Formula (II), in which t is 0, p is from 1 to 5, and $R^3$ for each p is independently divalent linear or branched $C_2$-$C_{10}$ alkyl. Photochromic compounds according to such non-limiting embodiments of the present invention can, with some embodiments, be prepared by reaction of three moles of a hydroxyl functional photochromic reactant with one mole of a trimer of a diisocyanate, such as a trimer of hexamethylene-1,6-diisocyanate. For purposes of non-limiting illustration, see Formulas (VII-f) and (VII-f-a) further herein.

According to some embodiments the photochromic compounds of the present invention can be described with reference to; Formula (I), in which n is 3, $X^1$ is NH, $X^2$ is O, and $L^1$ is represented by Formula (VI), and $R^1$ for each n is independently selected from linear or branched $C_1$-$C_{20}$ alkyl; and Formula (II), in which t is from 1 to 10, $R^2$ for each t is independently selected from divalent linear or branched $C_1$-$C_{10}$ alkyl, $X^3$ is a bond, $X^4$ is O, p is from 1 to 5, and $R^3$ for each p is independently selected from divalent linear or branched $C_2$-$C_{10}$ alkyl. Photochromic compounds according to such non-limiting embodiments of the present invention can, with some embodiments, be prepared by reaction of one mole of a hydroxyl function photochromic reactant with one or more moles of a cyclic carboxylic acid ester, such as a lactone, for example, e-caprolactone, which results in the formation of a hydroxyl functional lactone extended photochromic intermediate. Subsequently, three moles of the hydroxyl functional lactone extended photochromic intermediate can be reacted with one mole of a trimer of a diisocyanate, such as a trimer of hexamethylene-1,6-diisocyanate, which results in formation of a photochromic compound according to a non-limiting embodiment of the present invention. For purposes of non-limiting illustration, see Formulas (VII-g) and (VII-g-a) further herein.

In accordance with some embodiments, the photochromic compounds of the present invention can be described with reference to Formula (I), in which n is 3, and the photochromic compound has a first n-segment, a second n-segment, and a third n-segment, and $L^1$ is N. In accordance with such non-limiting embodiments of the present invention, the trivalent linking group $L^1$ can be a residue of a trimer of a diisocyanate, that includes biuret linkages, such as hexamethylene-1,6-diisocyanate.

With some additional embodiments, the photochromic compounds of the present invention can be described with reference to Formula (I) in which n is 3, and the photochromic compound has a first n-segment, a second n-segment, and a third n-segment, $L^1$ is N, and additional in which: for said first n-segment, $R^1$ is divalent linear or branched optionally substituted $C_1$-$C_{20}$ alkyl, $X^1$ is NH, and $X^2$ is O; and for each of said second n-segment and said third n-segment, $R^1$ and $X^1$ together define a bond, and $X^2$ is NH.

With some further embodiments, the photochromic compounds of the present invention can be described with reference to: Formula (I) in which n is 3, and the photochromic compound has a first n-segment, a second n-segment, and a third n-segment, $L^1$ is N, and additional in which: for said first n-segment, $R^1$ is divalent linear or branched optionally substituted $C_1$-$C_{20}$ alkyl, $X^1$ is NH, and $X^2$ is O; and for each of said second n-segment and said third n-segment, $R^1$ and $X^1$ together define a bond, and $X^2$ is NH; and Formula (II), in which t is 0, p is from 1 to 5, and $R^3$ for each p is independently divalent linear or branched $C_2$-$C_{10}$ alkyl. Photochromic compounds according to such non-limiting embodiments of the present invention can be prepared by reaction of two moles of a hydroxyl functional photochromic reactant with one mole of a trimer of a diisocyanate, in the form of a biuret, such as hexamethylene-1,6-diisocyanate, such as DESMODUR N 3200 polyisocyanate, which is commercially available from Bayer MaterialScience LLC. For purposes of non-limiting illustration, see, for example, Formula (VII-h) further herein.

Photochromic compounds in accordance with additional embodiments of the present invention can be described with reference to Formula (I), in which n is 2; $L^1$ for each n is independently divalent linear or branched optionally substituted $C_1$-$C_{20}$ alkyl; $R^1$ is a bond; $X^1$ is O; and $X^2$ is a bond.

Photochromic compounds according to some further embodiments of the present invention, can be described with reference to: Formula (I), in which n is 2, $L^1$ for each n is independently divalent linear or branched optionally substituted $C_1$-$C_{20}$ alkyl, $R^1$ is a bond, $X^1$ is O, and $X^2$ is a bond, and Formula (II), in which t is 1, $R^2$ is divalent linear or branched $C_1$-$C_{10}$ alkyl, $X^3$ is a bond, and $X^4$ is O.

With some embodiments, some photochromic compounds of the present invention can be described with reference to: Formula (I), in which n is 2, $L^1$ for each n is independently divalent linear or branched optionally substituted $C_1$-$C_{20}$ alkyl, $R^1$ is a bond, $X^1$ is O, and $X^2$ is a bond, and Formula (II), in which t is 1, $R^2$ is divalent linear or branched $C_1$-$C_{10}$ alkyl, $X^3$ is a bond, $X^4$ is O, p is 1 to 5, and $R^3$ for each p is independently divalent linear or branched $C_2$-$C_{10}$ alkyl, Photochromic compounds according to such non-limiting embodiments of the present invention can be prepared, with some embodiments, by reaction of one mole of a hydroxyl functional photochromic compound and a cyclic carboxylic acid anhydride, such as, but not limited to, succinic anhydride, which results in the formation of a carboxylic acid functional photochromic intermediate. In accordance with some embodiments, the hydroxyl functionality of the hydroxyl functional photochromic compound is provided by: a hydroxyl functional alkoxy group, such as but not limited to, —O—R—OH, where R is a divalent hydrocarbyl group, such as divalent linear or branched $C_1$-$C_{20}$ alkyl, divalent $C_3$-$C_{12}$ cycloalkyl, divalent $C_3$-$C_{12}$ heterocycloalkyl, divalent aryl, divalent heteroaryl, and combinations of two or more thereof, or a hydroxyl functional hydrocarbyl group, such as —R—OH, where R is as described above. Two moles of the carboxylic acid functional photochromic intermediate can then be reacted, in some embodiments, with one mole of a diol, such as a linear or branched $C_2$-$C_{20}$ alkyl (or alkane) diol, for example, decane-1,10-diol, with concurrent removal of water, which results in formation of a photochromic compound according to a non-limiting embodiment of the present invention. For purposes of non-limiting illustration, see Formula (VII-i) further herein.

Photochromic compounds in accordance with some embodiments of the present invention can be described with reference to Formula (I), in which n is 2, $L^1$ is divalent linear or branched optionally substituted $C_1$-$C_{20}$ alkyl, $R^1$ is a bond, $X^1$ is O, and $X^2$ is O. When $X^1$ and $X^2$ of Formula (I) are each O, the photochromic compounds of the present invention include at least one carbonate linkage between $L^1$ and at least one PC moiety.

With some embodiments, some photochromic compounds of the present invention can be described with reference to: Formula (I), in which n is 2, $L^1$ is divalent linear or branched optionally substituted $C_1$-$C_{20}$ alkyl, $R^1$ is a bond, $X^1$ is O, and $X^2$ is O; and Formula (II), in which t is 0, p is from 1 to 5, and $R^3$ for each p is independently divalent linear or branched $C_2$-$C_{10}$ alkyl. Photochromic compounds according to such non-limiting embodiments of the present invention can be prepared, with some embodiments, by reaction of two moles of a hydroxyl functional photochromic reactant and one mole of a bishaloformate, such as a linear or branched $C_1$-$C_{20}$ alkyl (or alkane) bishaloformate, for example 1,6-hexane bischloroformate, which results in the formation of a photochromic compound according to a non-limiting embodiment of the present invention. For purposes of non-limiting illustration, see Formula (VII-j) further herein.

Further photochromic compounds in accordance with some embodiments of the present invention, can be described with reference to: Formula (I), in which n is 2, $L^1$ is divalent linear or branched optionally substituted $C_1$-$C_{20}$ alkyl, $R^1$ is a bond, $X^1$ is O, and $X^2$ is O; and Formula (II), in which t is from 1 to 100, such as from 1 to 50, or 1 to 30, or 1 to 20, or 1 to 10, or 1 to 5, or 1 to 3, $R^2$ for each t is independently divalent linear or branched optionally substituted $C_1$-$C_{20}$ alkyl, $X^3$ and $X^4$ for each t are each O, and p is 0. Photochromic compounds according to such non-limiting embodiments of the present invention can be prepared, with some embodiments, by reaction of: a hydrocarb-diyl-dicarbonohalodate (X(O)CO—R—OC(O)X, where R is a hydrocarb-diyl and X is halo), such as a hydrocarb-diyl-dicarbonochloridate, such as an alkane-diyl-dicarbonochloridate, such as ethane-1,2-diyl-dicarbonochloridate; and a diol, such as an alkane diol, such as 1,6-hexane diol, in which the moles of hydrocarb-diyl-dicarbonohalodate and moles of diol are selected so as to result in the formation of a chain extended dicarbonohalodate functional intermediate. For purposes of non-limiting illustration, the terms hydrocarb-diyl-dicarbonohalodate, hydrocarb-diyl-dicarbonochloridate, alkane-diyl-dicarbonochloridate and ethane-1,2-diyl-dicarbonochloridate are equivalent to hydrocarb-diol-bishaloformate, hydrocarb-diol-bischloroformate, alkyleneglycolbischloroformate, and ethyleneglycolbischloroformate, respectively. The chain extended dicarbonohalodate functional intermediate is then reacted with two moles of an active hydrogen functional photochromic reactant, such as a hydroxyl functional photochromic reactant, which results in the formation of a photochromic compound according to some embodiments of the present invention. Such photochromic compounds can, in accordance with some embodiments, be described as oligomeric or polymeric polycarbonates having terminal photochromic moieties. For purposes of non-limiting illustration, see Formula (VII-m) further herein.

Photochromic compounds in accordance with some embodiments of the present invention can be described with reference to Formula (I), in which n is 2, $L^1$ for each n is independently selected from divalent linear or branched optionally substituted $C_1$-$C_{20}$ alkyl, divalent optionally substituted $C_3$-$C_{12}$ cycloalkyl, divalent optionally substituted $C_3$-$C_{12}$ heterocycloalkyl, divalent optionally substituted aryl, and combinations of two or more thereof, $R^1$ and $X^1$ together define a bond, and $X^2$ is O.

With some embodiments, some photochromic compounds of the present invention can be described with reference to: Formula (I), in which n is 2, $L^1$ for each n is independently selected from divalent linear or branched optionally substituted $C_1$-$C_{20}$ alkyl, divalent optionally substituted $C_3$-$C_{12}$ cycloalkyl, divalent optionally substituted $C_3$-$C_{12}$ heterocycloalkyl, divalent optionally substituted aryl, divalent optionally substituted heteroaryl, and combinations of two or more thereof, $R^1$ and $X^1$ together define a bond, and $X^2$ is O; and Formula (II), t is 0, p is from 1 to 5, and $R^3$ for each p is independently divalent linear or branched $C_2$-$C_{10}$ alkyl. Photochromic compounds according to such non-limiting embodiments of the present invention can be prepared, with some embodiments, by reaction of two moles of a hydroxyl functional photochromic reactant and one moles of a bis carboxylic acid halide, such as a linear or branched $C_2$-$C_{20}$ alkyl (or alkane) bis carboxylic acid halide, for example decanedioyl dichloride (also referred to a sebacoyl chloride), which results in the formation of a photochromic compound according to a non-limiting embodiment of the present invention. For purposes of non-limiting illustration, see Formula (VII-k) further herein.

Additional photochromic compounds in accordance with some embodiments of the present invention can be described with reference to Formula (I), in which n is 2, and said photochromic compound has a first n-segment and a second n-segment, and $L^1$ is —$(R^4$—$O)_q$—. For the first n-segment, $R^1$ and $X^1$ together define a bond. For the second n-segment, $R^1$ is a bond, and $X^1$ is O. For the first n-segment and said second n-segment, $X^2$ is a bond. With further accordance with this non-limiting embodiment of the present invention, and removal of water, which results in the formation of a photochromic compound according to a non-limiting embodiment of the present invention. For purposes of non-limiting illustration, see Formula (VII-1) further herein.

Examples of photochromic compounds according to the present invention include, but are not limited to, those represented by the following Formulas (VII-a) through (VII-l).

Formula (VII-a)
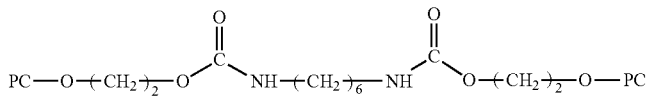

Formula (VII-b)
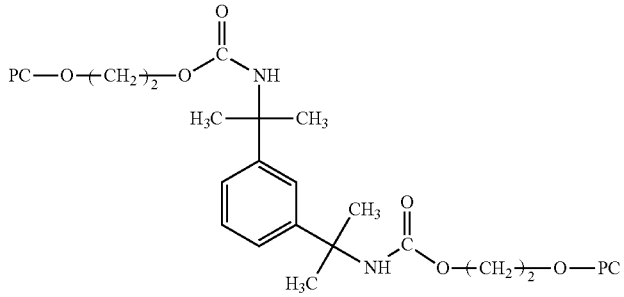

Formula (VII-c)
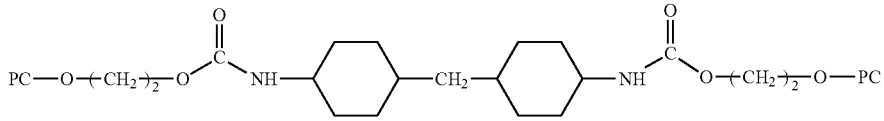

Formula (VII-d)
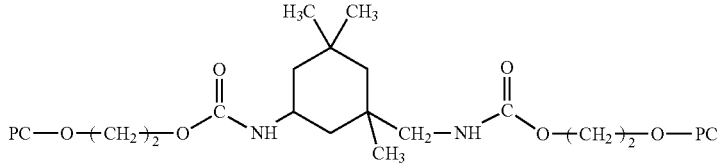

Formula (VII-e)
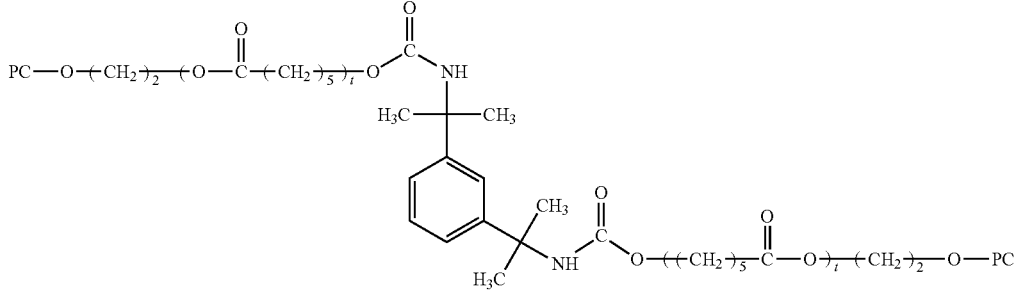

with reference to Formula (II), for the first n-segment and the second n-segment, t is 1, $R^2$ is linear or branched $C_1$-$C_{10}$ alkyl, $X^3$ is a bond, $X^4$ is O, p is from 1 to 5, and $R^3$ for each p is independently selected from divalent linear or branched $C_2$-$C_{10}$ alkyl. Photochromic compounds according to such non-limiting embodiments of the present invention can be prepared, with some embodiments, by reaction of one mole of a hydroxyl functional photochromic reactant and one mole of an cyclic carboxylic acid anhydride, such as, but not limited to, succinic anhydride, which results in the formation of a carboxylic acid functional photochromic intermediate. Two moles of the carboxylic acid functional photochromic intermediate can then be reacted, in some embodiments, with one mole of a polyalkylene glycol, such as a polyethylene glycol, for example tetraethylene glycol, with the concurrently Where with Formula (VII-e), each t is independently selected from 1 to 100, or 1 to 50, or 1 to 30, or 1 to 20, or 1 to 15, or 1 to 10, such as, with some embodiments, 4, 8, or 9.5.

Formula (VII-f)
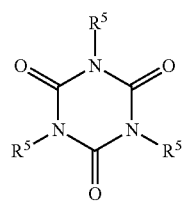

With Formula (VII-f), each $R^5$ is represented by the following Formula (VII-f-a)

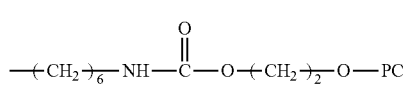
Formula (VII-f-a)

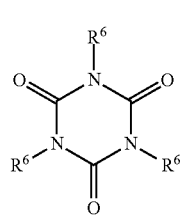
Formula (VII-g)

With Formula (VII-g), each $R^6$ is represented by the following Formula (VII-g-a).

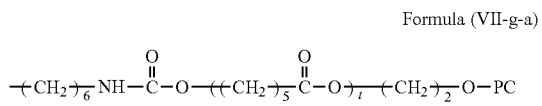
Formula (VII-g-a)

With Formula (VII-g-a), each t is independently from 1 to 100, or 1 to 50, or 1 to 30, or 1 to 20, or 1 to 15, or 1 to 10, such as with some embodiments 4.5, or 8, or 10.

With reference to Formula (VII-m), u' of each of the two n-segments is independently at least 1, such as with some embodiments from 1 to 49, or 1 to 40, or 1 to 30, or 1 to 20, or 1 to 10. With some embodiments, each $R^a$ is independently a residue of a diol, and each $R^b$ is independently a residue of a hydrocarb-diyl-dicarbonohalodate. With further reference to Formula (VII-m), each $R^a$ and each $R^b$ can, with some embodiments, each be independently selected from divalent linear or branched optionally substituted $C_1$-$C_{20}$ alkyl, such as, but not limited to, n-hexane-1,6-diyl and ethane-1,2-diyl. In accordance with some embodiments, $R^a$ is the same as $R^b$ and correspondingly $R^b$ is the same as $R^a$.

Each divalent linking group $L^2$ of the photochromic compounds of the present invention can, with some embodiments, be independently bonded to any appropriate portion of each photochromic moiety (PC), including any group bonded to the photochromic moiety. For purposes of non-limiting illustration, with a photochromic moiety selected from an indeno-fused naphthopyran, $L^2$ can be bonded: (i) directly to a ring of the indeno-fused naphthopyran; or (ii) to a group, such as an interposed group, that is bonded to a ring of the indeno-fused naphthopyran. Examples of groups, such as interposed groups, of the photochromic moiety (PC) to which each $L^2$ can independently be bonded include, but are not limited to: —O—; —S—; —NR*—, where R* is hydrogen or hydrocarbyl, such as, linear or branched $C_1$-$C_{20}$ alkyl, $C_3$-$C_{12}$ cycloalkyl, $C_3$-$C_{12}$ heterocycloalkyl, aryl, and heteroaryl; —C(O)—; —O—C(O)—; —O—C(O)—O—; —NR*—C(O)—, were R* is as described above; —NH—C(O)—O—;

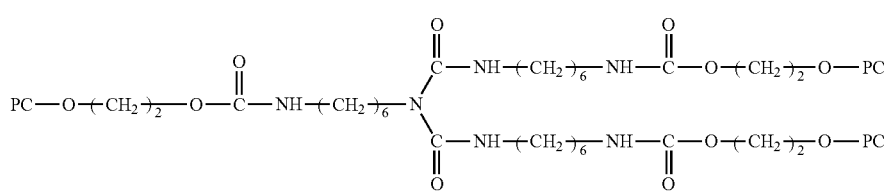
Formula (VII-h)

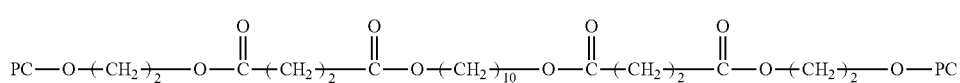
Formula (VII-i)

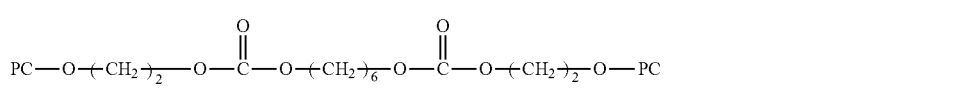
Formula (VII-j)

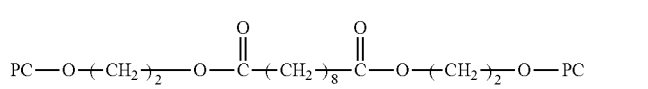
Formula (VII-k)

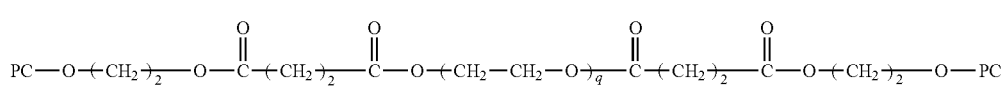
Formula (VII-l)

With Formula (VII-l), q is from 1 to 20, or from 1 to 10, or from 1 to 8, such as, with some embodiments, 4.

divalent linear or branched $C_1$-$C_{20}$ alkyl; divalent $C_3$-$C_{12}$ cycloalkyl; divalent $C_3$-$C_{12}$ heterocycloalkyl; divalent aryl;

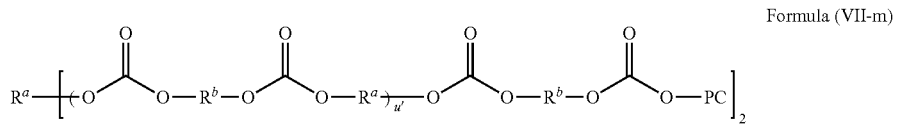
Formula (VII-m)

divalent heteroaryl; divalent poly(alkylene oxide); and combinations of two or more thereof.

The photochromic moieties (PC) of the photochromic compounds of to the present invention can be selected from known photochromic moieties or substituents. While each photochromic moiety can be selected from inorganic photochromic moieties and organic photochromic moieties, they are each typically and independently selected from organic photochromic moieties.

With some embodiments, each photochromic moiety (PC), of the photochromic compounds of the present invention, is independently selected from, indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds, and mixtures thereof.

Non-limiting examples of photochromic pyrans from which the photochromic (PC) moiety, of the photochromic compounds of the present invention, can be chosen include benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference; spiro-9-fluoreno[1,2-b]pyrans; phenanthropyrans; quinopyrans; fluoroanthenopyrans; spiropyrans, e.g., spiro(benzindoline)naphthopyrans, spiro(indoline)benzopyrans, spiro(indoline)naphthopyrans, spiro(indoline)quinopyrans and spiro(indoline)pyrans. Further examples of naphthopyrans and complementary organic photochromic compounds are described in U.S. Pat. No. 5,658,501, which are hereby specifically incorporated by reference herein. Spiro(indoline)pyrans are also described in the text, *Techniques in Chemistry*, Volume III, "Photochromism", Chapter 3, Glenn H. Brown, Editor, John Wiley and Sons, Inc., New York, 1971, which is hereby incorporated by reference.

Non-limiting examples of photochromic oxazines from which each photochromic moiety (PC) can be independently chosen include benzoxazines, naphthoxazines, and spiro-oxazines, e.g., spiro(indoline)naphthoxazines, spiro(indoline)pyridobenzoxazines, spiro(benzindoline)pyridobenzoxazines, spiro(benzindoline)naphthoxazines, spiro(indoline)benzoxazines, spiro(indoline)fluoranthenoxazine, and spiro(indoline)quinoxazine. Non-limiting examples of photochromic fulgides from which each photochromic moiety (PC) can be independently chosen include: fulgimides, and the 3-furyl and 3-thienyl fulgides and fulgimides, which are disclosed in U.S. Pat. No. 4,931,220 (which are hereby specifically incorporated by reference) and mixtures of any of the aforementioned photochromic materials/compounds.

With some embodiments, each photochromic moiety of the photochromic compounds of the present invention are each independently selected from one or more indeno-fused naphthopyrans. As will be discussed in further detail herein, an indeno-fused naphthopyran typically has 10 to 12 available positions to which the divalent linking $L^2$ of Formula (I) can be bonded.

In accordance with some embodiments, each photochromic moiety (PC) is independently selected from an indeno-fused naphthopyran, which can be represented by the following general Formula (VIII), in which the ring atoms are numbered as shown,

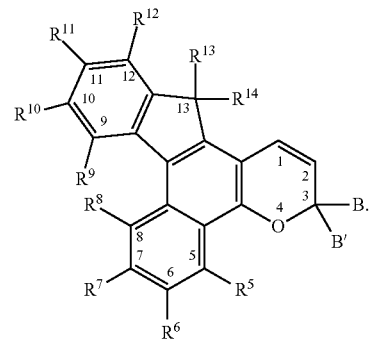

Formula (VIII)

The B and B' groups of the indeno-fused naphthopyran represented by general formula (VIII) are each independently selected, with some embodiments, from substituted and unsubstituted aromatic groups, and substituted and unsubstituted heteroaromatic groups, or B and B' taken together can form, with some embodiments, an unsubstituted or substituted fluoren-9-ylidene.

The indeno-fused naphthopyran represented by general formula (VIII) can be referred to as an indeno[2',3':3,4]naphtho[1,2-b]pyran. Each photochromic moiety (PC) can, with some embodiments, be independently selected from an indeno-naphthopyran, including, but not limited to, indeno[2',3':3,4]naphtho[1,2-b]pyrans represented by general formula (VIII), and/or one or more indeno[1',2':4,3]naphtho[2,1-b]pyrans represented by the following general Formula-(IX), in which the ring atoms are numbered as shown,

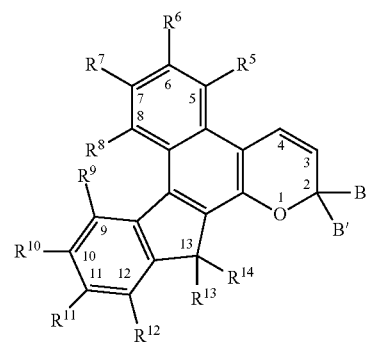

Formula (IX)

The $R^5$ through $R^{14}$, B and B' groups of the indeno[1',2':4,3]naphtho[2,1-b]pyran represented by general Formula-(IX) are each as described herein with regard to the indeno[2',3':3,4]naphtho[1,2-b]pyran represented by general Formula (VIII).

With some embodiments, each photochromic moiety (PC) is independently selected from an indeno[2',3':3,4]naphtho[1,2-b]pyran, such as represented by Formula (VIII), and/or an indeno[1',2':4,3]naphtho[2,1-b]pyran represented by general Formula (IX). In accordance with some further embodiments, each photochromic moiety (PC) is independently selected from an indeno[2',3':3,4]naphtho[1,2-b]pyran, such as represented by Formula (VIII).

When, as with some embodiments, each photochromic moiety (PC) is independently selected from an indeno[2',3':3,4]naphtho[1,2-b]pyran, such as represented by Formula (VIII), each such photochromic moiety (PC) can be independently bonded to $L^2$ at a ring position selected from ring position 3, ring position 6, ring position 7, ring position 11, and ring position 13.

When, as with some embodiments, each photochromic moiety (PC) is independently selected from an indeno[2',3':3,4]naphtho[1,2-b]pyran, such as represented by Formula (VIII), each such photochromic moiety (PC) can be independently bonded to $L^2$ at a ring position selected from ring position 3, ring position 11, and ring position 13.

In accordance with some embodiments, each photochromic moiety (PC) is selected from an indeno[2',3':3,4]naphtho[1,2-b]pyran, and each photochromic moiety (PC) is bonded to $L^2$ at ring position 3. In accordance with some further embodiments, each photochromic moiety (PC) is selected from an indeno[2',3':3,4]naphtho[1,2-b]pyran, and each photochromic moiety (PC) is bonded to $L^2$ at ring position 11. In accordance with some additional embodiments, each photochromic moiety (PC) is selected from an indeno[2',3':3,4]naphtho[1,2-b]pyran, and each photochromic moiety (PC) is bonded to $L^2$ at ring position 13.

Each photochromic moiety (PC) of the photochromic compounds of the present invention can, with some embodiments, be selected so as, in each case, to have an activated visible light absorbance spectra, and the activated visible light absorbance spectra of each photochromic moiety (PC) is substantially the same. The activated visible light absorbance of each photochromic moiety (PC) can be determined in accordance with art-recognized methods using art-recognized analytical equipment. In accordance with some embodiments, each photochromic moiety (PC): is selected from an indeno-fused naphthopyran, such as an indeno[2',3':3,4]naphtho[1,2-b]pyran, or an indeno[1',2':4,3]naphtho[2,1-b]pyran; has substantially the same structure; and is bonded to $L^2$ at the same ring position of each photochromic moiety (PC).

With the indeno-fused naphthopyrans as represented by general formulas (VIII) and/or (XI), $R^5$, $R^6$, $R^7$, $R^8$, $R^9$, $R^{10}$, $R^{11}$ and $R^{12}$ can each independently be selected in each case from: a reactive substituent; a compatiblizing substituent; hydrogen; fluoro; chloro; $C_1$-$C_6$ alkyl; $C_3$-$C_7$ cycloalkyl; substituted or unsubstituted phenyl; —$OR_{10}$' or —$OC(\!=\!O)R_{10}$', wherein $R_{10}$' is hydrogen, $C_1$-$C_6$ alkyl, phenyl($C_1$-$C_3$)alkyl, mono($C_1$-$C_6$)alkyl substituted phenyl($C_1$-$C_3$)alkyl, mono ($C_1$-$C_6$)alkoxy substituted phenyl($C_1$-$C_3$)alkyl, ($C_1$-$C_6$) alkoxy($C_2$-$C_4$)alkyl, $C_3$-$C_7$ cycloalkyl, or mono($C_1$-$C_4$)alkyl substituted $C_3$-$C_7$ cycloalkyl. The phenyl substituents (i.e., the substituents of the substituted phenyl) can be selected from hydroxyl, halogen, carbonyl, $C_1$-$C_6$ alkoxycarbonyl, cyano, halo($C_1$-$C_6$)alkyl, $C_1$-$C_6$ alkyl or $C_1$-$C_6$ alkoxy.

Alternatively or in addition to the previously recited classes and examples, $R^5$, $R^6$, $R^7$, $R^8$, $R^9$, $R^{10}$, $R^{11}$ and $R^{12}$ can each independently be selected in each case from: —$N(R_{11}$') $R_{12}$', wherein $R_{11}$' and $R_{12}$' are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}$' and $R_{12}$' come together with the nitrogen atom to form a $C_3$-$C_{20}$ hetero-bicycloalkyl ring or a $C_4$-$C_{20}$ hetero-tricycloalkyl ring.

Each $R^5$, $R^6$, $R^7$, $R^8$, $R^9$, $R^{10}$, $R^{11}$ and $R^{12}$ group can independently be selected in each case from, a nitrogen containing ring substituent represented by the following general (or graphic) Formula X:

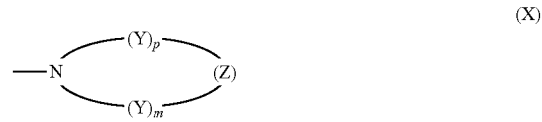

(X)

With the nitrogen ring substituent represented by general Formula X, each —Y— is independently chosen for each occurrence from —$CH_2$—, —$CH(R_{13}$')—, —$C(R_{13})_2$—, —CH(aryl)-, —C(aryl)$_2$-, and —$C(R_{13}$')(aryl)-, and Z is —Y—, —O—, —S—, —S(O)—, —$SO_2$—, —NH—, —$N(R_{13}$')—, or —N(aryl)-, wherein each $R_{13}$' is independently $C_1$-$C_6$ alkyl, each aryl is independently phenyl or naphthyl, m is an integer 1, 2 or 3, and p is an integer 0, 1, 2, or 3 and provided that when p is 0, Z is —Y—.

Additionally, each $R^5$, $R^6$, $R^7$, $R^8$, $R^9$, $R^{10}$, $R^{11}$ and $R^{12}$ can group independently be selected in each case from a nitrogen containing ring substituent represented by general formula (XB) and/or general formula (XC):

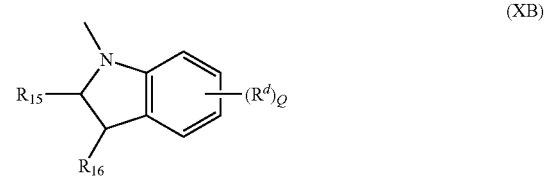

(XB)

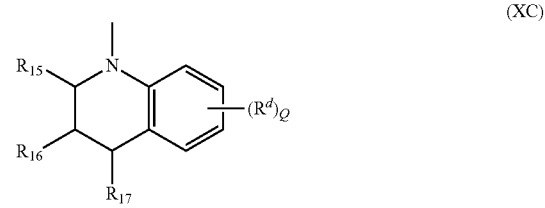

(XC)

For the nitrogen containing ring substituents represented by general formulas (XB) and (XC), $R_{15}$, $R_{16}$, and $R_{17}$ are each independently selected from hydrogen, $C_1$-$C_6$ alkyl, phenyl, or naphthyl, or the groups $R_{15}$ and $R_{16}$ together form a ring of 5 to 8 carbon atoms and each $R^d$ is independently for each occurrence selected from $C_1$-$C_6$ alkyl, $C_1$-$C_6$ alkoxy, fluoro or chloro, and Q is an integer 0, 1, 2, or 3.

Each $R^5$, $R^6$, $R^7$, $R^8$, $R^9$, $R^{10}$, $R^{11}$ and $R^{12}$ group can also independently be selected in each case from unsubstituted, mono-, or di-substituted $C_4$-$C_{18}$ spirobicyclic amine, or unsubstituted, mono-, and di-substituted $C_4$-$C_{18}$ spirotricyclic amine. The substituents of the spirobicyclic amines and the spirotricyclic amines can in each case be independently selected from aryl, $C_1$-$C_6$ alkyl, $C_1$-$C_6$ alkoxy, or phenyl($C_1$-$C_6$)alkyl.

With some embodiments, $R^6$ and $R^7$, of the indeno-fused naphthopyran, can together form a group represented by the following general Formula (XD) or general Formula (XE),

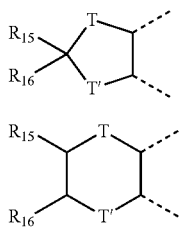

With the groups represented by general Formulas (XD) and (XE), T and T' are each independently oxygen or the group —NR$_{11}$—, where R$_{11}$, R$_{15}$, and R$_{16}$ are each as set forth and described previously herein.

The R$^{13}$ and R$^{14}$ groups of the indeno-fused naphthopyrans, such as the indeno[2',3':3,4]naphtho[1,2-b]pyran represented by general Formula (VIII), and/or the indeno[1',2':4,3]naphtho[2,1-b]pyran represented by general Formula (IX), can each be independently selected from: a reactive substituent; a compatiblizing substituent; hydrogen; hydroxy; C$_1$-C$_6$ alkyl; hydroxy(C$_1$-C$_6$)alkyl; C$_3$-C$_7$ cycloalkyl; allyl; substituted or unsubstituted phenyl; substituted or unsubstituted benzyl; chloro; fluoro; the group —C(=O)W', wherein W' is hydrogen, hydroxy, C$_1$-C$_6$ alkyl, C$_1$-C$_6$ alkoxy, the unsubstituted, mono- or di-substituted aryl groups phenyl or naphthyl, phenoxy, mono- or di-(C$_1$-C$_6$)alkoxy substituted phenoxy, mono- or di-(C$_1$-C$_6$)alkoxy substituted phenoxy, amino, mono(C$_1$-C$_6$)alkylamino, di(C$_1$-C$_6$)alkylamino, phenylamino, mono- or di-(C$_1$-C$_6$)alkyl substituted phenylamino, or mono- or di-(C$_1$-C$_6$)alkoxy substituted phenylamino. The phenyl, benzyl, or aryl group substituents (e.g., the substituents of the substituted phenyl, substituted benzyl and substituted aryl groups) are each independently selected from C$_1$-C$_6$ alkyl or C$_1$-C$_6$ alkoxy.

The R$^{13}$ and R$^{14}$ groups of the indeno-fused naphthopyran can each independently also be an —OR$_{18}$ group, in which R$_{18}$ is selected from C$_1$-C$_6$ alkyl, phenyl(C$_1$-C$_3$)alkyl, mono (C$_1$-C$_6$)alkyl substituted phenyl(C$_1$-C$_3$)alkyl, mono(C$_1$-C$_6$) alkoxy substituted phenyl(C$_1$-C$_3$)alkyl, C$_1$-C$_6$ alkoxy(C$_2$-C$_4$) alkyl, C$_3$-C$_7$ cycloalkyl, mono(C$_1$-C$_4$)alkyl substituted C$_3$-C$_7$ cycloalkyl, C$_1$-C$_6$ chloroalkyl, C$_1$-C$_6$ fluoroalkyl, allyl, or the group —CH(R$_{19}$)Y', wherein R$_{19}$ is hydrogen or C$_1$-C$_3$ alkyl and Y' is CN, CF$_3$, or COOR$_{20}$, wherein R$_{20}$ is hydrogen or C$_1$-C$_3$ alkyl, or R$_{18}$ is the group, —C(=O)W'', wherein W'' is hydrogen, C$_1$-C$_6$ alkyl, C$_1$-C$_6$ alkoxy, the unsubstituted, mono- or di-substituted aryl groups phenyl or naphthyl, phenoxy, mono-, or di-(C$_1$-C$_6$)alkyl substituted phenoxy, mono- or di-(C$_1$-C$_6$)alkoxy substituted phenoxy, amino, mono(C$_1$-C$_6$)alkylamino, di(C$_1$-C$_6$)alkylamino, phenylamino, mono- or di-(C$_1$-C$_6$)alkyl substituted phenylamino, or mono- or di-(C$_1$-C$_6$)alkoxy substituted phenylamino. The phenyl, benzyl, or aryl group substituents (e.g., the substituents of the substituted phenyl, substituted benzyl and substituted aryl groups) are each independently selected from C$_1$-C$_6$ alkyl or C$_1$-C$_6$ alkoxy.

The R$^{13}$ and R$^{14}$ groups of the indeno-fused naphthopyran can each independently also be a mono-substituted phenyl, in which the phenyl has a substituent located at the para position thereof. The substituent of the mono-substituted phenyl can be: a dicarboxylic acid residue or derivative thereof, a diamine residue or derivative thereof, an amino alcohol residue or derivative thereof, a polyol residue or derivative thereof, —CH$_2$—, —(CH$_2$)$_t$—, or —[O—(CH$_2$)$_t$]$_k$—, in which (t) is selected from an integer of 2, 3, 4, 5 or 6, and k is an integer selected from 1 to 50. The substituent of the mono-substituted phenyl is connected to an aryl group on another photochromic material.

Alternatively, R$^{13}$ and R$^{14}$ can together form an oxo group, a spiro-carbocyclic group containing 3 to 6 carbon atoms, or a spiro-heterocyclic group containing 1 to 2 oxygen atoms and 3 to 6 carbon atoms including the spirocarbon atom. The spiro-carbocyclic and spiro-heterocyclic groups are annellated with 0, 1 or 2 benzene rings.

The B and B' groups of the indeno-fused naphthopyran can each be independently selected from: a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is the reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl.

The phenyl, aryl and heteroaromatic substituents (i.e., the substituents of the substituted phenyl, aryl and heteroaromatic groups) of the B and B' groups can each be independently selected from: hydroxyl, a group —C(=O)R$_{21}$, wherein R$_{21}$ is —OR$_{22}$, —N(R$_{23}$)R$_{24}$, piperidino, or morpholino, wherein R$_{22}$ is allyl, C$_1$-C$_6$ alkyl, phenyl, mono(C$_1$-C$_6$)alkyl substituted phenyl, mono(C$_1$-C$_6$)alkoxy substituted phenyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl (C$_1$-C$_3$)alkyl, C$_1$-C$_6$ alkoxy(C$_2$-C$_4$)alkyl or C$_1$-C$_6$ haloalkyl, R$_{23}$ and R$_{24}$ are each independently C$_1$-C$_6$ alkyl, C$_6$-C$_7$ cycloalkyl, phenyl or substituted phenyl, the phenyl substituents being C$_1$-C$_6$ alkyl or C$_1$-C$_6$ alkoxy, and said halo substituent is chloro or fluoro, aryl, mono(C$_1$-C$_{12}$)alkoxyaryl, di(C$_1$-C$_{12}$)alkoxyaryl, mono(C$_1$-C$_{12}$)alkylaryl, di(C$_1$-C$_{12}$) alkylaryl, haloaryl, C$_3$-C$_7$ cycloalkylaryl, C$_3$-C$_7$ cycloalkyl, C$_3$-C$_7$ cycloalkyloxy, C$_3$-C$_7$ cycloalkyloxy(C$_1$-C$_{12}$)alkyl, C$_3$-C$_7$ cycloalkyloxy(C$_1$-C$_{12}$)alkoxy, aryl(C$_1$-C$_{12}$)alkyl, aryl (C$_1$-C$_{12}$)alkoxy, aryloxy, aryloxy(C$_1$-C$_{12}$)alkyl, aryloxy(C$_1$-C$_{12}$)alkoxy, mono- or di(C$_1$-C$_{12}$)alkylaryl(C$_1$-C$_{12}$)alkyl, mono- or di-(C$_1$-C$_{12}$)alkoxyaryl(C$_1$-C$_{12}$)alkyl, mono- or di-(C$_1$-C$_{12}$)alkylaryl(C$_1$-C$_{12}$)alkoxy, mono- or di-(C$_1$-C$_{12}$) alkoxyaryl(C$_1$-C$_{12}$)alkoxy, amino, mono- or di-(C$_1$-C$_{12}$) alkylamino, diarylamino, piperazino, N—(C$_1$-C$_{12}$) alkylpiperazino, N-arylpiperazino, aziridino, indolino, piperidino, morpholino, thiomorpholino, tetrahydroquinolino, tetrahydroisoquinolino, pyrrolidyl, C$_1$-C$_{12}$ alkyl, C$_1$-C$_{12}$ haloalkyl, C$_1$-C$_{12}$ alkoxy, mono(C$_1$-C$_{12}$)alkoxy(C$_1$-C$_{12}$)alkyl, acryloxy, methacryloxy, or halogen.

The B and B' groups can also each independently be an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl. The substituents of these mono-substituted groups can each independently selected from C$_1$-C$_{12}$ alkyl, C$_1$-C$_{12}$ alkoxy, phenyl, or halogen.

In addition, the B and B' groups can each be independently selected from a group represented by the following general Formulas (XIA) or (XIB),

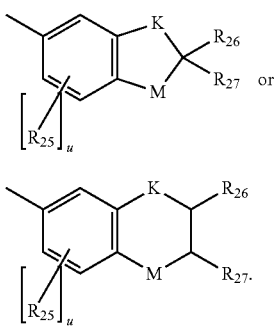

Independently with each of general formulas (XIA) and (XIB), K is —CH$_2$— or —O—, and M is —O— or substituted nitrogen, provided that when M is substituted nitrogen, K is —CH$_2$—. The substituted nitrogen substituents are hydrogen, C$_1$-C$_{12}$ alkyl, or C$_1$-C$_{12}$ acyl. Each R$_{25}$ is independently selected for each occurrence from C$_1$-C$_{12}$ alkyl, C$_1$-C$_{12}$ alkoxy, hydroxy, and halogen, and each u is independently an integer ranging from 0 to 2. The R$_{26}$ and R$_{27}$ groups are each independently hydrogen or C$_1$-C$_{12}$ alkyl.

Each B and B' group can independently be a group represented by the following general Formula (XII),

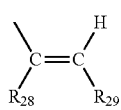

With the group represented by general Formula (XII), R$_{28}$ is hydrogen or C$_1$-C$_{12}$ alkyl, and R$_{29}$ is an unsubstituted, mono- or di-substituted group chosen from naphthyl, phenyl, furanyl, and thienyl. The substitutents of the mono- or di-substituted naphthyls, phenyls, furanyls, and thienyls, are in each case independently selected from C$_1$-C$_{12}$ alkyl, C$_1$-C$_{12}$ alkoxy, or halogen.

The B and B' groups can together form a member selected from, a fluoren-9-ylidene, a mono-substituted fluoren-9-ylidene, or a di-substituted fluoren-9-ylidene. The substituents of the mono-substituted fluoren-9-ylidene, and the di-substituted fluoren-9-ylidene can in each case be independently selected from C$_1$-C$_{12}$ alkyl, C$_1$-C$_{12}$ alkoxy, or halogen.

In accordance with some embodiments of the present invention, each photochromic moiety (PC) is selected from an indeno[2',3':3,4]naphtho[1,2-b]pyran represented by Formula (VIII), each photochromic moiety is bonded to L$^2$ at ring position 3, and B' is selected from

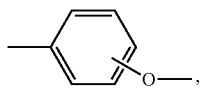

in which L$^2$ is bonded to the oxygen.

In accordance with some embodiments of the present invention, each photochromic moiety (PC) is selected from an indeno[2',3':3,4]naphtho[1,2-b]pyran represented by Formula (VIII) and: each photochromic moiety is bonded to L$^2$ at ring position 3; R$^{13}$ and R$^{14}$ are each independently selected from linear or branched C$_1$-C$_6$ alkyl, such as methyl; R$^5$ through R$^{12}$ are each hydrogen; B is selected from phenyl and linear or branched C$_1$-C$_6$ alkoxy substituted phenyl, such as methoxy substituted phenyl; and B' is selected from

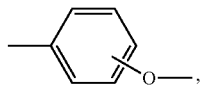

in which L$^2$ is bonded to the oxygen of B'.

In accordance with some further embodiments of the present invention, each photochromic moiety (PC) is selected from an indeno[2',3':3,4]naphtho[1,2-b]pyran represented by Formula (VIII), each photochromic moiety is bonded to L$^2$ at ring position 13, R$^{14}$ is —O—, and L$^2$ is bonded to R$^{14}$.

In accordance with some further embodiments of the present invention, each photochromic moiety (PC) is selected from an indeno[2',3':3,4]naphtho[1,2-b]pyran represented by Formula (VIII) and: each photochromic moiety is bonded to L$^2$ at ring position 13; B and B' are each independently selected from phenyl and linear or branched C$_1$-C$_6$ alkoxy substituted phenyl, such as methoxy substituted phenyl; R$^6$ and R$^{11}$ are each independently selected from linear or branched C$_1$-C$_6$ alkoxy, such as methoxy; R$^5$, R$^7$, R$^8$, R$^9$ and R$^{19}$ are each hydrogen; R$^{13}$ is linear or branched C$_1$-C$_6$ alkyl, such as n-butyl; and R$^{14}$ is —O—, in which L$^2$ is bonded to R$^{14}$.

In accordance with some further embodiments of the present invention, each photochromic moiety (PC) is selected from an indeno[2',3':3,4]naphtho[1,2-b]pyran represented by Formula (VIII), each photochromic moiety is bonded to L$^2$ at ring position 11, R$^{11}$ is selected from

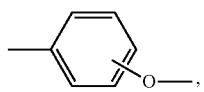

and L$^2$ is bonded to the oxygen of R$^{11}$.

In accordance with some further embodiments of the present invention, each photochromic moiety (PC) is selected from an indeno[2',3':3,4]naphtho[1,2-b]pyran represented by Formula (VIII) and: each photochromic moiety is bonded to L$^2$ at ring position 11; R$^{13}$ and R$^{14}$ are each independently selected from linear or branched C$_1$-C$_6$ alkyl, such as methyl; R$^6$ and R$^7$ are each independently selected from linear or branched C$_1$-C$_6$ alkoxy, such as methoxy; R$^5$, R$^8$, R$^9$, R$^{10}$ and R$^{12}$ are each hydrogen; B is phenylmorpholine; B' is selected from phenyl and linear or branched C$_1$-C$_6$ alkoxy substituted phenyl, such as methoxy substituted phenyl; and R$^{11}$ is selected from

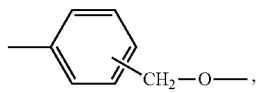

in which L$^2$ is bonded to the oxygen of R$^{11}$.

As previously discussed, the indeno-fused naphthopyrans from which each photochromic moiety (PC) can be independently selected, can include at least one of a reactive substituent and/or a compatibilizing substituent. Any one or more of the groups R$^5$ through R$^{14}$, B and B' of the indeno-fused naphthopyran (e.g., represented by general formulas-VIII and/or -IX) can include at least one of a reactive substituent and/or a compatibilizing substituent. If the photochromic moiety includes multiple reactive substituents and/or multiple compatibilizing substituents, each reactive substituent and each compatibilizing substituent can be independently chosen.

The reactive substituent and the compatibilizing substituent can each independently be represented in each case by one of:

-A'-D-E-G-J (XIII);
-A'-D-J (XIV);
-A'-G-J (XV);
-G-E-G-J (XVI);
-D-G-J (XVII);
-G-J (XVIII); and
-D-E-G-J (XIX);
-D-J (XX);
-A'-J (XXI).

With formulas (XIII) through (XXI), non-limiting examples of groups that -A'- can represent according to various non-limiting embodiments disclosed herein include —O—, —C(=O)—, —CH$_2$—, —OC(=O)— and —NHC(=O)—, provided that if -A'- represents —O—, -A'- forms at least one bond with -J.

Non-limiting examples of groups that -D- can represent according to various non-limiting embodiments include a diamine residue or a derivative thereof, wherein a first amino nitrogen of said diamine residue can form a bond with -A'-, or a substituent or an available position on the indeno-fused naphthopyran, and a second amino nitrogen of said diamine residue can form a bond with -E-, -G- or -J; and an amino alcohol residue or a derivative thereof, wherein an amino nitrogen of said amino alcohol residue can form a bond with -A'-, or a substituent or an available position on the indeno-fused naphthopyran, and an alcohol oxygen of said amino alcohol residue can form a bond with -E-, -G- or -J. Alternatively, according to various non-limiting embodiments disclosed herein the amino nitrogen of said amino alcohol residue can form a bond with -E-, -G- or -J, and said alcohol oxygen of said amino alcohol residue can form a bond with -A'-, or a substituent or an available position on the indeno-fused naphthopyran.

Non-limiting examples of suitable diamine residues that -D- can represent include an aliphatic diamine residue, a cyclo aliphatic diamine residue, a diazacycloalkane residue, an azacyclo aliphatic amine residue, a diazacrown ether residue, and an aromatic diamine residue. More particular, illustrative and non-limiting examples of diamine residues that can be used in conjunction with various non-limiting embodiments disclosed herein include the following:

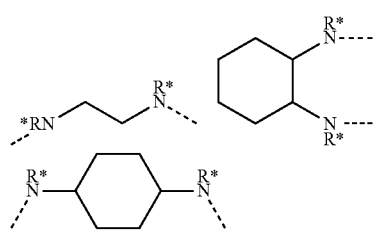

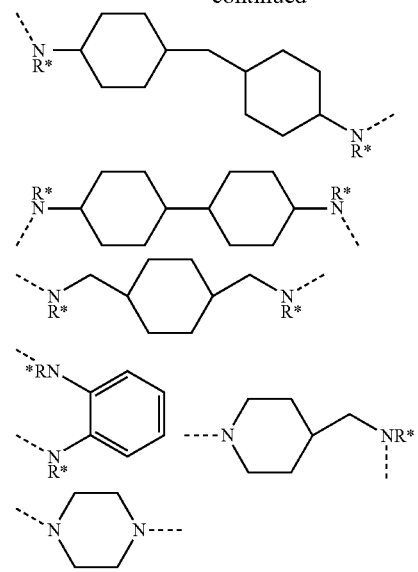

R* = H or alkyl

Non-limiting examples of suitable amino alcohol residues that -D- can represent include an aliphatic amino alcohol residue, a cyclo aliphatic amino alcohol residue, an azacyclo aliphatic alcohol residue, a diazacyclo aliphatic alcohol residue and an aromatic amino alcohol residue. More particular, illustrative and non-limiting examples of amino alcohol residues that can be used in conjunction with various non-limiting embodiments disclosed herein include the following:

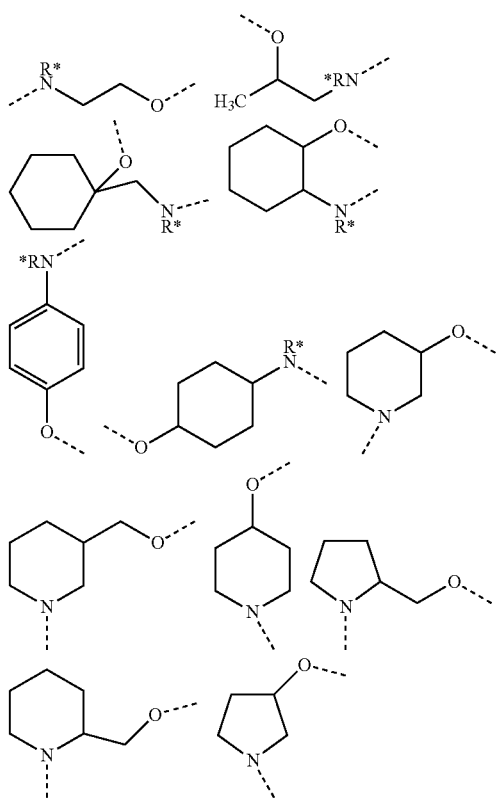

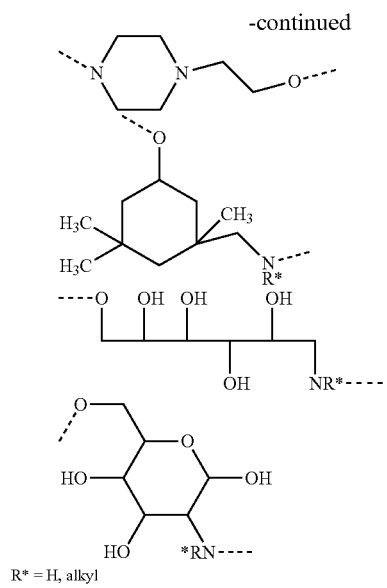

R* = H, alkyl

With continued reference to formulas (XIII) through (XXI) above, according to various non-limiting embodiments disclosed herein, -E- can represent a dicarboxylic acid residue or a derivative thereof, wherein a first carbonyl group of said dicarboxylic acid residue can form a bond with -G- or -D-, and a second carbonyl group of said dicarboxylic acid residue can form a bond with -G-. Non-limiting examples of suitable dicarboxylic acid residues that -E- can represent include an aliphatic dicarboxylic acid residue, a cycloaliphatic dicarboxylic acid residue and an aromatic dicarboxylic acid residue. More particular, illustrative and non-limiting examples of dicarboxylic acid residues that can be used in conjunction with various non-limiting embodiments disclosed herein include the following:

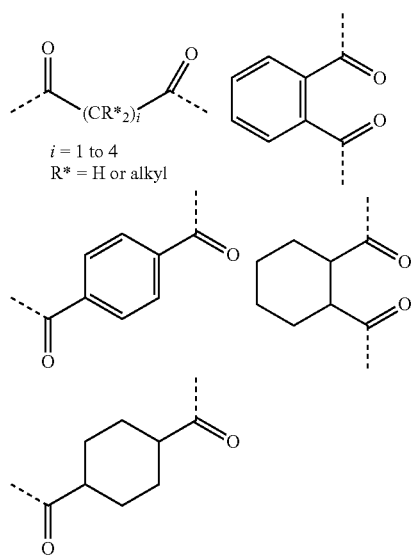

$i = 1$ to $4$
R* = H or alkyl

According to various non-limiting embodiments disclosed herein, -G- can represent a group represented by the following general formula,

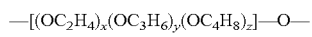

—[(OC$_2$H$_4$)$_x$(OC$_3$H$_6$)$_y$(OC$_4$H$_8$)$_z$]—O— in which x, y and z are each independently chosen and range from 0 to 50, and a sum of x, y, and z ranges from 1 to 50; a polyol residue or a derivative thereof, wherein a first polyol oxygen of said polyol residue can form a bond with -A$^1$-, -D-, -E-, or a substituent or an available position on the indeno-fused naphthopyran, and a second polyol oxygen of said polyol can form a bond with -E- or -J; or a combination thereof, wherein the first polyol oxygen of the polyol residue forms a bond with a group —[(OC$_2$H$_4$)$_x$(OC$_3$H$_6$)$_y$(OC$_4$H$_8$)$_z$]— (i.e., to form the group —[(OC$_2$H$_4$)$_x$(OC$_3$H$_6$)$_y$(OC$_4$H$_8$)$_z$]—O—), and the second polyol oxygen forms a bond with -E- or -J. Non-limiting examples of suitable polyol residues that -G- can represent include an aliphatic polyol residue, a cyclo aliphatic polyol residue and an aromatic polyol residue.

More particular, illustrative and non-limiting examples of polyols from which the polyol residues that -G- can represent can be formed according to various non-limiting embodiments disclosed herein include (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

With further reference to formulas (XIII) through (XXI), according to various non-limiting embodiments disclosed herein, -J can represent a group —K, wherein —K represents a group such as, but not limited to, —CH$_2$COOH, —CH(CH$_3$)COOH, —C(O)(CH$_2$)$_w$COOH, —C$_6$H$_4$SO$_3$H, —C$_5$H$_{10}$SO$_3$H, —C$_4$H$_8$SO$_3$H, —C$_3$H$_6$SO$_3$H, —C$_2$H$_4$SO$_3$H and —SO$_3$H, wherein "w" ranges from 1 to 18. According to other non-limiting embodiments -J can represent hydrogen that forms a bond with an oxygen or a nitrogen of linking group to form a reactive moiety such as —OH or —NH. For example, according to various non-limiting embodiments disclosed herein, -J can represent hydrogen, provided that if -J represents hydrogen, -J is bonded to an oxygen of -D- or -G-, or a nitrogen of -D-.

According to still further non-limiting embodiments, -J can represent a group -L or residue thereof, wherein -L can represent a reactive moiety. For example, according to various non-limiting embodiments disclosed herein -L can represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

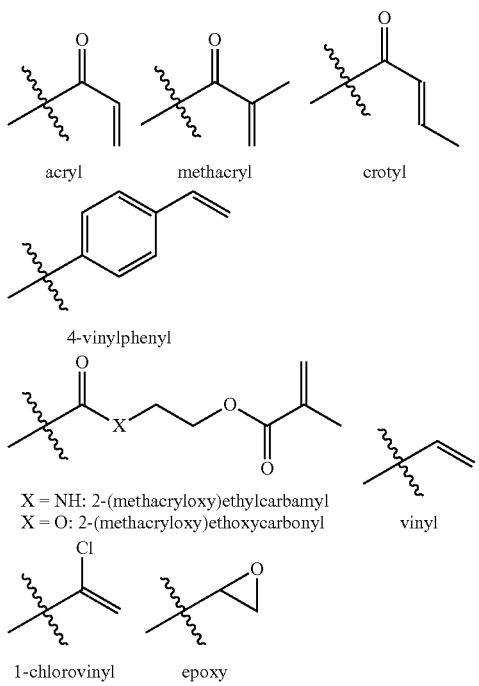

As previously discussed, -G- can represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue can be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol can be represented by $q\text{-}(OH)_a$ and the residue of the polyol can be represented by the formula $-O\text{-}q\text{-}(OH)_{a-1}$, wherein q is the backbone or main chain of the polyhydroxy compound and "a" is at least 2.

Further, as discussed above, one or more of the polyol oxygens of -G- can form a bond with -J (i.e., forming the group -G-J). For example, although not limiting herein, wherein the reactive and/or compatiblizing substituent comprises the group -G-J, if -G- represents a polyol residue and -J represents a group —K that contains a carboxyl terminating group, -G-J can be produced by reacting one or more polyol hydroxyl groups to form the group —K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group —K that contains a sulfo or sulfono terminating group, although not limiting herein, -G-J can be produced by acidic condensation of one or more of the polyol hydroxyl groups with $HOC_6H_4SO_3H$; $HOC_5H_{10}SO_3H$; $HOC_4H_8SO_3H$; $HOC_3H_6SO_3H$; $HOC_2H_4SO_3H$; or $H_2SO_4$, respectively. Further, although not limiting herein, if -G- represents a polyol residue and -J represents a group -L chosen from acryl, methacryl, 2-(methacryloxy)ethylcarbamyl and epoxy, -L can be added by condensation of the polyol residue with acryloyl chloride, methacryloyl chloride, 2-isocyanatoethyl methacrylate or epichlorohydrin, respectively.

In accordance with some embodiments, -J of one or more of Formulas (XIII) through (XXI) is bonded to $L^2$ of Formula (I), in which case -J is a divalent linking group represented by -J-. With some embodiments, when bonded to $L^2$ of Formula (I), examples of divalent -J- include, but are not limited to: —O—; —S—; —NR*— where R* is hydrogen or hydrocarbyl, such as, linear or branched $C_1$-$C_{20}$ alkyl, $C_3$-$C_{12}$ cycloalkyl, $C_3$-$C_{12}$ heterocycloalkyl, aryl, and heteroaryl; —$CH_2COO$—; —$CH(CH_3)COO$—; —$C(O)(CH_2)_w COO$—, where "w" is from 1 to 18; —$C_6H_4SO_3$—; —$C_6H_{10}SO_3$—; —$C_4H_6SO_3$—; —$C_3H_6SO_3$—; —$C_2H_4SO_3$—; —$SO_3$—; and combinations of two or more thereof.

Indeno-fused naphthopyrans from which each photochromic moieties (PC) can be independently selected can be prepared by art-recognized methods. With some embodiments, the indeno-fused naphthopyrans, from which each photochromic moieties (PC) can be independently selected, can be synthesized in accordance with the description provided in U.S. Pat. No. 6,296,785, at column 10, line 52 through column 29, line 18, which disclosure is incorporated herein by reference. With some further embodiments, the indeno-fused naphthopyrans, from which each photochromic moieties (PC) can be independently selected, can be synthesized in accordance with the description provided in U.S. Pat. No. 7,527,754 B2 at column 13, line 52 through column 14, line 62, which disclosure is incorporated herein by reference. With some additional further embodiments, the indeno-fused naphthopyrans, from which each photochromic moieties (PC) can be independently selected, can be synthesized in accordance with the description provided in U.S. Pat. No. 5,645,767, at column 5, line 6 through column 11, line 31, which disclosure is incorporated herein by reference.

The photochromic compounds of the present invention can each be used alone, or in combination with other photochromic compounds according to various non-limiting embodiments disclosed herein, or in combination with one or more appropriate complementary conventional photochromic compounds. For example, the photochromic compounds of the present invention can be used in conjunction with conventional photochromic compounds having activated absorption maxima within the range of 300 to 1000 nanometers. Further, the photochromic compounds according to the present invention can be used in conjunction with a complementary conventional polymerizable or a compatiblized photochromic compound, such as for example, those disclosed in U.S. Pat. No. 6,113,814 (at col. 2, line 39 to col. 8, line 41), and U.S. Pat. No. 6,555,028 (at col. 2, line 65 to col. 12, line 56), which disclosures are hereby specifically incorporated by reference herein.

The photochromic compounds of the present invention can be used in combination with a mixture of other photochromic compounds. For example, although not limiting herein, mixtures of photochromic compounds can be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

The present invention also relates to a photochromic article that include one or more photochromic compounds according to the present invention, such as represented by Formulas (I) and (II).

In accordance with further embodiments of the present invention, the photochromic articles of the present invention can be selected from ophthalmic articles or elements, display articles or elements, windows, mirrors, packaging material such as shrinkwrap, and active and passive liquid crystal cell articles or elements.

Examples of ophthalmic articles or elements include, but are not limited to, corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

Examples of display articles, elements and devices include, but are not limited to, screens, monitors, and security elements, including without limitation, security marks and authentication marks.

Examples of windows include, but are not limited to, automotive and aircraft transparencies, filters, shutters, and optical switches.

With some embodiments, the photochromic article can be a security element. Examples of security elements include, but are not limited to, security marks and authentication marks that are connected to at least a portion of a substrate, such as: access cards and passes, e.g., tickets, badges, identification or membership cards, debit cards, etc.; negotiable instruments and non-negotiable instruments e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

With further embodiments, the security element can be connected to at least a portion of a substrate chosen from a transparent substrate and a reflective substrate. Alternatively, according to further embodiments in which a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Additionally or alternatively, the security element can be connected to at least a portion of a substrate chosen from untinted substrates, tinted substrates, photochromic substrates, tinted-photochromic substrates, linearly polarizing, circularly polarizing substrates, and elliptically polarizing substrates.

Furthermore, security elements according to the aforementioned embodiments can further include one or more other coatings or films or sheets to form a multi-layer reflective security element with viewing angle dependent characteristics, such as described in U.S. Pat. No. 6,641,874.

Photochromic articles according to the present invention, such as optical elements, can include a substrate and a photochromic material that includes the photochromic compound according to the present invention, in which the photochromic material is connected to at least a portion of the substrate. As used herein, the term "connected to" means associated with, either directly, or indirectly by means of another material or structure.

Photochromic articles according to the present invention can include, as discussed above, a substrate that can include one or more polymeric compounds of the present invention. The photochromic compounds of the present invention can be incorporated into at least a portion of the polymeric material of the substrate; or by incorporating the photochromic compound(s) into at least a portion of the oligomeric or monomeric material from which the substrate is formed. For example, according to one non-limiting embodiment, the photochromic compound can be incorporated into the polymeric material of the substrate by a cast-in-place method or by imbibition. The imbibition and the cast-in-place methods are discussed in further detail herein below.

In the imbibition method, the photochromic compound is typically diffused into the polymeric material of a previously formed or fabricated article, such as a substrate or previously applied coating/film. Imbibition can be performed by immersing the polymeric material of a previously formed or fabricated article in a solution containing the photochromic compound, with or without heating. Thereafter, although not required, the photochromic compound can be bonded with the polymeric material (e.g., of the substrate or coating).

With cast-in-place methods, the photochromic compound(s) can be mixed with: a polymer and/or oligomer composition in solution or melt form; or monomer composition in liquid form, so as to form a castable photochromic composition. The castable photochromic composition is then typically introduced into the cavity of a mold (e.g., a lens mold). The castable photochromic composition is then set within the mold so as to form a photochromic article.

With photochromic articles according to the present invention that include a substrate, a photochromic compound(s) can be included in a coating that is connected to at least a portion of the substrate. The substrate can be a polymeric substrate or an inorganic substrate (such as, but not limited to, a glass substrate). The photochromic compound(s) can be incorporated into at least a portion of a coating composition prior to application of the coating composition to the substrate. Alternatively, a coating composition can be applied to the substrate, at least partially set, and thereafter the photochromic compound(s) can be imbibed into at least a portion of the coating. As used herein, the terms "set" and "setting" include, without limitation, curing, polymerizing, cross-linking, cooling, and drying.

Photochromic articles according to the present invention can be formed by art-recognized in-mold coating (or in-mold casting) methods. With in-mold coating methods, a photochromic coating composition that includes a photochromic compound(s) of the present invention, which can be a liquid coating composition or a powder coating composition, is applied to at least a portion of the interior surface of a mold, and then at least partially set. Thereafter, a polymer solution or melt, or oligomeric or monomeric solution or mixture is cast or molded within the mold cavity and in contact with the previously applied photochromic coating composition, and at least partially set. The resulting photochromic article is then removed from the mold. Non-limiting examples of powder coatings in which the photochromic materials according to various non-limiting embodiments disclosed herein can be employed are set forth in U.S. Pat. No. 6,068,797 at col. 7, line 50 to col. 19, line 42, which disclosure is hereby specifically incorporated by reference herein.

Photochromic articles according to the present invention can also be formed by art-recognized over-mold methods.

Over-mold methods typically involve forming a substrate within a mold, and then forming an interior space between the substrate and an interior surface of the mold, into which a photochromic coating composition is then subsequently introduced (e.g., injected) and then set (e.g., cured). Alternatively, over-mold methods can involve introducing a previously formed substrate into a mold, such that an interior space is defined between the substrate and an interior mold surface, and thereafter a photochromic coating composition is introduced (e.g., injected) into the interior space. The photochromic coating compositions include one or more photochromic compounds of the present invention.

Photochromic articles according to the present invention can also be formed by means of art-recognized lamination methods. With lamination methods, a film comprising the photochromic compound(s) according to the present invention can be adhered or otherwise connect to a portion of the substrate, with or without an adhesive and/or the application of heat and pressure. Thereafter, if desired, a second substrate can be applied over the first substrate and the two substrates can be laminated together (i.e., by the application of heat and pressure) to form an element wherein the film comprising the photochromic compound is interposed between the two substrates. Methods of forming films comprising the photochromic compounds of the present invention can include for example and without limitation, combining a photochromic compound with a polymeric solution or oligomeric solution or mixture, casting or extruding a film therefrom, and, if required, at least partially setting the film. Additionally or alternatively, a film can be formed (with or without a photochromic compound) and imbibed with the photochromic compound.

Coating compositions that include the photochromic compound(s) of the present invention can be connected to at least a portion of the substrate of the photochromic article by art-recognized methods, such as applying a coating composition that includes the photochromic compound(s) to at least a portion of a surface of the substrate, and at least partially setting the coating composition. Additionally or alternatively, the coating that includes the photochromic compound(s) can be connected to the substrate, for example, through one or more additional coatings. For example, while not limiting herein, according to various non-limiting embodiments, an additional coating composition can be applied to a portion of the surface of the substrate, at least partially set, and thereafter the coating composition that includes the photochromic compound(s) can be applied over the additional coating and at least partially set. Non-limiting and art-recognized methods of applying coatings compositions to substrates are discussed herein below.

Examples of additional coatings and films that can be used in conjunction with the photochromic coatings and articles according to the present invention, include, but are not limited to: primer coatings and films (which typically reside under the photochromic coating); protective coatings and films (which are typically applied over the photochromic coating), including transitional coatings and films and abrasion resistant coatings and films; anti-reflective coatings and films; conventional photochromic coatings and films; polarizing coatings and films; and combinations thereof. As used herein the term "protective coating or film" refers to coatings or films that can prevent wear or abrasion, provide a transition in properties from one coating or film to another, protect against the effects of polymerization reaction chemicals and/or protect against deterioration due to environmental conditions such as moisture, heat, ultraviolet light, oxygen, etc.

As used herein, the term "transitional coating and film" means a coating or film that aids in creating a gradient in properties between two coatings or films, or a coating and a film. For example, although not limiting herein, a transitional coating can aid in creating a gradient in hardness between a relatively hard coating and a relatively soft coating. Non-limiting examples of transitional coatings include radiation-cured, acrylate-based thin films as described in U.S. Patent Application Publication 2003/0165686 at paragraphs 79-173, which are hereby specifically incorporated by reference herein.

As used herein the term "abrasion resistant coating and film" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion resistant coatings include, for example, abrasion-resistant coatings comprising organosilanes, organosiloxanes, abrasion-resistant coatings based on inorganic materials such as silica, titania and/or zirconia, organic abrasion-resistant coatings of the type that are ultraviolet light curable, oxygen barrier-coatings, UV-shielding coatings, and combinations thereof.

Non-limiting examples of antireflective coatings and films include a monolayer, multilayer or film of metal oxides, metal fluorides, or other such materials, which can be deposited onto the articles disclosed herein (or onto films that are applied to the articles), for example, through vacuum deposition, sputtering, etc. Non-limiting examples of conventional photochromic coatings and films include, but are not limited to, coatings and films comprising conventional photochromic materials. Non-limiting examples of polarizing coatings and films include, but are not limited to, coatings and films comprising dichroic compounds that are known in the art.

Additional coating compositions (e.g., primers and overcoats) that can be used with photochromic coating compositions according to the present invention and/or to form photochromic articles according to the present invention, can be applied to/formed: on a substrate prior to application of the photochromic coating; and/or over a previously applied photochromic coating. For example, a primer coating can be formed on the substrate prior to applying a photochromic coating composition according to the present invention. Additionally or alternatively, an additional coating or film can be applied (e.g., as an over-coat or over-coating) at least partially over a previously applied photochromic coating composition according to the present invention. For example, a transitional coating can be formed over a previously applied photochromic coating composition according to the present invention, and an abrasion resistant coating can then be applied over the transitional coating.

Photochromic coating compositions according to the present invention include: a photochromic compound according to the present invention, such as described previously herein with reference to Formulas (I) and (II); a curable resin composition; and optionally a solvent. The photochromic coating composition can be in the form of art-recognized liquid coatings and powder coatings. The photochromic coating compositions of the present invention can be thermoplastic or thermosetting coating compositions. In an embodiment, the photochromic coating composition is a curable or thermosetting coating composition.

The curable resin composition of the curable photochromic coating compositions according to the present invention typically include: a first reactant (or component) having functional groups, e.g., an epoxide functional polymer reactant; and a second reactant (or component) that is a crosslinking agent having functional groups that are reactive towards and that can form covalent bonds with the functional groups of the first reactant. The first and second reactants of the curable resin composition of the curable photochromic coating composition can each independently include one or more functional species, and are each present in amounts sufficient to provide cured photochromic coatings having a desirable combination of physical properties, e.g., smoothness, optical clarity, solvent resistance and hardness.

Examples of curable resin compositions that can be used with the curable photochromic coating compositions according to the present invention include, but are not limited to: curable resin compositions comprising epoxide functional polymer (e.g., (meth)acrylic polymers containing residues of glycidyl (meth)acrylate and epoxide reactive crosslinking agent (e.g., containing active hydrogens, such as hydroxyls, thiols and amines); and curable resin compositions comprising hydroxy functional polymer and capped (or blocked) isocyanate functional crosslinking agent.

In an embodiment, the curable resin composition of the photochromic coating composition of the present invention is a curable urethane (or polyurethane) resin composition. Curable urethane resin compositions useful in the photochromic coating compositions of the present invention typically include: an active hydrogen functional polymer, such as a hydroxy functional polymer; and a capped (or blocked) isocyanate functional crosslinking agent. Hydroxy functional polymers that can be used in such compositions include, but are not limited to, art-recognized hydroxy functional vinyl polymers, hydroxy functional polyesters, hydroxy functional polyurethanes and mixtures thereof.

Vinyl polymers having hydroxy functionality can be prepared by free radical polymerization methods that are known to those of ordinary skill in the art. In an embodiment of the present invention, the hydroxy functional vinyl polymer is prepared from a majority of (meth)acrylate monomers and is referred to herein as a "hydroxy functional (meth)acrylic polymer."

Hydroxy functional polyesters useful in curable photochromic coating compositions comprising capped isocyanate functional crosslinking agent can be prepared by art-recognized methods. Typically, diols and dicarboxylic acids or diesters of dicarboxylic acids are reacted in a proportion such that the molar equivalents of hydroxy groups is greater than that of carboxylic acid groups (or esters of carboxylic acid groups) with the concurrent removal of water or alcohols from the reaction medium.

Hydroxy functional urethanes can be prepared by art-recognized methods, for example, as previously described herein. Typically one or more difunctional isocyanates are reacted with one or more materials having two active hydrogen groups (e.g., diols or dithiols), such that the ratio of active hydrogen groups to isocyanate groups is greater than 1, as is known to the skilled artisan.

By "capped (or blocked) isocyanate crosslinking agent" is meant a crosslinking agent having two or more capped isocyanate groups that can decap (or deblock) under cure conditions, e.g., at elevated temperature, to form free isocyanate groups and free capping groups. The free isocyanate groups formed by decapping of the crosslinking agent are preferably capable of reacting and forming substantially permanent covalent bonds with the active hydrogen groups of the active hydrogen functional polymer (e.g., with the hydroxy groups of a hydroxy functional polymer).

It is desirable that the capping group of the capped isocyanate crosslinking agent not adversely affect the curable photochromic coating composition upon decapping from the isocyanate (i.e., when it becomes a free capping group). For example, it is desirable that the free capping group neither become trapped in the cured film as gas bubbles nor excessively plasticize the cured film. Capping groups useful in the present invention preferably have the characteristics of being nonfugitive or capable of escaping substantially from the forming coating prior to its vitrification. Typically, the free capping groups escape substantially from the forming (e.g., curing) coating prior to its vitrification.

Classes of capping groups of the capped isocyanate crosslinking agent can be selected from: hydroxy functional compounds, e.g., linear or branched $C_2$-$C_8$ alcohols, ethylene glycol butyl ether, phenol and p-hydroxy methylbenzoate; 1H-azoles, e.g., 1H-1,2,4-triazole and 1H-2,5-dimethylpyrazole; lactams, e.g., $\epsilon$-caprolactam and 2-pyrrolidinone; ketoximes, e.g., 2-propanone oxime and 2-butanone oxime. Other suitable capping groups include, morpholine, 3-aminopropyl morpholine and N-hydroxy phthalimide.

The isocyanate or mixture of isocyanates of the capped isocyanate crosslinking agent has two or more isocyanate groups (e.g., 3 or 4 isocyanate groups). Examples of suitable isocyanates that can be used to prepare the capped isocyanate crosslinking agent include, monomeric diisocyanates, e.g., $\alpha,\alpha'$-xylylene diisocyanate, $\alpha,\alpha,\alpha',\alpha'$-tetramethylxylylene diisocyanate and 1-isocyanato-3-isocyanatomethyl-3,5,5-trimethylcyclohexane (isophorone diisocyanate or IPDI), and dimers and trimers of monomeric diisocyanates containing isocyanurate, uretidino, biruet or allophanate linkages, e.g., the trimer of IPDI.

The capped isocyanate crosslinking agent can also be selected from oligomeric capped isocyanate functional adducts. As used herein, by "oligomeric capped polyisocyanate functional adduct" is meant a material that is substantially free of polymeric chain extension. Oligomeric capped polyisocyanate functional adducts can be prepared by art-recognized methods from, for example, a compound containing three or more active hydrogen groups, e.g., trimethylolpropane (TMP), and an isocyanate monomer, e.g., 1-isocyanato-3,3,5-trimethyl-5-isocyanatomethylcyclohexane (IPDI), in a molar ratio of 1:3, respectively. In the case of TMP and IPDI, by employing art-recognized starved feed and/or dilute solution synthesis techniques, an oligomeric adduct having an average isocyanate functionality of 3 can be prepared (e.g., "TMP-3IPDI"). The three free isocyanate groups per TMP-3IPDI adduct are then capped with a capping group, e.g., a linear or branched $C_2$-$C_8$ alcohol.

To catalyze the reaction between the isocyanate groups of the capped polyisocyanate crosslinking agent and the hydroxy groups of the hydroxy functional polymer, one or more catalysts are typically present in the curable photochromic coating composition in amounts of from, for example, 0.1 to 5 percent by weight, based on total resin solids of the composition. Classes of useful catalysts include but are not limited to, metal compounds, in particular, organic tin compounds, e.g., tin(II) octanoate and dibutyltin(IV) dilaurate, and tertiary amines, e.g., diazabicyclo[2.2.2]octane.

Curable photochromic coating compositions according to the present invention, which include hydroxy functional polymer and capped isocyanate functional crosslinking agent, typically have present therein hydroxy functional polymer in an amount of from 55 percent to 95 percent by weight, based on total resin solids weight of the composition, e.g., from 75 percent to 90 percent by weight, based on total resin solids weight of the composition. The capped isocyanate functional crosslinking agent is typically present in the curable resin composition in an amount corresponding to the balance of these recited ranges, i.e., 5 to 45, particularly 10 to 25, percent by weight.

With the curable urethane resin compositions of the curable photochromic coating compositions of the present invention, the equivalent ratio of isocyanate equivalents in the capped isocyanate crosslinking agent to hydroxy equivalents in the hydroxy functional polymer is typically within the range of 1:3 to 3:1, e.g., 1:2 to 2:1. While equivalent ratios outside of this range can be employed, they are generally less desirable due to performance deficiencies in cured photochromic films obtained therefrom. Curable photochromic coating compositions according to the present invention that include hydroxy functional polymer and capped isocyanate functional crosslinking agent are typically cured at a temperature of from 120° C. to 190° C. over a period of from 10 to 60 minutes.

Photochromic coating compositions according to the present invention can, with some embodiments, optionally further include a solvent. Examples of suitable solvents include, but art not limited to, acetates, alcohols, ketones, glycols, ethers, aliphatics, cycloaliphatics and aromatics. Examples of acetates include, but are not limited to, ethyl acetate, butyl acetate, and glycol acetate. Examples of ketones include, but are not limited to, methyl ethyl ketone and methyl-N-amyl ketone. Examples of aromatics include, but are not limited to, are toluene, naphthalene and xylene. In an embodiment, one or more solvents are added to each of the first reactant and the second reactant. Suitable solvent blends can include, for example, one or more acetates, propanol and its derivatives, one or more ketones, one or more alcohols and/or one or more aromatics. If present, the solvent is typically present in an amount of from 5 to 60 percent by weight, or 5 to 40 percent by weight, or 10 to 25 percent by weight, based on the total weight of the photochromic coating composition (inclusive of the solvent weight).

Curable photochromic coating compositions according to the present invention can, with some embodiments, optionally contain additives such as waxes for flow and wetting, flow control agents, e.g., poly(2-ethylhexyl)acrylate, adjuvant resin to modify and optimize coating properties, antioxidants and ultraviolet (UV) light absorbers. Examples of useful antioxidants and UV light absorbers include those available commercially from Ciba-Geigy under the trademarks IRGANOX and TINUVIN. These optional additives, when used, are typically present in amounts up to 20 percent by weight (e.g., from 0.5 to 10 percent by weight), based on total weight of resin solids of the curable resin composition.

Photochromic compositions, articles and coating compositions according to the present invention can, with some embodiments, further include art-recognized additives that aid or assist in the processing and/or performance of the compositions or articles. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The photochromic compounds according to the present invention can be used in amounts (or ratios) such that the organic material or substrate (e.g., photochromic articles and photochromic coatings) into which the photochromic compounds are incorporated or otherwise connected exhibits desired optical properties. For example, the amount and types of photochromic compounds can be selected such that the organic material or substrate is clear or colorless when the photochromic compound is in the closed-form (e.g., in the bleached or unactivated state), and can exhibit a desired resultant color when the photochromic compound is in the open-form (e.g., when activated by actinic radiation). The precise amount of the photochromic compound that is utilized in the various photochromic compositions and articles described herein is not critical provided that a sufficient amount is used to produce the desired effect. The particular amount of the photochromic compound used can depend on a variety of factors, such as but not limited to, the absorption characteristics of the photochromic compound, the color and intensity of the color desired upon activation, and the method used to incorporate or connect the photochromic compound to the substrate. Although not limiting herein, according to various non-limiting embodiments disclosed herein, the amount of the photochromic compound that is incorporated into an organic material can range from 0.01 to 40 weight percent, or from 0.05 to 15, or from 0.1 to 5 weight percent, based on the weight of the organic material.

The present invention is more particularly described in the following examples, which are intended to be illustrative only, since numerous modifications and variations therein will be apparent to those skilled in the art. Unless otherwise specified, all parts and all percentages are by weight.

EXAMPLES

Photochromic Materials (PM)

Methods of making photochromic materials with and without at least one polymerizable group are well known to those skilled in the art. For example, and without limitation, Photochromic Material A (PM-A) 3,3-di(4-methoxyphenyl)-6,11,13-trimethyl-13-(2-(2-(2-hydroxyethoxy)ethoxy)ethoxy-3H,13H-indeno[2',3':3,4]naphtho[1,2-b]pyran can be prepared by following the process of Example 8 of U.S. Pat. No. 6,113,814, which example is incorporated herein by reference, except that in Step 7 of the process, triethylene glycol is used in place of diethylene glycol.

PM-B, a photochromic material such as 3-(4-(2-hydroxyethoxy)phenyl)-3-(4-methoxyphenyl)-13,13-dimethyl-3H,13H-indeno[2',3':3,4]naphtho[1,2-b]pyran can be prepared by reacting 7,7-dimethyl-5-hydroxy-7H-benzo[C]fluorene with 1-(4-(2-hydroxyethoxy)phenyl)-1-(4-methoxyphenyl)-2-propyn-1-ol using procedures known to those skilled in the art.

PM-C, a photochromic material such as 3-(4-methoxyphenyl)-3-(4-(2-hydroxyethoxy)phenyl)-6,7-dimethoxy-11-trifluoromethyl-13,13-dimethyl-3H,13H-indeno[2',3':3,4]naphtho[1,2-b]pyran can be prepared following the procedure of Example 1 in U.S. Patent Application Publication 2008/0103301 except that 1-(4-(2-hydroxyethoxy)phenyl)-1-(4-methoxyphenyl)-2-propyn-1-ol would be used in place of 1,1-bis(4-methoxyphenyl)-2-propyn-1-ol in Step 6, which example is hereby incorporated herein by reference.

PM-D, a photochromic material such as 3,3-di(4-methoxyphenyl)-6,11-dimethoxy-13-butyl-13-(2-hydroxyethoxy)-3H,13H-indeno[2',3':3,4]naphtho[1,2-b]pyran can be prepared by using the same process as described above for Photochromic Material A, except that 3,3-di(4-methoxyphenyl)-6,11-dimethoxy-13-butyl-13-hydroxy-3H,13H-indeno

[2',3':3,4]naphtho[1,2-b]pyran and ethylene glycol are reacted together in Step 7 of Example 8 of U.S. Pat. No. 6,113,814.

PM-E, a photochromic material such as 3-(4-morpholinophenyl)-3-(4-(2-hydroxy)ethoxy)phenyl-13,13-dimethyl-3H,13H-indeno[2',3':3,4]naphtho[1,2-b]pyran can be prepared following the procedure of Steps 1-5 of Example 7 in U.S. 2006/0022176A1, which disclosure is incorporated herein by reference.

Various non-limiting embodiments disclosed herein will now be illustrated in the following non-limiting examples.

Examples

In Part 1 of the Examples, the synthesis procedures used to make photochromic materials according to various non-limiting embodiments disclosed herein are set forth in Examples 1-22. In Part 2, the photochromic performance testing is described. In Part 3, the test results are reported.

Part 1—Photochromic Materials—Synthesis

In an oven-dried flask placed under a nitrogen atmosphere and equipped with a Dean-Stark trap, the product of Step 5 (26 g) was stirred in xylenes (520 mL). To this was added bismuth(III)trifluoromethanesulfonate (3.4 g) and then the reaction mixture was heated to reflux for 3 hours.

Example 1

Step 1

In an oven-dried flask (flask A) placed under a nitrogen atmosphere, a 1.0M solution of 3-methoxyphenylmagnesium bromide in tetrahydrofuran (800 mL) and an additional 300 mL of tetrahydrofuran anhydrous were stirred. The flask was placed in an ice bath and to it was added bis[2-(N,N-diethylamino)-ethyl]ether (152 mL) slowly drop-wise using an addition funnel over a 45 minute period. The mixture stirred for 1 hour during which time the solution partially solidified. In a separate oven-dried reaction flask (flask B), 4-bromobenzoyl chloride (160 g) was stirred in tetrahydrofuran anhydrous (740 mL). The flask was placed in an ice bath. The contents of flask A was scooped out of it and added to flask B portion-wise over 45 minutes. The reaction mixture was warmed to room temperature and stirred for an additional 2 hours. It was then slowly poured into a beaker containing a saturated aqueous solution of ammonium chloride (1.3 L) and ice. A separatory funnel was used to separate the layers. The aqueous layer was recovered and extracted with ethyl acetate (2×600 mL each time). The organic layers were combined and washed with a saturated aqueous solution of sodium bicarbonate (1 L), dried over sodium sulfate and concentrated by rotary evaporation to yield 231 grams of (4-bromophenyl)(3-methoxyphenyl)methanone. The product was not purified and was used in the next reaction as is.

Step 2

In an oven-dried flask placed under a nitrogen atmosphere, the product of Step 1 (90.6 g) and potassium tert-butoxide (56 g) were stirred in toluene (900 mL) using a mechanical stirrer. To this was added dimethyl succinate (70 mL) slowly drop-wise using an addition funnel over a 1 hour period. The exothermic reaction warmed to 40° C. during the dimethyl succinate addition and became more viscous. Additional toluene (400 mL) was added. The reaction mixture was stirred for an additional 2 hours. The reaction mixture was slowly poured into a beaker containing deionized water (1 L) and ice. To this was added concentrated hydrochloric acid until a pH of 1 was reached. A separatory funnel was used to separate the organic and aqueous layers. The aqueous layer was extracted with ethyl acetate 2 times (600 mL each). The organic layers were recovered, combined and washed with saturated aqueous solution of sodium chloride (700 mL), dried over sodium sulfate and concentrated by rotary evaporation to yield 150 grams of mixture of (E and Z) 4-(4-bromophenyl)-3-(methoxycarbonyl)-4-(3-methoxyphenyl)but-3-enoic acid. The product was used in the next reaction as is.

Step 3

In a flask placed under a nitrogen atmosphere, the product of Step 3 (126 g) was stirred in acetic anhydride (500 mL). The reaction mixture was heated to reflux for 3 hours and then cooled to room temperature. It was concentrated by rotary evaporation and toluene was added (2×200 mL) and evaporated to remove residual water. The resulting residue was purified by column chromatography on silica gel (1000 g) eluting with a solution of 25% ethyl acetate/75% hexanes. Fractions containing desired product were combined and concentrated by rotary evaporation. The resulting residue was recrystallized in methanol. The crystals were collected by vacuum filtration. Methyl 4-acetoxy-1-(4-bromophenyl)-7-methoxy-2-naphthoate (23 g) was isolated. This step was repeated to produce additional product for the next step.

Step 4

In an oven-dried flask placed under a nitrogen atmosphere, the product of Step 3 (25 g), 2,4-dimethoxyphenylboronic acid (11.1 g) and sodium carbonate (14.2 g) were stirred in 1,2-dimethoxyethane (125 mL) and deionized water (40 mL). A nitrogen purge line was inserted directly into the reaction mixture for 10 minutes and then removed. Tetrakis(triphenylphosphine)palladium(0) (1.4 g) was added to the reaction mixture. It was heated to reflux for 4 hours. After cooling to room temperature, the reaction mixture was poured into a beaker containing deionized water (1 L) and ice. Concentrated hydrochloric acid was added while stirring vigorously until the pH reached 3. The mixture was transferred to a separatory funnel and extracted with chloroform 3 times (400 mL each time). The organic layers were recovered, combined and then placed directly onto a silica gel column (600 g) eluting with a mixture of 30% ethyl acetate/70% hexanes. Fractions containing product were combined and concentrated by rotary evaporation. The resulting residue was slurried in a minimal amount of a solution of 10% ethyl acetate/90% hexanes. A solid precipitate was collected by vacuum filtration. 25.4 grams of methyl 4-acetoxy-1-(2',4'-dimethoxy-[1,1'-biphenyl]-4-yl)-7-methoxy-2-naphthoate was isolated.

Step 5

Lanthanum(III) chloride (44.2 g) and lithium chloride (13.2 g) were added to a reaction flask. The flask was placed in vacuum oven at 170° C. for 4 hours. It was then removed from the oven and immediately placed under a nitrogen atmosphere. The product of Step 4 (25.3 g) was charged to the reaction flask and the mixture stirred in tetrahydrofuran anhydrous (500 mL). The reaction flask was cooled in a dry ice/acetone bath. To it was added a 2M solution of propylmagnesium chloride in diethyl ether (155 mL) slowly drop-wise using an addition funnel over the course of 40 minutes. The reaction mixture was heated to 40° C. for 3 hours. It was then cooled to room temperature and slowly poured into a beaker containing deionized water (1 L) and ice. Concentrated hydrochloric acid was added to the mixture while stirring vigorously until the pH reached 3. The mixture was transferred to a separatory funnel and the organic layer and aqueous layer were separated. The aqueous layer was recovered, extracted with ethyl acetate 2 times (350 mL each time). The organic layers were recovered, combined and washed with a saturated aqueous solution of sodium bicarbonate (500 mL), dried over sodium sulfate and concentrated by rotary evaporation. The resulting residue was purified by a chromatography column of silica gel (200 g) eluting with a solution of 50% ethyl acetate/50% hexanes. Fractions containing product were combined and concentrated by rotary evaporation. The resulting residue weighed 26 grams and was composed of 4-(2',4'-dimethoxy-[1,1'-biphenyl]-4-yl)-3-(4-hydroxyheptan-4-yl)-6-methoxynaphthalen-1-ol and several impurities. It was used in the next reaction as is.

Step 6

After cooling to room temperature the reaction mixture was added directly to a column of silica gel (400 g). It was eluted with a solution of 60% ethyl acetate/40% hexanes. Fractions containing product were combined and concentrated by rotary evaporation. The resulting residue was further purified with a second chromatography column of silica gel that was identical in conditions used to the first column. Fractions containing product were combined and concentrated by rotary evaporation. The resulting residue weighed 3.6 grams and was 2-methoxy-7,7-dipropyl-9-(2,4-dimethoxyphenyl)-7H-benzo[C]fluoren-5-ol.

Step 7

In an oven-dried flask placed under a nitrogen atmosphere, the product of Step 6 (3.6 g) and 1-(4-(2-hydroxyethoxy)phenyl)-1-(4-methoxyphenyl)prop-2-yn-1-ol (2.9 g) were stirred in chloroform (72 mL). To this was added p-toluenesulfonic acid (145 mg). The reaction mixture was stirred at room temperature for 2 hours. It was then placed directly on a column of silica gel (300 g) eluting with a solution of 60% ethyl acetate/40% hexanes. Fractions containing product were combined and concentrated by rotary evaporation. The resulting residue weighed 3.0 g. An NMR spectrum showed the product to have a structure consistent with 3-(4-hydroxyethoxyphenyl)-3-(4-methoxyphenyl)-7-methoxy-11-(2,4-dimethoxyphenyl)-13,13-dipropyl-3H,13H-indeno[2',3':3,4]naphtho[1,2-b]pyran.

Step 8

The product of Step 7 (5.3 g), triethylamine (2.0 g), and tetrahydrofuran (50 mL) were combined in a reaction flask, and the mixture was stirred at room temperature. Sebacoyl chloride (1.3 g) was added drop-wise to the solution and the mixture was further stirred at room temperature for 2 hours. The mixture was filtered through a short silica gel plug and concentrated. The product was isolated by silica gel chromatography (ethyl acetate/methylene chloride (v/v), 1/20). The recovered product was precipitated from methylene chloride/methanol (v/v: 1/4) and filtered off as a purple-tinted powder (3.5 g). The nuclear magnetic resonance (NMR) spectrum showed the product to have a structure consistent with bis(2-(4-(3-(4-methoxyphenyl)-7-methoxy-11-(2,4-dimethoxyphenyl)-13,13-dipropyl-3H,13H-indeno[2',3':3,4]naphtho[1,2-b]pyran-3-yl)phenoxy)ethyl) decanedioate shown in the following graphic formula:

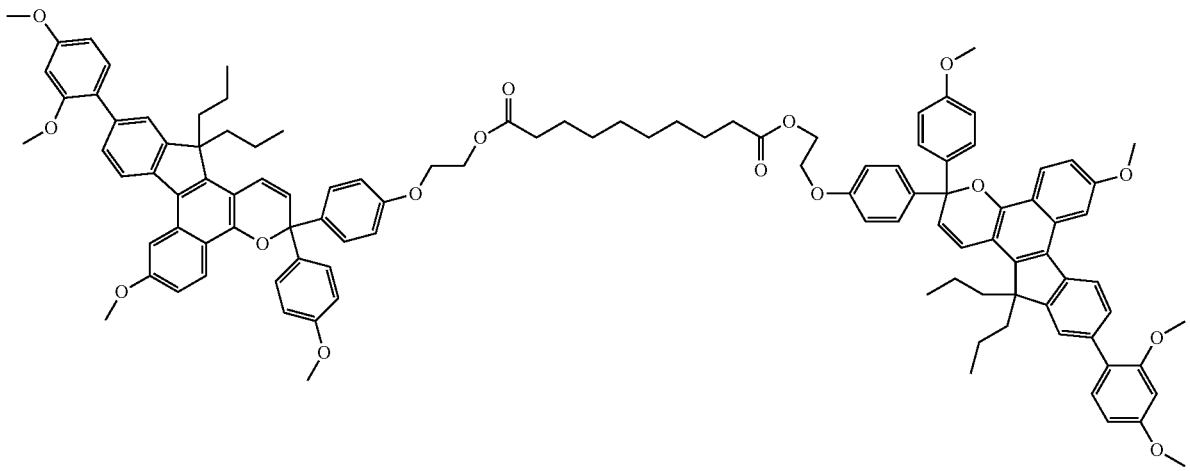

Example 2

PM-E, 3-(4-morpholinophenyl)-3-(4-(2-hydroxy)ethoxy)phenyl-13,13-dimethyl-3H,13H-indeno[2',3':3,4]naphtho[1,2-b]pyran (2.5 g), triethylamine (1.27 g), and methylene chloride (50 mL) were combined in a reaction flask, and the mixture was stirred at room temperature. Sebacoyl chloride (0.65 g) was added drop-wise to the solution. The mixture was further stirred at room temperature for 1 hour and filtered. Water (50 mL) was added to the filtrate and the mixture was partitioned. The methylene chloride layer was recovered, concentrated and the residue was purified by silica gel chromatography using as the eluant (ethyl acetate/hexanes (v/v), 1/1). The recovered product was precipitated from methylene chloride/methanol (v/v: 1/4) and filtered off as a blue-tinted powder (1 g). An NMR spectrum showed the product to have a structure consistent with bis(2-(4-(3-(4-morpholinophenyl)-13,13-dimethyl-3H,13H-indeno[2',3':3,4]naphtho[1,2-b]pyran-3-yl)phenoxy)ethyl) decanedioate shown in the following graphic formula:

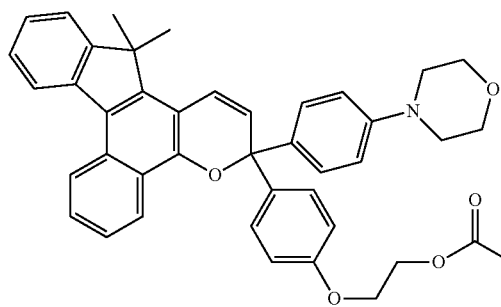

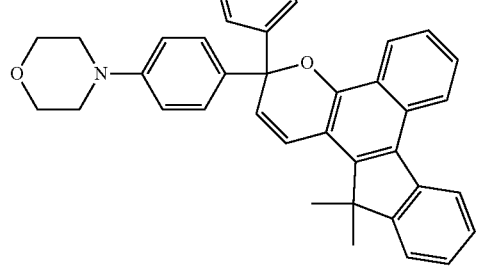

Example 3

PM-D, 3,3-bis-(4-methoxyphenyl)-6,11-dimethoxy-13-butyl-13-(2-hydroxy)-ethoxy-3H,13H-indeno[2',3':3,4]naphtho[1,2-b]pyran (7 g), 4.3 grams (4 equivalents) of triethyl amine and dry tetrahydrofuran (150 mL) were combined in a 250 mL reaction flask. To this was added 1.91 grams (0.75 equivalents) of sebacoyl chloride dropwise at room temperature under a nitrogen atmosphere. The reaction mixture was heated to reflux for 90 minutes. The reaction mixture was cooled to room temperature, and then poured into 200 mL of ethyl acetate. This mixture was washed twice, each time with 250 mL of a 1:1 mixture of saturated aqueous NaHCO₃ and water. The organic layer was recovered, dried over anhydrous sodium sulfate and concentrated by rotary evaporation. The resulting residue was purified by column chromatography. The pure fractions were combined, rotovaped and dried under vacuum to obtain 6.1 grams of a yellowish-greenish foam. Mass Spectrometry and NMR analysis show the foamy product to have a structure consistent with bis(2-(3,3-bis(4-methoxyphenyl)-6,11-dimethoxy-13-butyl-3H,13H-indeno[2',3':3,4]naphtho[1,2-b]pyran-13-yl-oxy)ethyl) decanedioate shown in the following graphic formula:

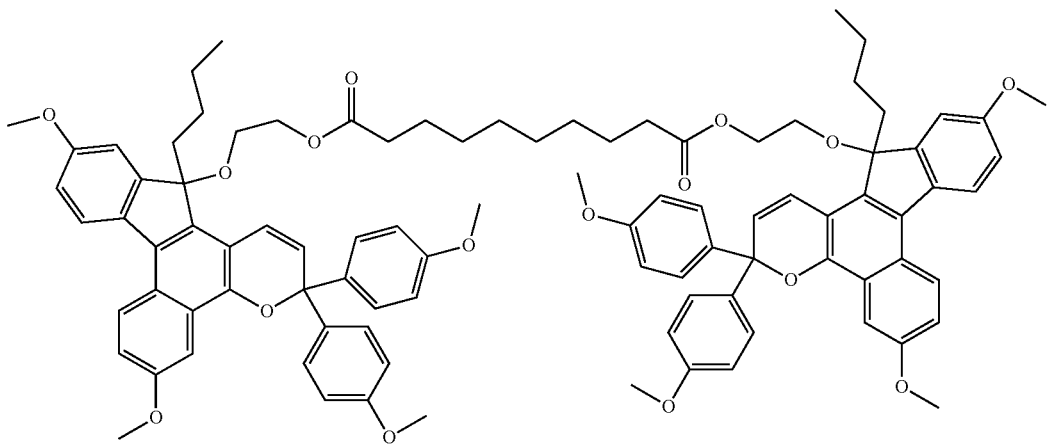

Example 4

Step 1

In an oven-dried flask placed under a nitrogen atmosphere, 4-fluorophenyl-4-hydroxyphenyl methanone (100 g), 2-chloroethanol (75 g), potassium carbonate (134 g) and potassium iodide (11.5 g) were stirred in anhydrous dimethylformamide (400 mL) using a mechanical stirrer. The reaction mixture was heated to reflux for 4 hours. It was cooled to room temperature and then poured into a beaker containing deionized water (1 L) and ice. Concentrated hydrochloric acid was added while stirring vigorously until the pH reached 3. The mixture was transferred to a separatory funnel and then extracted with chloroform (2×600 mL). The organic layers were combined and washed with a saturated aqueous solution of sodium bicarbonate (750 mL), dried over sodium sulfate and concentrated by rotary evaporation to yield a solid. The solid was slurried in a minimal amount of a solution of 10% ethyl acetate/90% hexanes and collected by vacuum filtration. 120 grams of 4-fluorophenyl-4-(2-hydroxyethoxy)phenyl methanone was isolated.

Step 2

In an oven-dried flask placed under a nitrogen atmosphere, the product of Step 1 (121 g) and 3,4-dihydro-2H-pyran (106 mL) were stirred in dichloromethane (1100 mL). To this was added p-toluenesulfonic acid (4.4 g). The reaction mixture was stirred at room temperature for 2 hours. It was then transferred to a separatory funnel and washed with a saturated aqueous solution of sodium bicarbonate (1 L), dried over sodium sulfate and concentrated by rotary evaporation to yield an oil. 160 grams of 4-fluorophenyl-4-(2-((tetrahydro-2H-pyran-2-yl)oxy)ethoxy)phenyl methanone was isolated. It was used in the next reaction as is without further purification.

Step 3

In an oven-dried flask placed under a nitrogen atmosphere, the anhydrous product of Step 2 (160 g) was stirred in dimethylformamide that had been saturated with acetylene gas (640 mL). The reaction flask was placed in an ice bath and to the reaction flask was added an 18 wt % slurry of sodium acetylide in xylenes and mineral oil (310 g) drop-wise using an addition funnel over a 40 minute period. The reaction was warmed to room temperature and stirred for 2 hours. It was slowly poured into a beaker containing deionized water (2 L), ice and chloroform (1 L). The mixture was transferred to a separatory funnel and then the aqueous layer and organic layer were separated. The aqueous layer was extracted with chloroform (750 mL). The organic layers were combined and washed with a saturated aqueous solution of ammonium chloride (750 mL) followed by a saturated aqueous solution of sodium bicarbonate (750 mL). The recovered organic layer was dried over sodium sulfate and concentrated by rotary evaporation. The resulting residue was purified by column chromatography on silica gel (1000 g) eluting with a solution of 35% ethyl acetate/65% hexanes. Fractions containing product were combined and concentrated by rotary evaporation to yield an oil. 120 grams of 4-fluorophenyl-1-(4-(2-(tetrahydro-2H-pyran-2-yl)oxy)ethoxy)phenyl-prop-2-yn-1-ol was isolated.

Step 4

In an oven-dried flask placed under a nitrogen atmosphere, 2,3-dimethoxy-7,7-dimethyl-9-cyano-7H-benzo[C]fluoren-5-ol (100 g), prepared according to Steps 1 to 6 of Example 1 of U.S. Patent Publication 2006/0228557 A1, which disclosure is incorporated herein by reference, and the product of Step 3 (130 g) were stirred in chloroform (2 L). To this was added bismuth(III)trifluoromethanesulfonate (2 g). The reaction mixture was stirred at room temperature for 3 hours. It was separated using a silica gel column (200 g) eluting with a solution of 50% chloroform/50% ethyl acetate. Fractions containing product were combined and concentrated by rotary evaporation. The resulting residue was dissolved in chloroform (300 mL) and methanol (700 mL) and transferred to a reaction flask. To it was added p-toluenesulfonic acid (5 g). The reaction mixture was heated to reflux for 4 hours. Upon cooling to room temperature, a solid precipitated out of solution which was collected by vacuum filtration. The product (105 grams) of 3-(4-(2-hydroxyethoxy)phenyl)-3-(4-fluorophenyl)-6,7-dimethoxy-11-cyano-13,13-dimethyl-3H,13H-indeno[2',3':3,4]naphtho[1,2-b]pyran was isolated.

Step 5

In an oven-dried reaction flask placed under a nitrogen atmosphere, the product of Step 4 (100.7 g) and triethylamine (50 g) were stirred in dichloromethane (1500 mL). Sebacoyl chloride (21.6 g) dissolved in dichloromethane (450 mL) was added to the reaction mixture drop-wise using an addition funnel over a 1.5 hour period. It was stirred at room temperature for 1 hour. The reaction mixture was poured into a beaker containing a saturated aqueous solution of ammonium chloride (2 L) and ice. The mixture was transferred to a separatory funnel and the organic and aqueous layers were separated. The recovered aqueous layer was extracted with dichloromethane (600 mL). The organic layers were combined and washed with a saturated aqueous solution of sodium bicarbonate (1 L), dried over sodium sulfate and concentrated by rotary evaporation. The resulting residue was purified by column chromatography on silica gel (1300 g) eluting with a solution of 50% ethyl acetate/50% hexanes. The fractions containing product were combined and concentrated by rotary evaporation. The resulting residue was further purified with a second silica gel column (1300 g) eluting with 25% ethyl acetate/75% hexanes. Fractions containing product were combined and concentrated by rotary evaporation. The resulting residue was dissolved in a minimal amount of dichloromethane. It was slowly dropped into a beaker containing vigorously stirring methanol (1.8 L). A solid precipitated out of solution. Product was collected by vacuum filtration and weighed 65 grams. NMR analysis indicated the product to have a structure consistent with bis(2-(4-(3-(4-fluorophenyl)-6,7-dimethoxy-11-cyano-13,13-dimethyl-3H,13H-indeno[2',3':3,4]naphtho[1,2-b]-3-yl)phenoxy)ethyl) decanedioate shown in the following graphic formula:

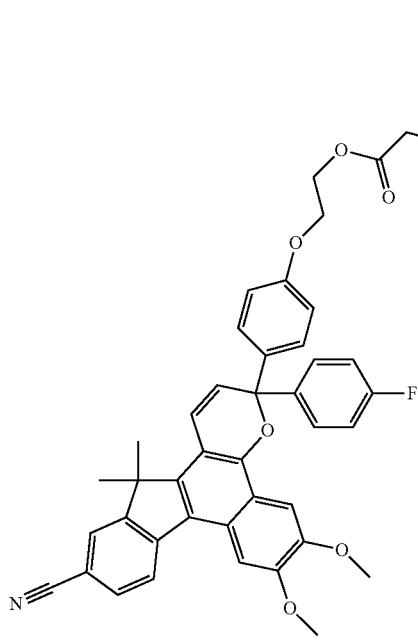
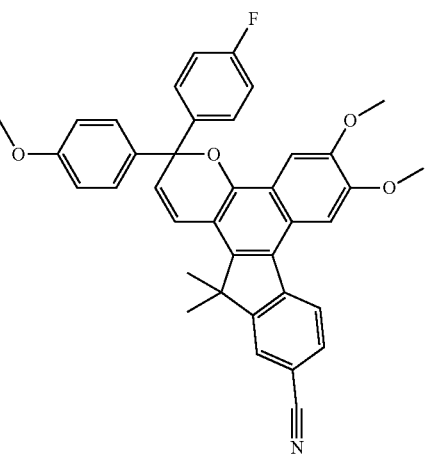

Example 5

Step 1

To a 1 L single-neck flask was added 3-methoxyphenylmagnesium bromide in tetrahydrofuran (1M, 560 mL). The flask was set up with a $N_2$ blanket and magnetic stirring. The flask was seated in ice-salt-water bath (−5 to −8° C.). 1,2-Dimethylamino ethyl ether (106 mL) in tetrahydrofuran (100 mL) was dropped to the flask through an addition funnel over 10 minutes. The mixture was stirred for 1 hour. 4-Bromobenzoyl chloride in tetrahydrofuran (122 g in 100 mL) suspension was dropped into the flask using an addition funnel over 20 minutes. The cooling bath was removed 1 hour after the addition. The mixture was stirred at room temperature for 20 hours. The solution was poured into brine (1 L). Conc. hydrochloric acid (250 mL) was added to the mixture slowly. The top layer was separated and filtered through magnesium sulfate. The solution was concentrated to initially yield an orange-red oily residue (182 g) that became a yellow waxy product. The residue was dried under high vacuum and used as is in next step.

Step 2

The crude product from Step 1 (182 gram) was dissolved in toluene (1 L) in a 2 L single-neck RB flask with $N_2$ blanket and overhead stirring. Dimethyl succinate (72 mL) was added to the same flask. Potassium t-butoxide (68 gram) was added to the mixture in portions over 20 minutes. The reaction mixture stirred at room temperature for 20 hours. After 3 hours the dark slurry was poured into cold water (400 mL). The bottom water layer was separated and acidified by conc. HCl (200 mL). The slurry was extracted with ethyl acetate twice with (500 mL and 300 mL). The top solution was dried over sodium sulfate and concentrated. The residue was dried under high vacuum (170 g) and used as is in next step.

Step 3

The oily product from Step 2 (170 gram) and trace amount of 4-dimethylaminopyridine (0.2 gram) were dissolved in acetic anhydride (250 mL) in 1 L single-neck RB flask equipped with a water condenser and magnetic stirring under $N_2$ blanket. The reaction mixture was heated to 120° C. for 3 hours. The mixture was then condensed down to less volume under reduced pressure. The recovered oily residue was dissolved in methanol. Solid product crystallized out and was recovered by filtration yielding (80 grams). NMR analysis showed the product to have a structure consistent with methyl 4-acetoxy-1-(4-bromophenyl)-7-methoxy-2-naphthoate.

Step 4

To a 1 L single-neck flask was added the product of Step 3 (63 g), phenylboronic acid (21 g), potassium carbonate (100 g), toluene (240 mL), ethanol (120 mL) and water (120 mL). The mixture was bubbled with $N_2$ for 15 minutes. Tetrakis(triphenylphosphine)palladium(0) (1.5 g) was added to the mixture. The reaction mixture was heated to reflux for 4.5 hours. The mixture was cooled to room temperature and poured into water (500 mL). The resulting mixture was acidified with concentrated hydrochloric acid (12N, 200 mL). The top organic layer was recovered, filtered through magnesium sulfate and then concentrated. Solid product was obtained from the solution. The mother liquor was filtered through a short silica gel plug. Solid product was obtained from the major fraction. The combined product (64 g) was dried in vacuum oven.

Step 5

To a 3 L one-neck RB flask was added dry solid lanthanum (III) chloride (130 g), lithium chloride (37 g), the product from Step 4 (60 g) and anhydrous THF (1.5 L). The white slurry was stirred at room temperature for 20 hours. The flask was cooled in a dry ice/acetone bath. N-Propylmagnesium chloride in tetrahydrofuran solution (2M, 425 mL) was dropped to the mix slowly. The cooling bath was removed upon completing the addition. The reaction mixture was stirred for 3 hours. The mixture was poured into 30% aqueous hydrochloric acid (500 mL) and ice. The recovered top layer was filtered over magnesium sulfate and then concentrated. The resulting oily product (74 g) was used as is in Step 9.

Step 6

The product from Step 5 was dissolved in xylene (400 mL) in a 2 L single-neck flask equipped with Dean-Stark trap and water condenser. Bismuth trifluoromethanesulfonate (1.6 g) was added to the flask. The reaction mixture was heated to reflux for 4 hours. The resulting mixture was cooled to room temperature and filtered through a silica gel plug. The major fraction was collected and condensed to less volume. Solid product (65 g) was recrystallized out from t-butyl methyl ether/hexane solution to yield an off-white solid, 9-phenyl-2-methoxy-7,7-dipropyl-7H-benzo[c]fluoren-5-ol.

Step 7

The products from Step 6 (65 g), pyridinium p-toluenesulfonate (3 g) and 1-(4-methoxyphenyl)-1'-(4-(2-hydroxy)ethoxyphenyl)prop-2-yn-1-ol (45 g) were dissolved in 1,2-dichloroethane (400 mL) in a 1 L single-neck flask. The mixture was heated to 80° C. for 2 hours. The mixture was cooled to room temperature and filtered through a short silica gel plug. The major fraction was further purified by silica gel chromatography eluting with ethyl acetate/hexanes to afford an oily product. Solid product (55 g) was obtained by precipitation of the oily product in hexanes.

Step 8

The product from Step 7 (50 g), dimethylaminopyridine (0.1 g) and triethylamine (13 mL) were dissolved in methylene chloride (300 mL) in a 2 L single-neck reaction flask. To the flask was slowly added sebacoyl chloride (9 mL) in methylene chloride (100 mL) using an addition funnel. The mixture was stirred at room temperature for 30 minutes. The reaction mixture was poured into water (500 mL). The bottom organic layer was recovered, filtered over magnesium sulfate and then condensed to less volume. The residue was purified by chromatography eluting with a solution of ethyl acetate/hexanes. The major fraction was collected and condensed to less volume. Solid product (47 g) was precipitated out from methanol. NMR analysis indicated that one of the products had a structure consistent with bis-(2-(4-(3-(4-methoxyphenyl)-7-methoxy-11-phenyl-13,13-dipropyl-3H,13H-indeno[2',3':3,4]naphtho[1,2-b]pyran-3-yl)phenoxy)ethyl) decanedioate shown in the following graphic formula:

Example 6

Step 1

1-(4-2-Hydroxyethoxyphenyl)-1-(4-methoxyphenyl)-2-propyn-1-ol was prepared according to the procedure of Steps 1 and 3 of Example 7 in U.S. 2006/0022176A1, except that 4-hydroxy-4'-methoxy-benzophenone was substituted for 4-hydroxy-4'-fluoro-benzophenone. This disclosure is incorporated herein by reference.

Step 2

1-Phenyl-2-methoxycarbonyl-6-methoxy-4-acetoxynaphthalene was prepared according to the procedures of Steps 1 and 2 of U.S. Pat. No. 5,645,767, except that 4-methoxy benzophenone was substituted for benzophenone. This disclosure is incorporated herein by reference.

Step 3

The product Step 2 (50 grams) was added to a reaction flask containing 500 mL of tetrahydrofuran. The resulting mixture was cooled in a ice water bath and stirred under a nitrogen atmosphere. Methyl magnesium chloride solution (703 mL of a 1M in tetrahydrofuran) was added dropwise over forty-five minutes. The resulting yellow reaction mixture was stirred at 0° C. for 2 hours and slowly warmed to room temperature. The reaction mixture was poured into 2 L of an ice/water mixture. Ether (1 L) was added, and the layers separated. The aqueous layer was extracted with two 500 mL portions of ether, and the organic portions were combined and washed with 1 L of water. The organic layer was dried over anhydrous sodium sulfate and concentrated by rotary evaporation. The resulting oil was transferred into a reaction vessel (fitted with a Dean-Stark trap) containing 500 mL of toluene to which ten drops of dodecylbenzene sulfonic acid were added. The reaction mixture was heated to reflux for 2 hours and cooled. The toluene was removed via rotary evaporation to yield 40.2 grams of an light yellow solid. An NMR spectrum showed the product to have a structure consistent with 7,7-dimethyl-5-hydroxy-3-methoxy-7H-benzo[C]fluorene.

Step 4

The product of Step 1 (4.0 grams), the product of Step 3 (4.0 grams), and 100 mL of chloroform were combined in a reaction flask and stirred at 40° C. Sufficient dodecylbenze-

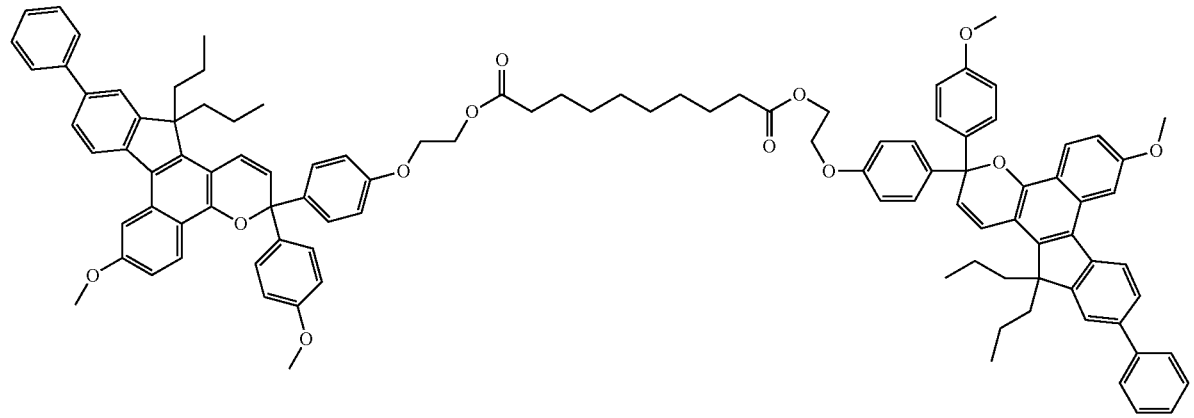 [SMILES: CCCC1(CCC)c2cc(-c3ccccc3)ccc2-c2c1c1c(c3ccc(OC)cc23)OC(c2ccc(OC)cc2)(c2ccc(OCCOC(=O)CCCCCCCCC(=O)OCCOc3ccc(C4(c5ccc(OC)cc5)C=Cc5c6c(c7cc(OC)ccc7c5O4)-c4ccc(-c5ccccc5)cc4C6(CCC)CCC)cc3)cc2)C=C1]

nesulfonic acid was added (3-5 drops) to produce a deep black coloration to the solution. After two hours, the reaction mixture was cooled and washed with 100 mL of water. The organic layer was separated, dried over sodium sulfate, and concentrated by rotary evaporation to yield dark oil. Methanol (100 mL) was added to the product. Upon warming and stirring, the product readily crystallized. The crystals were filtered, washed with fresh methanol and dried to yield 4.2 grams of an off-white solid. An NMR spectrum showed the product to have a structure consistent with 3-(4-methoxyphenyl)-3-(4-(2-hydroxy)ethoxyphenyl)-6-methoxy-13,13-dimethyl-3H,13H-indeno[2',3':3,4]naphtho[1,2-b]pyran.

Step 5

The product of Step 4 (4.16 g), succinic anhydride (2.2 g), 4-dimethylaminopyridine (45 mg), and anhydrous tetrahydrofuran (80 mL) were combined in a reaction flask. The reaction mixture was heated at reflux for 4 hours and then stirred at 55° C. overnight. The reaction mixture was concentrated. The product was crystallized from acetone/methanol (1/1), yielding 4.5 g of a green-tinted solid, 3-(4-methoxyphenyl)-3-(4-(2-((3-carboxypropanoyl)oxy)ethoxy))phenyl-6-methoxy-13,13-dimethyl-3H,13H-indeno[2',3':3,4]naphtho[1,2-b]pyran.

Step 6

The product of Step 5 (4.49 g), decanediol (0.58 g), N,N'-dicyclohexylcarbodiimide (1.52 g), 4-dimethylaminopyridine (0.49 g), dodecyl benzenesulfonic acid (1.09 g), and methylene chloride (70 mL) were combined in a reaction flask. The reaction mixture was stirred at room temperature overnight. The mixture was filtered and concentrated. The product was isolated by silica gel chromatography (methylene chloride and then ethyl acetate/methylene chloride (v/v), 1/6), yielding 3.0 g of a green-tinted solid. An NMR spectrum showed the product to have a structure consistent with O,O'-decane-1,10-diyl bis(2-(4-(3-(4-methoxyphenyl)-6-methoxy-13,13-dimethyl-3H,13H-indeno[2',3':3,4]naphtho[1,2-b]pyran-3-yl)phenoxy)ethyl)disuccinate shown in the following graphic formula:

Example 7

Step 1

Into a 1 liter reaction (3 neck) flask was added 2,3-dimethoxy-7,7-dimethyl-9-bromo-7H-benzo[C]fluoren-5-ol (25 grams), the product of Step 5 of Example 1 in U.S. Patent Publication 2006-0228557, which disclosure is incorporated herein by reference, 2,3,4-trifluorophenyl boronic acid (13.82 g), $Na_2CO_3$ (13.32 g), 1,2-dimethoxyethane (300 mL), water (150 mL). Nitrogen was bubbled through the reaction mixture for 10 minutes. Tetrakis (triphenylphosphine) palladium (0) (3.63 g) was added to the reaction mixture and the resulting reaction mixture was heated to reflux and maintained at reflux for 6 hours. The reaction was cooled to room temperature and poured into 500 mL of water/50 mL of 10% HCl followed by extraction with ethyl acetate (2×300 mL each time). The organic (ethyl acetate) layers were recovered, combined and washed with saturated NaCl solution (400 mL). This organic layer was dried over anhydrous sodium sulfate and concentrated by rotary evaporation to obtain 27.5 g of material. This resulting material (2,3-dimethoxy-7,7-dimethyl-9-(2,3,4-trifluorophenyl)-7H-benzo[C]fluoren-5-ol) was used without further purification for Step 2.

Step 2

Into a 500 mL reaction flask was added the product of Step 1 (6.0 g), 1-(4-methoxyphenyl)-1'-(4-(2-hydroxy)ethoxyphenyl)-2-propyn-1-ol (4.4 g), and chloroform (250 mL). To the resulting reaction mixture was added 0.34 grams of PPTS (pyridinium p-toluene-sulfonate). The reaction mixture was stirred at room temperature for 4 hours and further additions of 1-(4-methoxyphenyl)-1'-(4-(2-hydroxy)ethoxyphenyl)-2-propyn-1-ol (2.0 g), and PTSA (p-toluene-sulfonic acid, 0.5 g) were made. The reaction mixture was stirred overnight and then washed with 400 mL of a 1:1 mixture of saturated aqueous $NaHCO_3$ and water. The organic layer was dried over anhydrous sodium sulfate and concentrated by rotary evaporation. The resulting residue was purified by purified by chromatography to get 8.4 grams of a grayish solid. This solid was slurried in diethyl ether and filtered to obtain 7.22 grams of an off-white solid product. NMR analysis showed the product to have a structure consistent with 3-(4-methoxyphenyl)-3-(4-

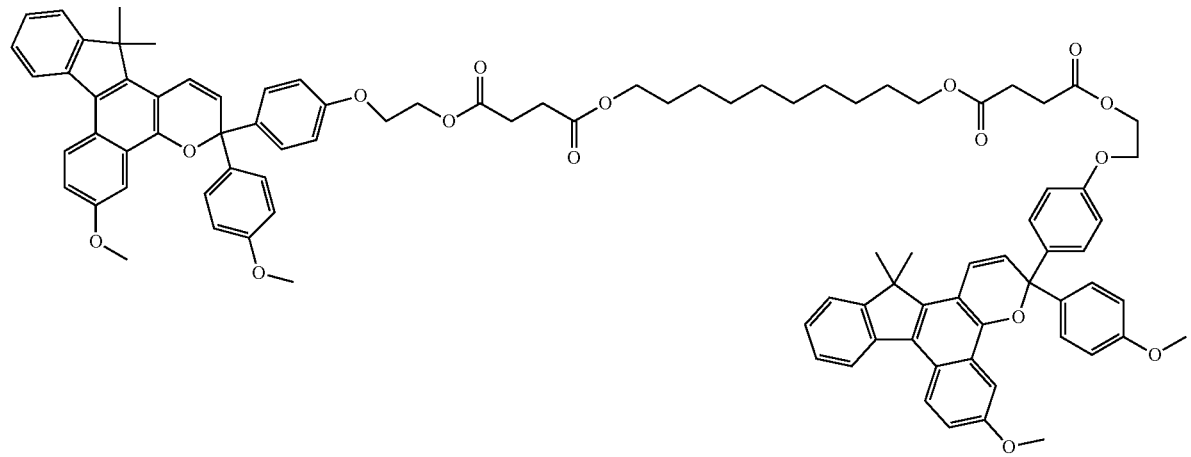 [SMILES: COc1ccc(C2(c3ccc(OCCOC(=O)CCC(=O)OCCCCCCCCCCOC(=O)CCC(=O)OCCOc4ccc(C5(c6ccc(OC)cc6)C=Cc6c7c(c8ccc(OC)cc8c6O5)-c5ccccc5C7(C)C)cc4)cc3)C=Cc3c4c(c5ccc(OC)cc5c3O2)-c2ccccc2C4(C)C)cc1]

(2-hydroxy)ethoxyphenyl)-6,7-dimethoxy-11-(2,3,4-trifluorophenyl)-13,13-dimethyl-3H,13H-indeno[2',3':3,4]naphtho[1,2-b]pyran.

Step 3

The product of Step 2 (3.90 g), succinic anhydride (1.6 g), 4-dimethylaminopyridine (33 mg), and anhydrous tetrahydrofuran (80 mL) were combined in a reaction flask. The reaction mixture was heated at reflux for 4 hours and then stirred at 55° C. overnight. The reaction mixture was concentrated and the product was crystallized from methylene chloride/methanol (1/2, v/v), yielding 4.1 g of a green-tinted solid, 3-(4-methoxy)phenyl-3-(4-(2-((3-carboxypropanoyl)oxy)ethoxy))phenyl-6,7-dimethoxy-11-(2,3,4-trifluoro)phenyl-13,13-dimethyl-indeno[2',3':3,4]naphtho[1,2-b]pyran.

Step 4

The product of Step 3 (4.0 g), decanediol (0.41 g), N,N'-dicyclohexylcarbodiimide (1.09 g), 4-dimethylaminopyridine (0.35 g), dodecyl benzenesulfonic acid (0.79 g), and methylene chloride (60 mL) were combined in a reaction flask. The reaction mixture was stirred at room temperature overnight. The mixture was filtered and concentrated. The product was isolated by silica gel chromatography using methylene chloride and then ethyl acetate/methylene chloride (v/v), 1/20, yielding 2.5 g of a green-tinted solid. An NMR spectrum showed the product to have a structure consistent with O,O'-decane-1,10-diyl bis-(2-(4-(3-(4-methoxyphenyl)-6,7-dimethoxy-11-(2,3,4-trifluorophenyl)-13,13-dimethyl-3H,13H-indeno[2',3':3,4]naphtho[1,2-b]pyran-3-yl)phenoxy)ethyl)disuccinate shown in the following graphic formula:

Example 8

Step 1

PM-C, 3-(4-methoxyphenyl)-3-(4-(2-hydroxy)ethoxyphenyl)-6,7-dimethoxy-11-trifluoromethyl-13,13-dimethyl-3H,13H-indeno[2',3':3,4]naphtho[1,2-b]pyran (3.5 g), succinic anhydride (1.05 g), 4-dimethylaminopyridine (32 mg), and anhydrous tetrahydrofuran (30 mL) were combined in a reaction flask. The reaction mixture was heated at reflux for 4 hours and then stirred at 55° C. overnight. The reaction mixture was concentrated. The product was isolated by silica gel chromatography (ethyl acetate/hexanes (v/v): 1/1), yielding 3.7 g of a brown-tinted solid, 3-(4-methoxyphenyl)-3-(4-(2-(3-carboxypropanoyl)oxy)ethoxyphenyl)-6,7-dimethoxy-11-trifluoromethyl-13,13-dimethyl-3H,13H-indeno[2',3':3,4]naphtho[1,2-b]pyran.

Step 2

The product of Step 1 (3.6 g), decanediol (0.408 g), N,N'-dicyclohexylcarbodiimide (1.06 g), 4-dimethylaminopyridine (0.343 g), dodecyl benzenesulfonic acid (0.764 g), and methylene chloride (120 mL) were combined in a reaction flask. The reaction mixture was stirred at room temperature overnight. The mixture was filtered and concentrated. The product was isolated by silica gel chromatography using as eluant ethyl acetate/hexanes (v/v): 1/1, followed by a second short silica gel chromatography (ethyl acetate/hexanes (v/v): 2/1), yielding 2.4 g of a brown-tinted solid. An NMR spectrum showed the product to have a structure consistent with O,O'-decane-1,10-diyl bis-(2-(4-(3-(4-methoxyphenyl)-6,7-dimethoxy-11-trifluoromethyl-13,13-dimethyl-3H,13H-indeno[2',3':3,4]naphtho[1,2-b]pyran-3-yl)phenoxy)ethyl)disuccinate shown in the following graphic formula:

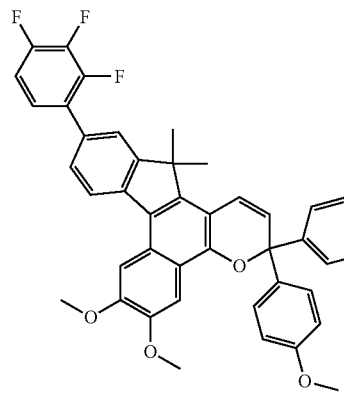
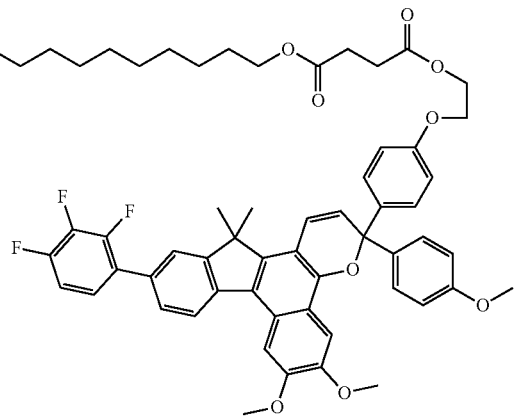

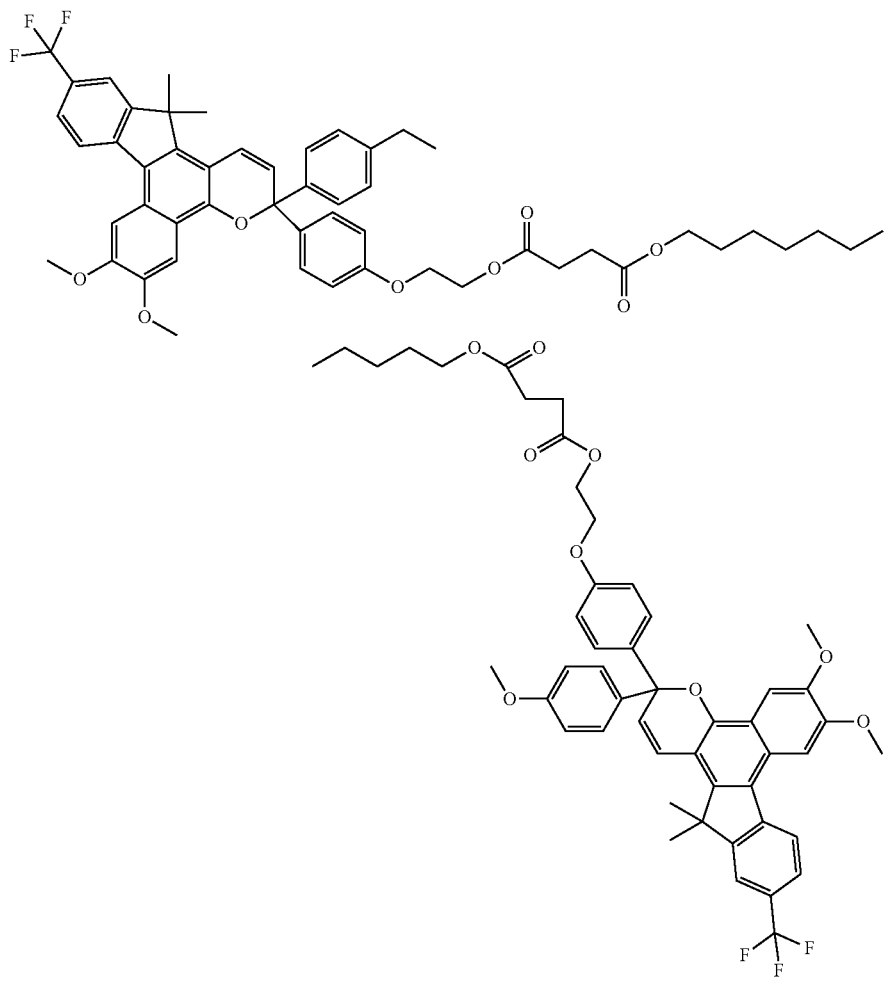

Example 9

Step 1

2,3-Dimethoxy-7,7-dimethyl-9-bromo-7H-benzo[C]fluoren-5-ol (50.0 g, the product of Step 5 of Example 1 of US2006/0226402 A1, which example is hereby specifically incorporated by reference herein), tetrakis(triphenylphosphine)palladium (5.0 g), (2-trifluoromethyl)phenyl boronic acid (26.2 g), sodium carbonate (39.8 g), ethylene glycol dimethyl ether (400 mL), and water (300 mL) were combined in a reaction flask under a nitrogen atmosphere and stirred for 1 hour at room temperature. The mixture was then heated to reflux temperature for 24 hours. The reaction mixture was cooled to room temperature and poured into water (1 L) and extracted with ethyl acetate (three times with 500 mL). The organic extracts were combined and the solvent was removed by rotary evaporation to give 46.5 g of a light yellow solid. NMR spectra showed the product to have a structure consistent with 2,3-dimethoxy-7,7-dimethyl-9-(2-trifluoromethylphenyl)-7H-benzo[C]fluoren-5-ol.

Step 2

The product of Step 1 (4.0 g), 1-(4-(2-hydroxyethoxy)phenyl-1-(4-morpholinophenyl)-2-propyn-1-ol (3.7 g, made as described in Step 3 of Example 7 of U.S. 2006/0022176A1), which disclosure is incorporated herein by reference), dodecylbenzene sulfonic acid (0.2 g) and chloroform (preserved with pentene, 250 mL) were combined in a reaction flask and stirred at room temperature for 5 hours. The reaction mixture was washed with 50% saturated aqueous NaHCO$_3$ (200 mL) and the organic layer was dried over anhydrous Na$_2$SO$_4$. The solvent was removed by rotary evaporation. Hot methanol was added to the resulting residue and the solution cooled to room temperature. The resulting precipitate was collected by vacuum filtration and washed with cold methanol yielding 4.7 g of 3-(4-morpholinophenyl)-3-(4-(2-hydroxy)ethoxy)phenyl-6,7-dimethoxy-11-(2-trifluoromethylphenyl)-13,13-dimethyl-3H,13H-indeno[2',3':3,4]naphtho[1,2-b]pyran.

Step 3

In a dried 250 mL two neck flask under nitrogen, piperidine (1.4 g) was added into THF (100 mL). The flask was placed in an ice bath and to it was added n-butyl lithium (nBuLi) (5 mL, 2.5 M) slowly dropwise over 10 min. The ice bath was removed and the reaction mixture was heated to 70° C. for 4 hrs. The mixture was cooled down to room temperature and the product of Step 2 (2.5 g) was added slowly. The reaction mixture was stirred for 1 hour at room temperature and poured into 200 mL water. The mixture was extracted with ethyl acetate (three times with 200 mL each time). The organic extracts were combined and the solvent was removed by rotary evaporation to give 2.9 g of 3-(4-morpholinophenyl)-3-(4-(2-hydroxy)ethoxyphenyl)-6-methoxy-7-piperidino-11-(2-trifluoromethylphenyl)-13,13-dimethyl-3H,13H-indeno[2',3':3,4]naphtho[1,2-b]pyran.

Step 4

The product of Step 3 (2.1 g), succinic anhydride (0.49 g), 4-dimethylaminopyridine (15 mg), and anhydrous tetrahydrofuran (30 mL) were combined in a reaction flask. The reaction mixture was heated at reflux for 4 hours and then stirred at 55 C overnight. The reaction mixture was concentrated. The product was isolated by silica gel chromatography (ethyl acetate/hexanes (v/v): 3/1), yielding 2.0 g of a purple-tinted solid, 3-(4-morpholinophenyl)-3-(4-(2-(3-carboxypropanoyl)oxy)ethoxyphenyl)-6-methoxy-7-piperidino-11-(2-trifluoromethylphenyl)-13,13-dimethyl-3H,13Hindeno[2',3':3,4]naphtho[1,2-b]pyran.

Step 5

The product of Step 4 (1.8 g), decanediol (0.165 g), N,N'-dicyclohexylcarbodiimide (0.43 g), 4-dimethylaminopyridine (0.14 g), dodecyl benzenesulfonic acid (0.31 g), and methylene chloride (42 mL) were combined in a reaction flask. The reaction mixture was stirred at room temperature overnight. The mixture was filtered and concentrated. The product was isolated by silica gel chromatography (ethyl acetate/hexanes (v/v): 4/1), yielding 1.2 g of a purple-tinted solid. An NMR spectrum showed the product to have a structure consistent with O,O'-decane-1,10-diylbis-(2-(4-(3-(4-morpholinophenyl)-6-methoxy-7-piperidino-11-(2-trifluoromethylphenyl)-13,13-dimethyl-3H,13Hindeno[2',3':3,4]naphtho[1,2-b]pyran-3-yl)phenoxy)ethyl)disuccinate shown in the following graphic formula:

Example 10

Step 1

PM-D, 3,3-bis-(4-methoxyphenyl)-6,11-dimethoxy-13-butyl-13-(2-hydroxy)ethoxy-3H,13H-indeno[2',3':3,4]naphtho[1,2-b]pyran (3.5 g), succinic anhydride (1.06 g), 4-dimethylaminopyridine (32 mg), and anhydrous tetrahydrofuran (30 mL) were combined in a reaction flask. The reaction mixture was heated at reflux for 4 hours and then stirred at 55° C. overnight. The reaction mixture was concentrated. The product was isolated by silica gel chromatography using as eluant ethyl acetate/hexanes (v/v): 1/1, yielding 3.6 g of a green-tinted solid, 3,3-bis-(4-methoxyphenyl)-6,11-dimethoxy-13-butyl-13-(2-(3-carboxypropanoyl)oxy)ethoxy-3H,13H-indeno[2',3':3,4]naphtho[1,2-b]pyran.

Step 2

The product of Step 1 (1.53 g), decanediol (0.176 g), N,N'-dicyclohexylcarbodiimide (0.457 g), 4-dimethylaminopyridine (0.148 g), dodecyl benzenesulfonic acid (0.33 g), and methylene chloride (52 mL) were combined in a reaction flask. The reaction mixture was stirred at room temperature overnight. The mixture was filtered and concentrated. The product was isolated by silica gel chromatography using as eluant ethyl acetate/hexanes (v/v): 1/1, followed by a second short silica gel chromatography using as eluant ethyl acetate/hexanes (v/v): 2/1, yielding 1.0 g of a green-tinted solid. An NMR spectrum showed the product to have a structure consistent with O,O'-decane-1,10-diyl bis-(2-(3,3-bis-(4-methoxyphenyl)-6,11-dimethoxy-13-butyl-3H,13H-indeno[2',3':3,4]naphtho[1,2-b]pyran-13-yl-oxy)ethyl)disuccinate shown in the following graphic formula:

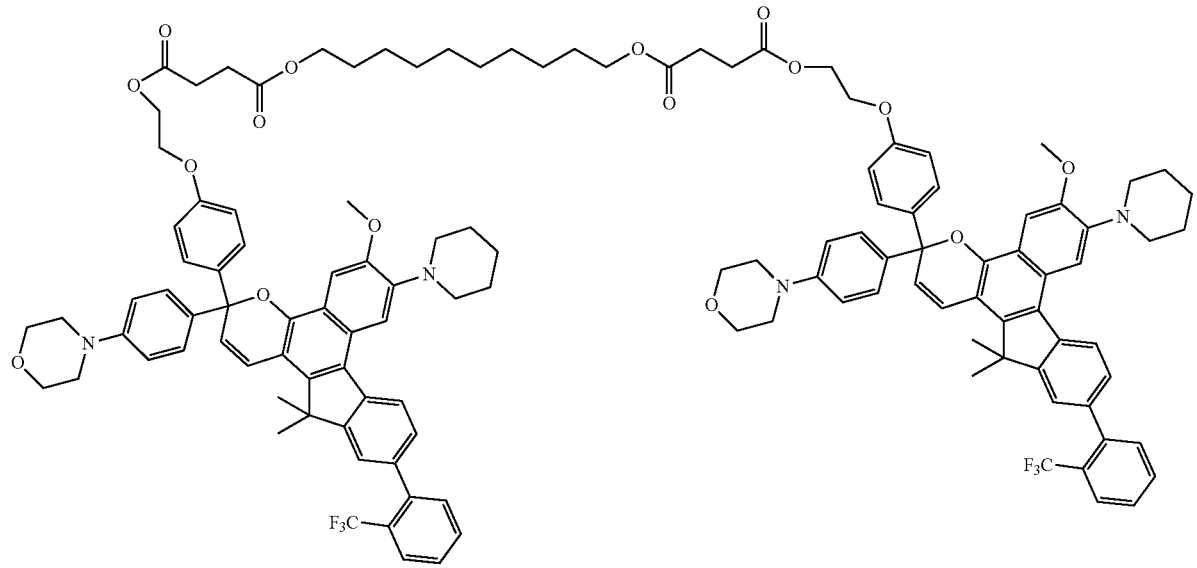 [SMILES: COc1cc2c3c(c4c(c2cc1N1CCCCC1)-c1ccc(-c2ccccc2C(F)(F)F)cc1C4(C)C)C=CC(c1ccc(OCCOC(=O)CCC(=O)OCCCCCCCCCCOC(=O)CCC(=O)OCCOc2ccc(C4(c5ccc(N6CCOCC6)cc5)C=Cc5c6c(c7cc(N8CCCCC8)c(OC)cc7c5O4)-c4ccc(-c5ccccc5C(F)(F)F)cc4C6(C)C)cc2)cc1)(c1ccc(N2CCOCC2)cc1)O3]

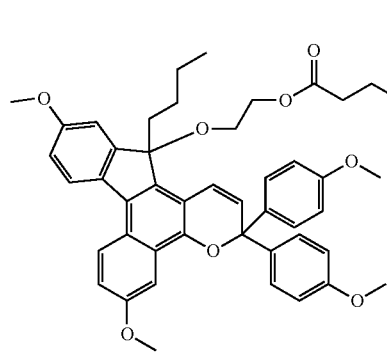
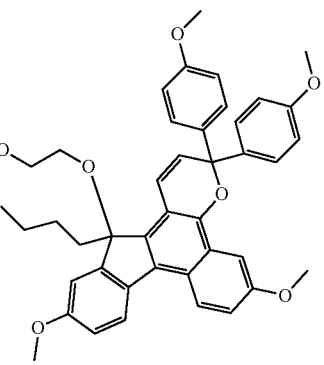

Example 11

Step 1

PM-B, 3-(4-methoxyphenyl)-3-(4-(2-hydroxy)ethoxyphenyl)-13,13-dimethyl-indeno[2',3':3,4]naphtho[1,2-b]pyran (5.0 g), pyridine (2.2 g), and anhydrous THF (60 mL) were combined in a reaction flask, and the mixture was stirred at room temperature. 1,6-Hexane bischloroformate (1.7 g) was added drop-wise to the solution. The mixture was further stirred at room temperature for 2 hours and filtered. The filtrate was concentrated and the residue was dissolved in ethyl acetate. Water (50 mL) was added to the solution and the mixture was partitioned. The ethyl acetate layer was recovered, concentrated and the residue was purified by silica gel chromatography (ethyl acetate/hexanes (v/v), 1/2) and the product was precipitated from methylene chloride/methanol (v/v: 1/4). The product was recovered by filtration as a purple-tinted powder (1.2 g). An NMR spectrum showed the product to have a structure consistent with hexane-1,6-diyl bis-(2-(4-(3-(4-methoxyphenyl)-13,13-dimethyl-3H,13H-indeno[2',3':3,4]naphtho[1,2-b]pyran-3-yl)phenoxy)ethyl)dicarbonate shown in the following graphic formula:

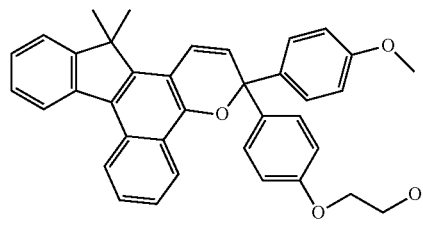

Example 12

Step 1

PM-E, 3-(4-morpholinophenyl)-3-(4-(2-hydroxy)ethoxyphenyl)-13,13-dimethyl-3H,13H-indeno[2',3':3,4]naphtho[1,2-b]pyran (3.5 g), succinic anhydride (1.18 g), 4-dimethylaminopyridine (36 mg), and anhydrous tetrahydrofuran (30 mL) were combined in a reaction flask. The reaction mixture was heated at reflux for 4 hours and then stirred at 55° C. overnight. The reaction mixture was concentrated. The product was isolated by silica gel chromatography using as eluant ethyl acetate/hexanes (v/v): 1/1, yielding 3.6 g of a blue-tinted solid, 3-(4-morpholinophenyl)-3-(4-(2-(3-carboxypropanoyl)oxy)ethoxy)phenyl)-13,13-dimethyl-3H,13H-indeno[2',3':3,4]naphtho[1,2-b]pyran.

Step 2

The product of Step 1 (1.0 g), triethylene glycol (0.108 g), N,N'-dicyclohexylcarbodiimide (0.325 g), 4-dimethylaminopyridine (0.105 g), dodecyl benzenesulfonic acid (0.235 g), and methylene chloride (40 mL) were combined in a reaction flask. The reaction mixture was stirred at room temperature overnight. The mixture was filtered and concentrated. The product was isolated by silica gel chromatography (ethyl acetate/hexanes (v/v): 2/1), yielding 0.5 g of a blue-tinted solid. An NMR spectrum showed the product to have a structure consistent with O,O'-((ethane-1,2-diylbis(oxy))bis(ethane-2,1-diyl))bis-(2-(4-(3-(4-morpholinophenyl)-13,13-dimethyl-3H,13H-indeno[2',3':3,4]naphtho[1,2-b]pyran-3-yl)phenoxy)ethyl)disuccinate shown in the following graphic formula:

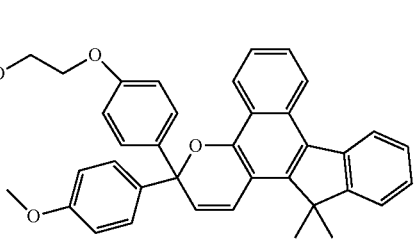

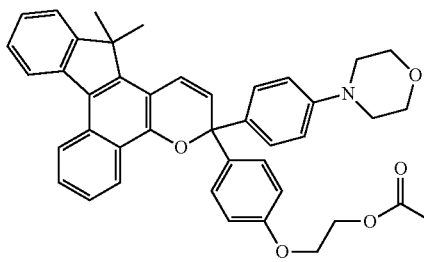
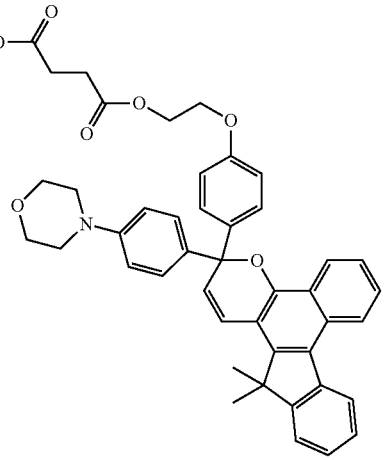

Example 13

Step 1

PM-E, 3-(4-morpholinophenyl)-3-(4-(2-hydroxy)ethoxyphenyl)-13,13-dimethyl-3H,13H-indeno[2',3':3,4]naphtho[1,2-b]pyran (3.5 g), succinic anhydride (1.18 g), 4-dimethylaminopyridine (36 mg), and anhydrous tetrahydrofuran (30 mL) were combined in a reaction flask. The reaction mixture was heated at reflux for 4 hours and then stirred at 55° C. overnight. The reaction mixture was concentrated. The product was isolated by silica gel chromatography (ethyl acetate/hexanes (v/v): 1/1), yielding 3.6 g of a blue-tinted solid, 3-(4-morpholinophenyl)-3-(4-(2-(3-carboxypropanoyl)oxy)ethoxy)phenyl)-13,13-dimethyl-3H,13H-indeno[2',3':3,4]naphtho[1,2-b]pyran.

Step 2

The product of Step 1 (0.58 g), tetraethylene glycol (0.08 g), N,N'-dicyclohexylcarbodiimide (0.19 g), 4-dimethylaminopyridine (0.06 g), dodecyl benzenesulfonic acid (0.135 g), and methylene chloride (25 mL) were combined in a reaction flask. The reaction mixture was stirred at room temperature overnight. The mixture was filtered and concentrated. The product was isolated by silica gel chromatography (ethyl acetate/hexanes (v/v): 3/1), yielding 0.3 g of an expanded blue-tinted foam. An NMR spectrum showed the product to have a structure consistent with O,O'-(((oxybis(ethane-2,1-diyl))bis(oxy))bis(ethane-2,1-diyl))bis-(2-(4-(3-(4-morpholinophenyl)-13,13-dimethyl-3H,13H-indeno[2',3':3,4]naphtho[1,2-b]pyran-3-yl)phenoxy)ethyl)disuccinate shown in the following graphic formula:

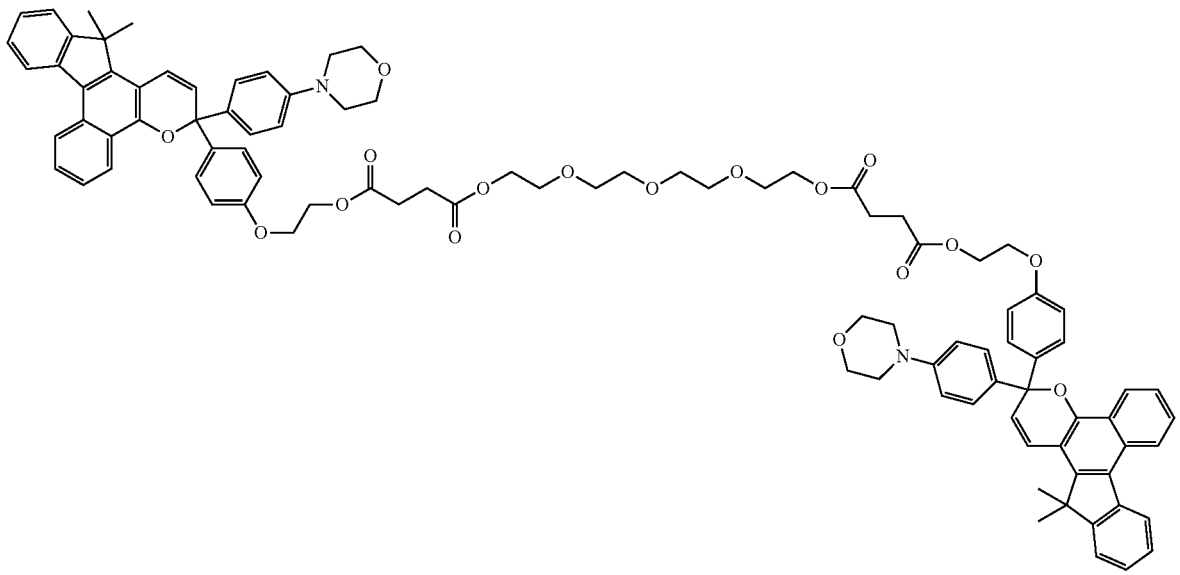 [SMILES: CC1(C)c2ccccc2-c2c1c1c(c3ccccc23)OC(c2ccc(OCCOC(=O)CCC(=O)OCCOCCOCCOCCOC(=O)CCC(=O)OCCOc3ccc(C4(c5ccc(N6CCOCC6)cc5)C=Cc5c6c(c7ccccc7c5O4)-c4ccccc4C6(C)C)cc3)cc2)(c2ccc(N3CCOCC3)cc2)C=C1]

Example 14

Step 1

2,3-Dimethoxy-7,7-dimethyl-9-bromo-7H-benzo[C]fluoren-5-ol (10.0, the product of Step 5 of Example 1 of US2006/0226402 A1, which example is hereby specifically incorporated by reference herein), tetrakis(triphenylphosphine) palladium (1.0 g), 4-(hydroxymethyl)phenylboronic acid (4.2 g), sodium carbonate (8.0 g), ethylene glycol dimethyl ether (100 mL), and water (100 mL) were combined in a reaction flask under a nitrogen atmosphere and stirred for 1 hour at room temperature. The mixture was then heated to reflux temperature for 24 hours. The reaction mixture was cooled to room temperature and poured into water (300 mL) and extracted with ethyl acetate (three times with 200 mL each time). The organic extracts were recovered, combined and the solvent was removed by rotary evaporation to give 9.1 g of a light yellow solid. NMR spectra showed the product to have a structure consistent with 2,3-dimethoxy-7,7-dimethyl-9-(4-hydroxymethyl)phenyl-7H-benzo[C]fluoren-5-ol.

Step 2

The product of Step 1 (3.0 g), 1-(4-methoxyphenyl)-1-(4-morpholinophenyl)-2-propyn-1-ol (3.0 g, made as described in Step 1 of Example 1 of U.S. Pat. No. 5,458,814, which disclosure is incorporated herein by reference, dodecylbenzene sulfonic acid (0.2 g) and chloroform (preserved with pentene, 250 mL) were combined in a reaction flask and stirred at room temperature for 5 hours. The reaction mixture was washed with 50% saturated aqueous NaHCO₃ (200 mL) and the organic layer was dried over anhydrous Na₂SO₄. The solvent was removed by rotary evaporation. Hot methanol was added to the resulting residue and the solution cooled to room temperature. The resulting precipitate was collected by vacuum filtration and washed with cold methanol yielding 3.4 g of 3-(4-methoxyphenyl)-3-(4-morpholinophenyl)-6,7-dimethoxy-11-(4-hydroxymethyl)phenyl-13,13-dimethyl-3H,13H-indeno[2',3':3,4]naphtho[1,2-b]pyran.

Step 3

The product of Step 2 (3.0 g), succinic anhydride (0.82 g), 4-dimethylaminopyridine (25 mg), and anhydrous tetrahydrofuran (30 mL) were combined in a reaction flask. The reaction mixture was heated at reflux for 4 hours and then stirred at 55° C. overnight. The reaction mixture was concentrated. The product was crystallized from acetone, yielding 2.8 g of an off-white solid, 3-(4-methoxyphenyl)-3-(4-morpholinophenyl)-6,7-dimethoxy-11-(4-(3-carboxypropanoyl)oxymethyl)phenyl-13,13-dimethyl-3H,13H-indeno[2',3':3,4]naphtho[1,2-b]pyran.

Step 4

The product of Step 3 (1.0 g), decanediol (0.10 g), N,N'-dicyclohexylcarbodiimide (0.27 g), 4-dimethylaminopyridine (0.09 g), dodecyl benzenesulfonic acid (0.20 g), and methylene chloride (30 mL) were combined in a reaction flask. The reaction mixture was stirred at room temperature overnight. The mixture was filtered and concentrated. The product was isolated by silica gel chromatography (ethyl acetate/hexanes (v/v): 2/1), yielding 0.6 g of a green-tinted solid. An NMR spectrum showed the product to have a structure consistent with O,O'-decane-1,10-diyl bis-(4-(3-(4-methoxyphenyl)-3-(4-morpholinophenyl)-6,7-dimethoxy-13,13-dimethyl-3H,13H-indeno[2',3':3,4]naphtho[1,2-b]pyran-11-yl)benzyl)disuccinate shown in the following graphic formula:

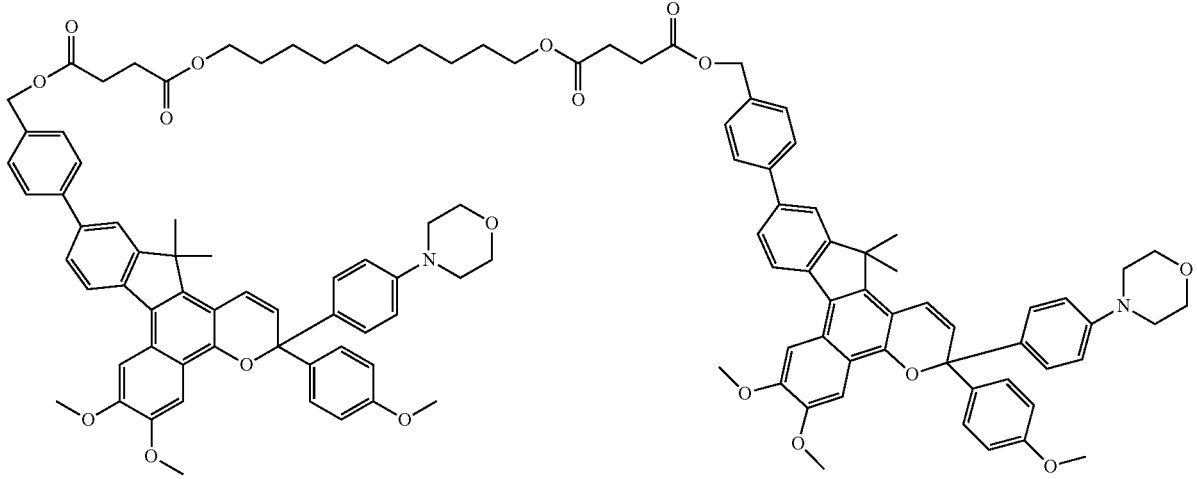 [SMILES: COc1ccc(C2(c3ccc(N4CCOCC4)cc3)C=Cc3c4c(c5cc(OC)c(OC)cc5c3O2)-c2ccc(-c3ccc(COC(=O)CCC(=O)OCCCCCCCCCCOC(=O)CCC(=O)OCc5ccc(-c6ccc7c(c6)C(C)(C)c6c8c(c9cc(OC)c(OC)cc9c6-7)OC(c6ccc(OC)cc6)(c6ccc(N7CCOCC7)cc6)C=C8)cc5)cc3)cc2C4(C)C)cc1]

Example 15

PM-B (5.0 g), meta-tetramethylxylylene diisocyanate (1.13 g), butylated hydroxytoluene (33 mg), dibutyltin dilaurate (33 mg), and ethyl acetate (30 mL) were combined in a reaction flask, and the mixture was heated at reflux for 2 hours. Methanol (5 mL) was added to the mixture to quench excess meta-tetramethylxylylene diisocyanate. The mixture was concentrated and the residue was purified by silica gel chromatography (ethyl acetate/hexanes (v/v): 2/3). The product was obtained as a purple-tinted solid (4.0 g). An NMR spectrum showed the product to have a structure consistent with 1,3-phenylene bis-(propane-2,2-diyl) bis-(2-(4-(3-(4-methoxyphenyl)-13,13-dimethyl-3H,13H-indeno[2',3':3,4]naphtho[1,2-b]pyran-3-yl)phenoxy)ethyl) dicarbamate shown in the following graphic formula:

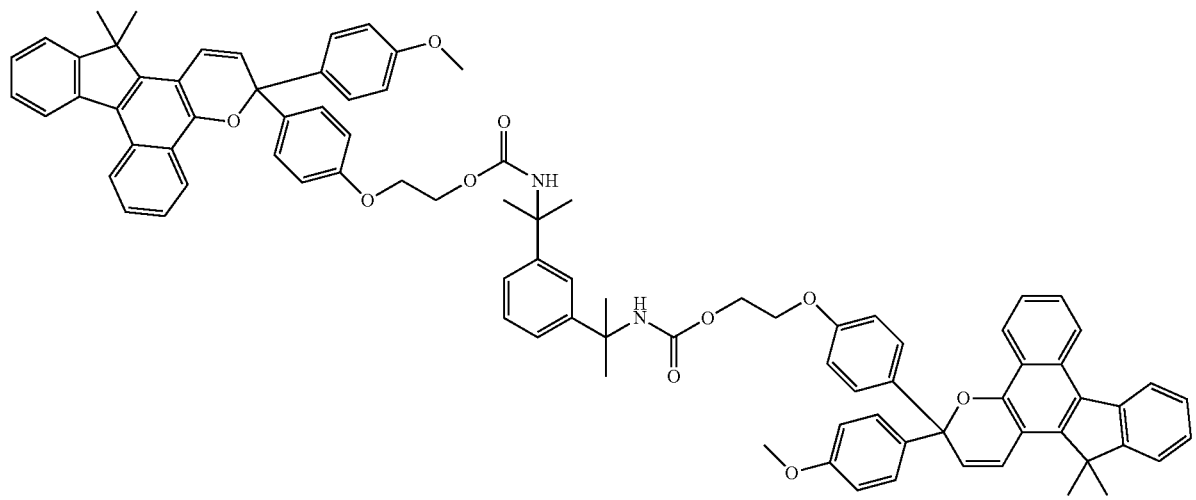 [SMILES: COc1ccc(C2(c3ccc(OCCOC(=O)NC(C)(C)c4cccc(C(C)(C)NC(=O)OCCOc5ccc(C6(c7ccc(OC)cc7)C=Cc7c8c(c9ccccc9c7O6)-c6ccccc6C8(C)C)cc5)c4)cc3)C=Cc3c4c(c5ccccc5c3O2)-c2ccccc2C4(C)C)cc1]

Example 16

PM-B, 3-(4-methoxyphenyl)-3-(4-(2-hydroxy)ethoxyphenyl)-13,13-dimethyl-3H,13H-indeno[2',3':3,4]naphtho[1,2-b]pyran (3.5 g), 1,6-hexane diisocyanate (0.56 g), butylated hydroxytoluene (23 mg), dibutyltin dilaurate (23 mg), and ethyl acetate (30 mL) were combined in a reaction flask, and the mixture was heated at reflux for 2 hours. Methanol (5 mL) was added to the mixture to quench excess 1,6-hexane diisocyanate. The mixture was concentrated and the residue was purified by silica gel chromatography (ethyl acetate/hexanes (v/v): 1/1). The product was obtained as a purple-tinted solid (1.8 g). An NMR spectrum showed the product to have a structure consistent with hexane-1,6-diyl bis-(2-(4-(3-(4-methoxyphenyl)-13,13-dimethyl-3H,13H-indeno[2',3':3,4]naphtho[1,2-b]pyran-3-yl)phenoxy)ethyl)dicarbamate shown in the following graphic formula:

Example 17

PM-B, 3-(4-methoxyphenyl)-3-(4-(2-hydroxy)ethoxyphenyl)-13,13-dimethyl-3H,13H-indeno[2',3':3,4]naphtho[1,2-b]pyran (5.0 g), 4,4'-diisocyanatodicyclohexylmethane (1.21 g), butylated hydroxytoluene (33 mg), dibutyltin dilaurate (33 mg), and ethyl acetate (30 mL) were combined in a reaction flask, and the mixture was heated at reflux for 2 hours. Methanol (5 mL) was added to the mixture to quench excess 4,4'-diisocyanatodicyclohexylmethane. The mixture was concentrated and the residue was purified by silica gel chromatography (ethyl acetate/hexanes (v/v): 1/2). The product was obtained as a purple-tinted solid (4.3 g). An NMR spectrum showed the product to have a structure consistent with methylene bis(cyclohexane-4,1-diyl) bis-(2-(4-(3-(4-methoxyphenyl)-13,13-dimethyl-3H,13H-indeno[2',3':3,4]naphtho[1,2-b]pyran-3-yl)phenoxy)ethyl)dicarbamate shown in the following graphic formula:

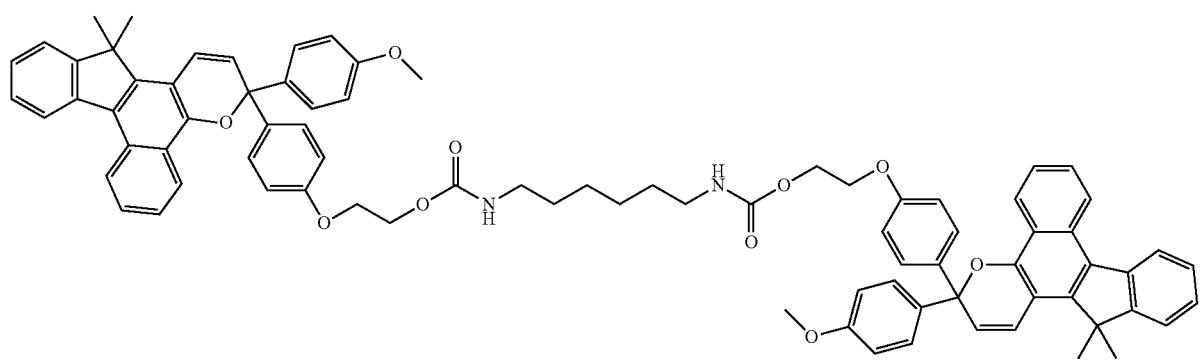 [SMILES: COc1ccc(C2(c3ccc(OCCOC(=O)NCCCCCCNC(=O)OCCOc4ccc(C5(c6ccc(OC)cc6)C=Cc6c7c(c8ccccc8c6O5)-c5ccccc5C7(C)C)cc4)cc3)C=Cc3c4c(c5ccccc5c3O2)-c2ccccc2C4(C)C)cc1]

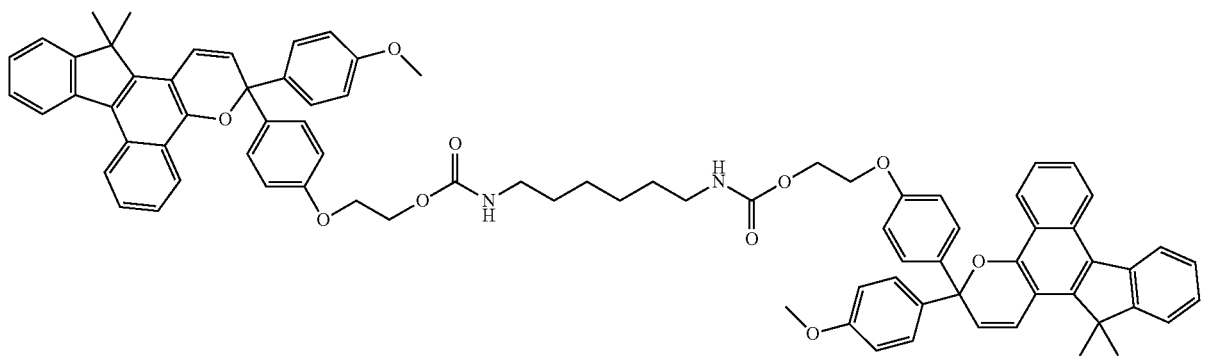 [SMILES: COc1ccc(C2(c3ccc(OCCOC(=O)NCCCCCCNC(=O)OCCOc4ccc(C5(c6ccc(OC)cc6)C=Cc6c7c(c8ccccc8c6O5)-c5ccccc5C7(C)C)cc4)cc3)C=Cc3c4c(c5ccccc5c3O2)-c2ccccc2C4(C)C)cc1]

Example 18

PM-B, 3-(4-methoxyphenyl)-3-(4-(2-hydroxy)ethoxyphenyl)-13,13-dimethyl-3H,13H-indeno[2',3':3,4]naphtho[1,2-b]pyran (5.0 g), isophorone diisocyanate (1.03 g), butylated hydroxytoluene (33 mg), dibutyltin dilaurate (33 mg), and ethyl acetate (30 mL) were combined in a reaction flask, and the mixture was heated at reflux for 2 hours. Methanol (5 mL) was added to the mixture to quench excess isophorone diisocyanate. The mixture was concentrated and the residue was purified by silica gel chromatography (ethyl acetate/hexanes (v/v): 1/2). The product was obtained as a purple-tinted solid (4.2 g). An NMR spectrum showed the product to have a structure consistent with 5-(2-(4-(3-(4-methoxyphenyl)-13,13-dimethyl-3H,13H-indeno[2',3':3,4]naphtho[1,2-b]pyran-3-yl)phenoxy)ethyloxycarbonylamino)-1-(2-(4-(3-(4-methoxyphenyl)-13,13-dimethyl-3H,13H-indeno[2',3':3,4]naphtho[1,2-b]pyran-3-yl)phenoxy)ethyloxycarbonylaminomethyl)-1,3,3-trimethylcyclohexane shown in the following graphic formula:

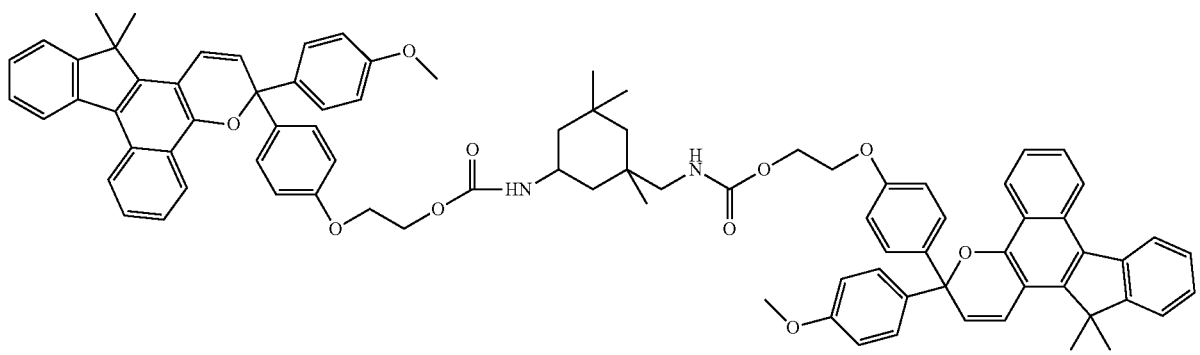 [SMILES: COc1ccc(C2(c3ccc(OCCOC(=O)NCC4(C)CC(NC(=O)OCCOc5ccc(C6(c7ccc(OC)cc7)C=Cc7c8c(c9ccccc9c7O6)-c6ccccc6C8(C)C)cc5)CC(C)(C)C4)cc3)C=Cc3c4c(c5ccccc5c3O2)-c2ccccc2C4(C)C)cc1]

Example 19

Step 1

PM-B, 3-(4-methoxyphenyl)-3-(4-(2-hydroxy)ethoxyphenyl)-13,13-dimethyl-3H,13H-indeno[2',3':3,4]naphtho[1,2-b]pyran (2.0 g), ε-caprolactone (3.7 g), and toluene (24 g) were combined in a reaction flask, and the mixture was stirred at room temperature for 30 minutes. Triisopropoxyaluminum (0.23 g) was added drop-wise to the solution. The mixture was further stirred at room temperature for 7 hours. Diluted hydrochloric acid (50 mL) was added to the solution and the mixture was partitioned. The recovered toluene layer was concentrated and the residue was purified by silica gel chromatography (ethyl acetate/hexanes (v/v), 1/2, 1/1, 4/1), yielding 4.9 g of a purple-tinted oil, 4-(3-(4-methoxyphenyl)-13,13-dimethyl-3H,13H-indeno[2',3':3,4]naphtho[1,2-b]pyran-3-yl)phenoxy)-poly(caprolactone-1000) hydroxylate.

Step 2

The product of Step 1 (4.9 g), meta-tetramethylxylylene diisocyanate (0.388 g), butylated hydroxytoluene (11 mg), dibutyltin dilaurate (11 mg), and ethyl acetate (30 mL) were combined in a reaction flask, and the mixture was heated at reflux for 2 hours. Methanol (5 mL) was added to the mixture to quench excess meta-tetramethylxylylene diisocyanate. The mixture was concentrated and the residue was purified by silica gel chromatography (ethyl acetate/hexanes (v/v): 1/1, 2/1). The product was obtained as a purple-tinted oil (2.2 g). An NMR spectrum showed the product to have a structure consistent with 1,3-phenylene bis(propane-2,2-diyl) bis-(1-(4-(3-(4-methoxyphenyl)-13,13-dimethyl-3H,13H-indeno[2',3':3,4]naphtho[1,2-b]pyran-3-yl)phenoxy)-poly(caprolactone-1000) dicarbamate shown in the following graphic formula in which the calculated caprolactone unit # is 9.5, but ~9 units of caprolactone were drawn for structure simplicity:

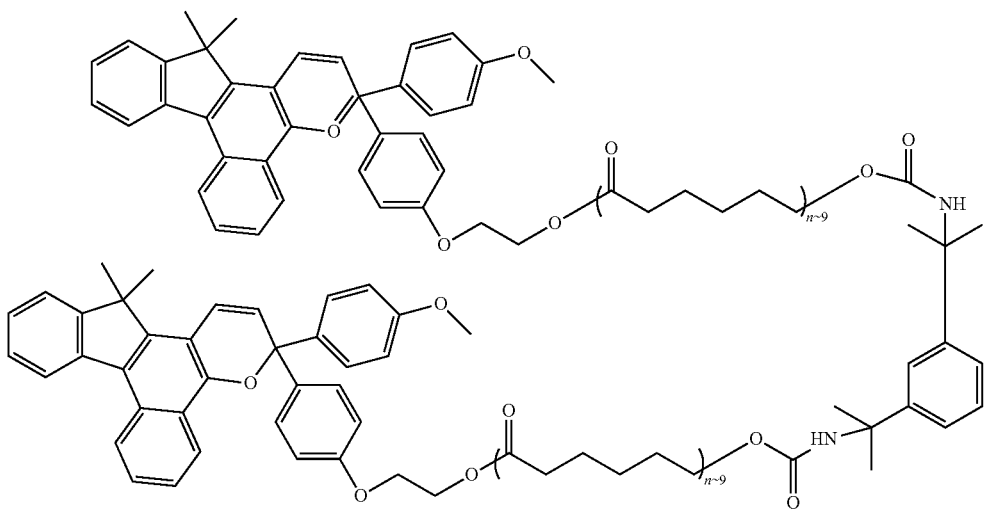

Example 20

PM-B, 3-(4-methoxyphenyl)-3-(4-(2-hydroxy)ethoxyphenyl)-13,13-dimethyl-3H,13H-indeno[2',3':3,4]naphtho[1,2-b]pyran (5.0 g), DESMODUR® N 3600 polyisocyanate (1.69 g), butylated hydroxytoluene (33 mg), dibutyltin dilaurate (33 mg), and ethyl acetate (40 mL) were combined in a reaction flask, and the mixture was heated at reflux for 2 hours. Methanol (5 mL) was added to the mixture to quench excess DESMODUR® N 3600 polyisocyanate. The mixture was concentrated and the residue was purified by silica gel chromatography (ethyl acetate/hexanes (v/v): 1/1). The product was obtained as a purple-tinted solid (3.5 g). An NMR spectrum showed the product to have a structure consistent with (2,4,6-trioxo-1,3,5-triazinane-1,3,5-triyl)tris(hexane-6,1-diyl) tris(2-(4-(3-(4-methoxyphenyl)-13,13-dimethyl-3H,13H-indeno[2',3':3,4]naphtho[1,2-b]pyran-3-yl)phenoxy)ethyl)tricarbamate shown in the following graphic formula:

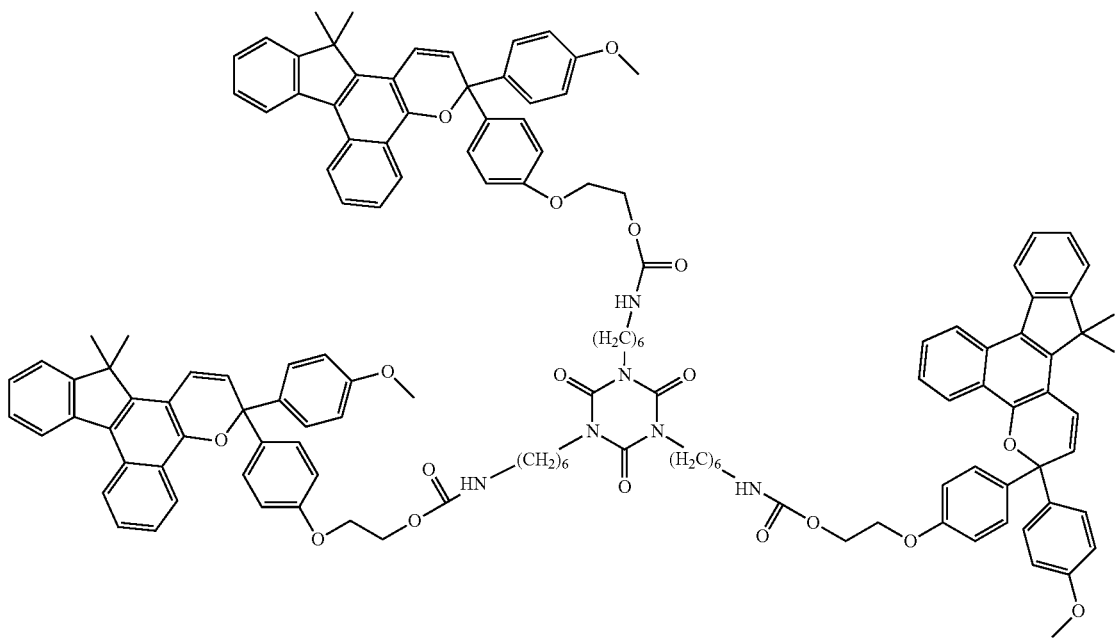

Example 21

PM-B, 3-(4-methoxyphenyl)-3-(4-(2-hydroxy)ethoxyphenyl)-13,13-dimethyl-3H,13H-indeno[2',3':3,4]naphtho[1,2-b]pyran (5.0 g), DESMODUR® 3200 polyisocyanate (1.69 g), butylated hydroxytoluene (33 mg), dibutyltin dilaurate (33 mg), and ethyl acetate (35 mL) were combined in a reaction flask, and the mixture was heated at reflux for 2.5 hours. Methanol (5 mL) was added to the mixture to quench excess DESMODUR® N 3200 polyisocyanate. The mixture was concentrated and the residue was purified by silica gel chromatography (ethyl acetate/hexanes (v/v): 2/1). The product was obtained as a purple-tinted solid (2.0 g). An NMR spectrum showed the product to have a structure consistent with 3-(4-(bis-((2-(4-(3-(4-methoxy)phenyl-13,13-dimethyl-3H,13H-indeno[2',3':3,4]naphtho[1,2-b]pyran-3-yl) phenoxy)ethyloxycarbonylamino)hexylaminocarbonyl)aminohexylaminocarbonyloxyethoxy)phenyl)-3-(4-methoxyphenyl)-13,13-dimethyl-3H,13H-indeno[2',3':3,4]naphtho[1,2-b]pyran shown in the following graphic formula:

mixture was partitioned. The toluene layer was recovered, concentrated and the residue was purified by silica gel chromatography (ethyl acetate/hexanes (v/v), 1/2, 1/1), yielding 4.4 g of a purple-tinted oil, 1-(4-(3-(4-methoxyphenyl)-13,13-dimethyl-3H,13H-indeno[2',3':3,4]naphtho[1,2-b]pyran-3-yl)phenoxy)-poly(caprolactone-1000) hydroxylate.

Step 2

The product of Step 1 (3.2 g), DESMODUR® N 3600 polyisocyanate (0.379 g), butylated hydroxytoluene (7 mg),

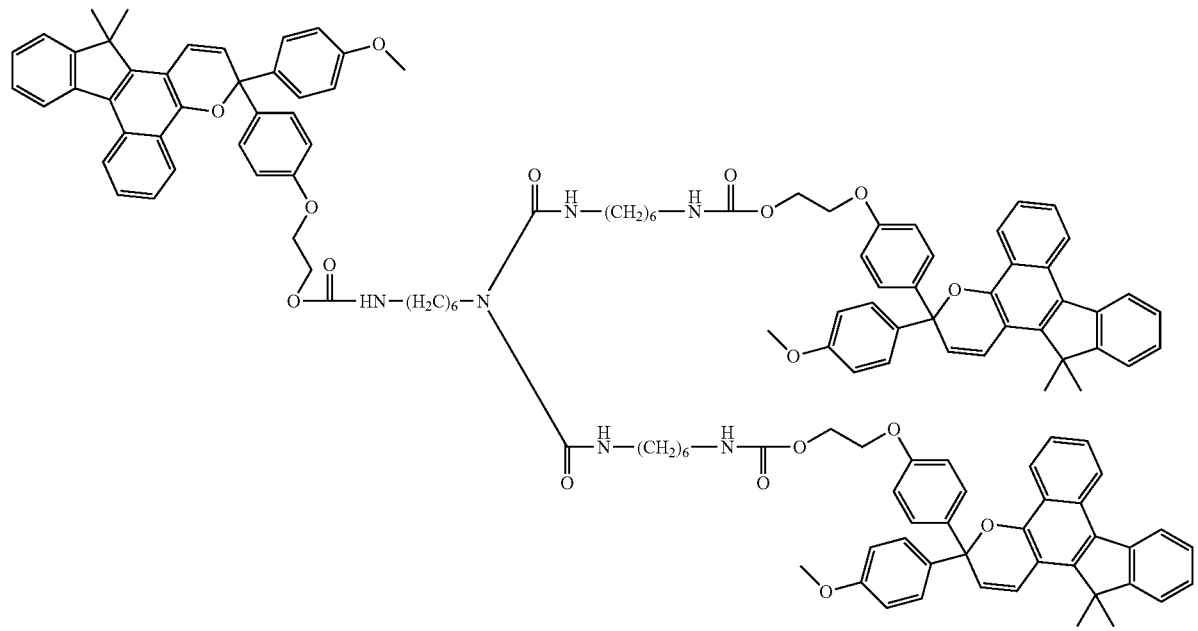

Example 22

Step 1

PM-B, 3-(4-methoxyphenyl)-3-(4-(2-hydroxy)ethoxyphenyl)-13,13-dimethyl-3H,13H-indeno[2',3':3,4]naphtho[1,2-b]pyran (2.0 g), ε-caprolactone (3.7 g), and toluene (25 g) were combined in a reaction flask, and the mixture was stirred at room temperature for 30 minutes. Triisopropoxyaluminum (0.23 g) was added drop-wise to the solution. The mixture was stirred at room temperature for 15 hours. Diluted hydrochloric acid (50 mL) was added to the solution and the dibutyltin dilaurate (7 mg), and ethyl acetate (30 g) were combined in a reaction flask, and the mixture was heated at reflux for 2 hours. Methanol (5 mL) was added to the mixture to quench excess DESMODUR® N 3600 polyisocyanate. The mixture was concentrated and the residue was purified by silica gel chromatography (ethyl acetate/hexanes (v/v): 1/1, 2/1). The product was obtained as a purple-tinted oil (1.5 g). An NMR spectrum showed the product to have a structure consistent with ((2,4,6-trioxo-1,3,5-triazinane-1,3,5-triyl) tris(hexane-6,1-diyl))tris(1-(4-(3-(4-methoxy)phenyl-13,13-dimethyl-3H,13H-indeno[2',3':3,4]naphtho[1,2-b]pyran-3-yl)phenoxyl poly(caprolactone-1000) tricarbamate shown in the following graphic formula:

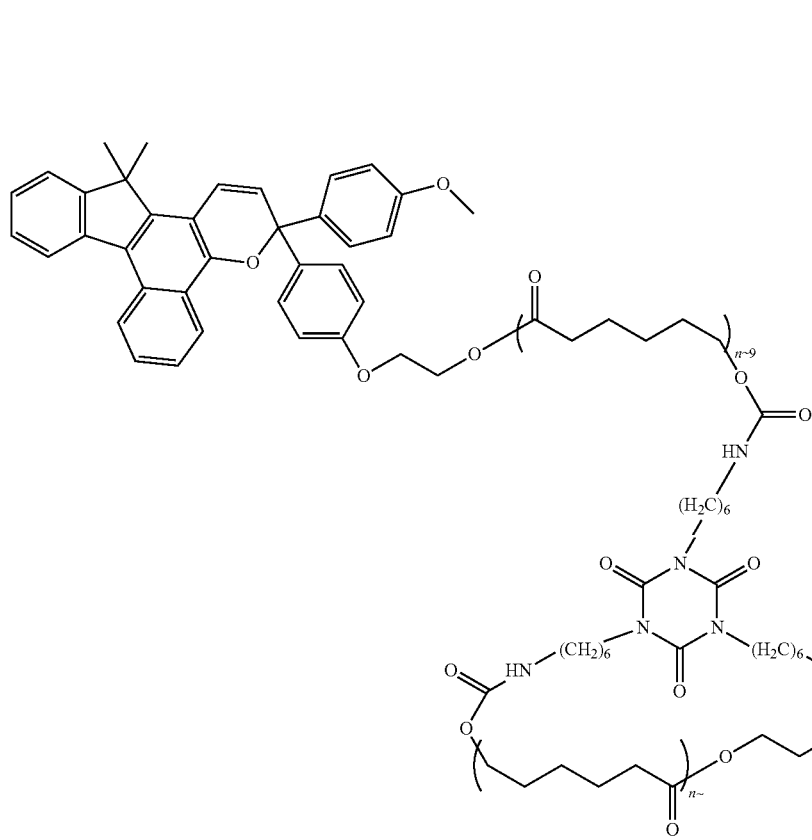
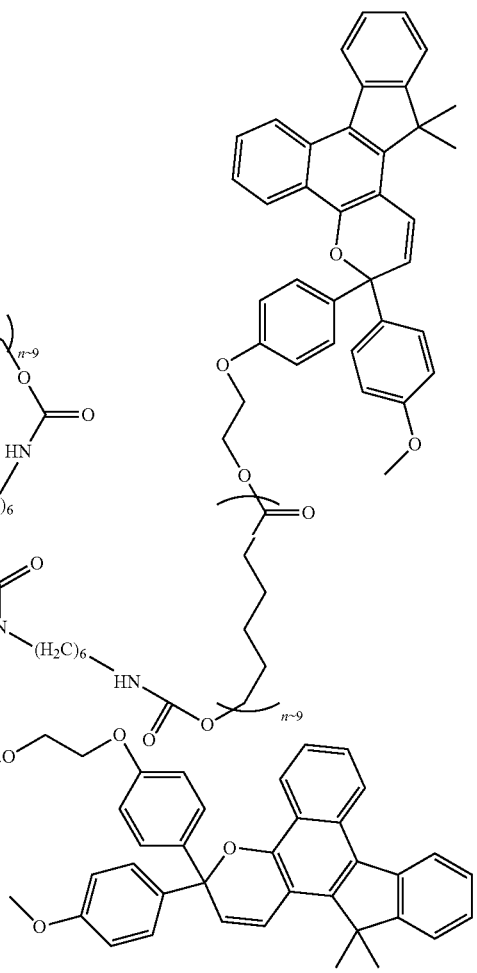

Part 2: Photochromic Performance Testing

The photochromic performance of the photochromic materials of Examples 1-22 were tested as follows. A quantity of the photochromic material to be tested, calculated to yield a $1.5 \times 10^{-3}$ M solution, was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis (2-methyl propionitrile) (AIBN). The photochromic material was dissolved into the monomer blend by stirring and gentle heating. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours and then lower it to 60° C. for at least 2 hours. After the mold was opened, the polymer sheet was cut using a utility knife to score the surface and snap into 2 inch (5.1 cm) test squares.

The photochromic test squares prepared as described above were tested for photochromic response on an optical bench. Prior to testing on the optical bench, the photochromic test squares were exposed to 365 nm ultraviolet light for about 15 minutes to cause the photochromic material to transform from the ground state-form to an activated-state form, and then placed in a 75° C. oven for about 15 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 73° F. (23° C.). The bench was fitted with a 300-watt xenon arc lamp, a remote controlled shutter, a Melles Griot KG2 filter that modifies the UV and IR wavelengths and acts as a heat-sink, neutral density filter(s) and a sample holder, situated within a water bath, in which the square to be tested was inserted. A collimated beam of light from a tungsten lamp was passed through the square at a small angle (approximately 30°) normal to the square. After passing through the square, the light from the tungsten lamp was directed to a collection sphere, where the light was blended, and on to an Ocean Optics S2000 spectrometer where the spectrum of the measuring beam was collected and analyzed. The $\lambda_{max\text{-}vis}$ is the wavelength in the visible spectrum at which the maximum absorption of the activated-state form of the photochromic compound in a test square occurs. The $\lambda_{max\text{-}vis}$ wavelength was determined by testing the photochromic test squares in a Varian Cary 300 UV-Visible spectrophotometer; it may also be calculated from the spectrum obtained by the S2000 spectrometer on the optical bench.

The saturated optical density ("Sat'd OD") for each test square was determined by opening the shutter from the xenon lamp and measuring the transmittance after exposing the test chip to 3 W/m2 UVA radiation for 30 minutes. The A at the Sat'd OD was calculated from the activated data measured by the S2000 spectrometer on the optical bench. The First Fade Half Life ("$T_{1/2}$") or Bleach Rate is the time interval in seconds for the absorbance of the activated-state form of the photochromic material in the test squares to reach one half the Sat'd OD absorbance value at room temperature (23° C.), after removal of the source of activating light.

The compounds of Examples 4, 7, 8 and 14 exhibited dual peak absorptions in the visible spectrum (lambda max visible) in distinct color regions. For each lambda max visible, the corresponding optical density (ΔOD/Min, and ΔOD at saturation) as well as fade half life are tabulated in Table 1 for the two bands (A and B) of peak absorption.

Part 3: Test Results

Results for the photochromic materials tested are listed below in Table 1.

TABLE 1

Photochromic Performance Results

| Example | $\lambda_{max}$ (nm) Visible | Sat. OD | Bleach Rate $T_{1/2}$ (sec) |
|---|---|---|---|
| 1 | 563 | 1.00 | 197 |
| 2 | 587 | 0.67 | 77 |
| 3 | 600 | 0.60 | 69 |
| 4A | 448 | 0.92 | 113 |
| 4B | 572 | 0.47 | 111 |
| 5 | 557 | 1.00 | 163 |
| 6 | 576 | 0.86 | 157 |
| 7A | 456 | 1.00 | 146 |
| 7B | 578 | 0.60 | 148 |
| 8A | 456 | 0.71 | 87 |
| 8B | 572 | 0.42 | 86 |
| 9 | 505 | 1.20 | 190 |
| 10 | 598 | 0.57 | 65 |
| 11 | 557 | 0.88 | 111 |
| 12 | 588 | 0.63 | 72 |
| 13 | 588 | 0.51 | 67 |
| 14A | 480 | 0.53 | 135 |
| 14B | 611 | 0.54 | 135 |
| 15 | 557 | 0.93 | 123 |
| 16 | 558 | 0.85 | 105 |
| 17 | 556 | 0.94 | 131 |
| 18 | 557 | 0.94 | 131 |
| 19 | 556 | 0.92 | 82 |
| 20 | 558 | 0.89 | 105 |
| 21 | 558 | 0.86 | 103 |
| 22 | 554 | 0.93 | 79 |

The present invention has been described with reference to specific details of particular embodiments thereof. It is not intended that such details be regarded as limitations upon the scope of the invention except insofar as and to the extent that they are included in the accompanying claims.

We claim:

1. A photochromic compound represented by the following Formula (I),

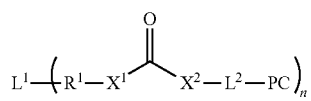

Formula (I)

wherein $L^1$ is a multivalent linking group selected from the group consisting of multivalent amine, multivalent linear or branched optionally substituted $C_1$-$C_{20}$ alkyl, multivalent optionally substituted $C_3$-$C_{12}$ cycloalkyl, multivalent optionally substituted $C_3$-$C_{12}$ heterocycloalkyl, multivalent optionally substituted aryl, multivalent optionally substituted heteroaryl, —$(R^4$—$O)_q$— wherein $R^4$ for each q is independently selected from divalent linear or branched $C_1$-$C_{12}$ alkyl, and q is from 1 to 50, and combinations of two or more thereof, n is at least 2, $R^1$ for each n is independently selected from group consisting of a bond, divalent linear or branched optionally substituted $C_1$-$C_{20}$ alkyl, divalent optionally substituted $C_3$-$C_{12}$ cyclo alkyl, divalent optionally substituted $C_3$-$C_{12}$ heterocycloalkyl, divalent optionally substituted aryl, divalent optionally substituted heteroaryl, and combinations of two or more thereof, $X^1$ for each n and $X^2$ for each n are each independently selected from the group consisting of O, NH, and a bond, provided that when $R^1$ is a bond and $X^1$ is a bond, $R^1$ and $X^1$ together define a bond, $L^2$ for each n is independently selected from a group represented by the following Formula (II),

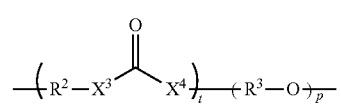

Formula (II)

wherein $R^2$ for each t is independently selected from the group consisting of a bond, divalent linear or branched $C_1$-$C_{20}$ alkyl, divalent optionally substituted $C_3$-$C_{12}$ cycloalkyl, divalent optionally substituted aryl, divalent optionally substituted heteroaryl, and combinations of two or more thereof, $R^3$ for each p is independently selected from the group consisting of divalent linear or branched $C_1$-$C_{20}$ alkyl, divalent optionally substituted $C_3$-$C_{12}$ cycloalkyl, divalent optionally substituted aryl, divalent optionally substituted heteroaryl, and combinations of two or more thereof, $X^3$ for each t and $X^4$ for each t are each independently selected from the group consisting of O, NH and a bond, provided that when $R^2$ is a bond and $X^3$ is a bond, $R^2$ and $X^3$ together define a bond, and provided that when $X^2$ is a bond, $R^2$ is a bond, $X^3$ is a bond, and t is greater than 0, $X^2$, $R^2$ and $X^3$ together define a bond, t, for each n, is 0 to 100, and p, for each n, is 0 to 20, provided that the sum of t and p is greater than 0, and PC for each n is independently a photochromic moiety.

2. The photochromic compound of claim 1, wherein n is 2, $L^1$ is a divalent linking group selected from the group consisting of divalent linear or branched optionally substituted $C_1$-$C_{20}$ alkyl, divalent optionally substituted $C_3$-$C_{12}$ cycloalkyl, divalent optionally substituted aryl, divalent optionally substituted heteroaryl, and combinations of two or more thereof, $R^1$ is a bond, $X^1$ is NH, and $X^2$ is O.

3. The photochromic compound of claim 2, wherein t is from 1 to 10, $R^2$ for each t is independently selected from divalent linear or branched $C_1$-$C_{10}$ alkyl, $X^3$ is a bond, $X^4$ is O, p is from 1 to 5, and R³ for each p is independently divalent linear or branched C₂-C₁₀ alkyl.

4. The photochromic compound of claim 1, wherein each PC is independently selected from the group consisting of indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, non-thermally reversible photochromic compounds, and mixtures thereof.

5. The photochromic compound of claim 4, wherein each PC is independently selected from an indeno[2',3':3,4]naphtho[1,2-b]pyran.

6. The photochromic compound of claim 5, wherein each PC is independently bonded to L² at a ring position of the naphthopyran selected from the group consisting of ring position 3, ring position 6, ring position 7, ring position 11, and ring position 13.

7. The photochromic compound of claim 5, wherein each PC is independently bonded to L² at a ring position of the naphthopyran selected from the group consisting of ring position 3, ring position 11, and ring position 13.

8. The photochromic compound of claim 1, wherein each PC has an activated visible light absorbance spectra, and the activated visible light absorbance spectra of each PC is substantially the same.

9. A photochromic article comprising the photochromic compound of claim 1.

10. The photochromic article of claim 9, wherein said photochromic article is selected from the group consisting of ophthalmic articles, display articles, windows, mirrors, active liquid crystal cell articles, and passive liquid crystal cell articles.

11. The photochromic article of claim 10, wherein said photochromic article is an ophthalmic articles, and said ophthalmic article is selected from the group consisting of corrective lenses, non-corrective lenses, contact lenses, intraocular lenses, magnifying lenses, protective lenses, and visors.

12. The photochromic article of claim 10, wherein said photochromic article is a display article, and said display articles is selected from the group consisting of screens, monitors, and security elements.

13. A photochromic composition comprising the photochromic compound of claim 1.

14. The photochromic compound of claim 1, wherein the photochromic compound is bis-(2-(4-(3-(4-methoxyphenyl)-7-methoxy-11-phenyl-13,13-dipropyl-3H,13H-indeno[2',3':3,4]naphtho[1,2-b]pyran-3-yl)phenoxy)ethyl) decanedioate.

* * * * *